US012310776B2

(12) United States Patent
Crawford et al.

(10) Patent No.: US 12,310,776 B2
(45) Date of Patent: *May 27, 2025

(54) FIXTURES FOR FLUOROSCOPIC IMAGING SYSTEMS AND RELATED NAVIGATION SYSTEMS AND METHODS

(71) Applicant: GLOBUS MEDICAL, INC., Audubon, PA (US)

(72) Inventors: Neil R. Crawford, Chandler, AZ (US); Norbert Johnson, North Andover, MA (US); Sanjay M. Joshi, Andover, MA (US)

(73) Assignee: Globus Medical, Inc., Audubon, PA (US)

( * ) Notice: Subject to any disclaimer, the term of this patent is extended or adjusted under 35 U.S.C. 154(b) by 613 days.

This patent is subject to a terminal disclaimer.

(21) Appl. No.: 17/547,605

(22) Filed: Dec. 10, 2021

(65) Prior Publication Data

US 2022/0378388 A1 Dec. 1, 2022

Related U.S. Application Data

(63) Continuation of application No. 16/860,125, filed on Apr. 28, 2020, now Pat. No. 11,253,216.

(51) Int. Cl.
*A61B 6/00* (2024.01)
(52) U.S. Cl.
CPC ............ *A61B 6/487* (2013.01); *A61B 6/4441* (2013.01)
(58) Field of Classification Search
CPC ....... A61B 6/487; A61B 34/20; A61B 6/5235; A61B 6/4441; A61B 90/39; A61B 2034/2059; A61B 2017/00725; A61B 2017/00973; A61B 2034/2055; A61B 2034/2048; A61B 2090/3762; A61B 2090/069; A61B 2034/2068; A61B 6/583;
(Continued)

(56) References Cited

U.S. PATENT DOCUMENTS 4,150,293 A 4/1979 Franke
5,246,010 A 9/1993 Gazzara et al.
(Continued)

FOREIGN PATENT DOCUMENTS

CN 101045015 A 10/2007
CN 103083784 A 5/2013
(Continued)

OTHER PUBLICATIONS

US 8,231,638 B2, 07/2012, Swarup et al. (withdrawn)

*Primary Examiner* — Irakli Kiknadze

(57) ABSTRACT

A fixture for a fluoroscopic x-ray imaging system is discussed, wherein the fluoroscopic imaging system includes a C-arm, an x-ray source at a first end of the C-arm, and an x-ray detector at a second end of the C-arm. The fixture includes a processor and memory coupled with the processor. The memory includes instructions that are executable by the processor so that the processor is configured to detect an x-ray emission from the x-ray source toward the x-ray detector, determine an offset of the x-ray source relative to the x-ray detector responsive to detecting the x-ray emission, and provide an indication of the offset of the x-ray source to a medical navigation system. Related methods and robotic systems are also discussed.

20 Claims, 54 Drawing Sheets

(58) Field of Classification Search
CPC .... A61B 2090/3983; A61B 2090/3966; A61B 2034/102; A61B 2090/376; A61B 34/10; A61B 90/361; A61B 90/37; A61B 34/70; A61B 34/30; A61B 2034/2065; A61B 2034/107; A61B 2034/108; A61B 6/4233; A61B 6/5211; A61B 6/4208; A61B 6/4411; A61B 6/12; A61B 6/4405; A61B 6/547; A61B 90/11; A61B 6/505; A61B 2034/2046; A61B 34/32; A61B 34/35; A61B 2034/2057; A61B 2034/207; A61B 2034/2072; A61B 2090/363; A61B 2090/371; A61B 2090/373; A61B 2090/3764; A61B 2090/3937; A61B 2090/3941; A61B 2090/3945; A61B 2090/3979; A61B 6/08; A61B 6/587; A61B 5/064; A61B 90/96; A61B 90/98; A61B 17/17; A61B 2017/00876; A61B 2034/2051; A61B 2090/034; A61B 2090/0811; A61B 6/0407; A61B 6/0492; A61B 6/503; A61B 2090/3954; A61B 2017/0092
USPC ...................................... 378/42, 62, 205–207
See application file for complete search history.

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |

(56) References Cited

U.S. PATENT DOCUMENTS

| | | |
|---|---|---|
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |

(56) References Cited

U.S. PATENT DOCUMENTS

| | | |
|---|---|---|
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |

(56) References Cited

U.S. PATENT DOCUMENTS

| | | | |
|---|---|---|---|
| 9,420,975 B2 | 8/2016 | Gutfleisch et al. | |
| 9,492,235 B2 | 11/2016 | Hourtash et al. | |
| 9,592,096 B2 | 3/2017 | Maillet et al. | |
| 9,750,465 B2 | 9/2017 | Engel et al. | |
| 9,757,203 B2 | 9/2017 | Hourtash et al. | |
| 9,795,354 B2 | 10/2017 | Menegaz et al. | |
| 9,814,535 B2 | 11/2017 | Bar et al. | |
| 9,820,783 B2 | 11/2017 | Donner et al. | |
| 9,833,265 B2 | 11/2017 | Donner et al. | |
| 9,848,922 B2 | 12/2017 | Tohmeh et al. | |
| 9,867,588 B2 * | 1/2018 | Amiri | A61B 6/584 |
| 9,925,011 B2 | 3/2018 | Gombert et al. | |
| 9,931,025 B1 | 4/2018 | Graetzel et al. | |
| 10,034,717 B2 | 7/2018 | Miller et al. | |
| 10,568,638 B2 | 2/2020 | Sun et al. | |
| 10,617,482 B2 | 4/2020 | Houser et al. | |
| 11,253,216 B2 * | 2/2022 | Crawford | A61B 34/20 |
| 2001/0036302 A1 | 11/2001 | Miller | |
| 2002/0035321 A1 | 3/2002 | Bucholz et al. | |
| 2002/0109705 A1 | 8/2002 | Hofstetter et al. | |
| 2003/0223539 A1 * | 12/2003 | Granfors | H04N 25/30 |
| | | | 348/E5.081 |
| 2004/0015077 A1 | 1/2004 | Sati et al. | |
| 2004/0068172 A1 | 4/2004 | Nowinski et al. | |
| 2004/0076259 A1 | 4/2004 | Jensen et al. | |
| 2005/0096502 A1 | 5/2005 | Khalili | |
| 2005/0143651 A1 | 6/2005 | Verard et al. | |
| 2005/0171558 A1 | 8/2005 | Abovitz et al. | |
| 2006/0100610 A1 | 5/2006 | Wallace et al. | |
| 2006/0115054 A1 * | 6/2006 | Yatsenko | A61B 6/4291 |
| | | | 378/207 |
| 2006/0173329 A1 | 8/2006 | Marquart et al. | |
| 2006/0184396 A1 | 8/2006 | Dennis et al. | |
| 2006/0241416 A1 | 10/2006 | Marquart et al. | |
| 2006/0291612 A1 | 12/2006 | Nishide et al. | |
| 2007/0015987 A1 | 1/2007 | Benlloch Baviera et al. | |
| 2007/0021738 A1 | 1/2007 | Hasser et al. | |
| 2007/0038059 A1 | 2/2007 | Sheffer et al. | |
| 2007/0041508 A1 * | 2/2007 | Tubbs | A61B 6/08 |
| | | | 378/207 |
| 2007/0073133 A1 | 3/2007 | Schoenefeld | |
| 2007/0156121 A1 | 7/2007 | Millman et al. | |
| 2007/0156157 A1 | 7/2007 | Nahum et al. | |
| 2007/0167712 A1 | 7/2007 | Keglovich et al. | |
| 2007/0233238 A1 | 10/2007 | Huynh et al. | |
| 2008/0004523 A1 | 1/2008 | Jensen | |
| 2008/0013809 A1 | 1/2008 | Zhu et al. | |
| 2008/0033283 A1 | 2/2008 | Dellaca et al. | |
| 2008/0046122 A1 | 2/2008 | Manzo et al. | |
| 2008/0082109 A1 | 4/2008 | Moll et al. | |
| 2008/0108912 A1 | 5/2008 | Node-Langlois | |
| 2008/0108991 A1 | 5/2008 | von Jako | |
| 2008/0109012 A1 | 5/2008 | Falco et al. | |
| 2008/0144906 A1 | 6/2008 | Allred et al. | |
| 2008/0161680 A1 | 7/2008 | von Jako et al. | |
| 2008/0161682 A1 | 7/2008 | Kendrick et al. | |
| 2008/0177203 A1 | 7/2008 | von Jako | |
| 2008/0214922 A1 | 9/2008 | Hartmann et al. | |
| 2008/0228068 A1 | 9/2008 | Viswanathan et al. | |
| 2008/0228196 A1 | 9/2008 | Wang et al. | |
| 2008/0235052 A1 | 9/2008 | Node-Langlois et al. | |
| 2008/0269596 A1 | 10/2008 | Revie et al. | |
| 2008/0287771 A1 | 11/2008 | Anderson | |
| 2008/0287781 A1 | 11/2008 | Revie et al. | |
| 2008/0300477 A1 | 12/2008 | Lloyd et al. | |
| 2008/0300478 A1 | 12/2008 | Zuhars et al. | |
| 2008/0302950 A1 | 12/2008 | Park et al. | |
| 2008/0306490 A1 | 12/2008 | Lakin et al. | |
| 2008/0319311 A1 | 12/2008 | Hamadeh | |
| 2009/0012509 A1 | 1/2009 | Csavoy et al. | |
| 2009/0030428 A1 | 1/2009 | Omori et al. | |
| 2009/0080737 A1 | 3/2009 | Battle et al. | |
| 2009/0185655 A1 | 7/2009 | Koken et al. | |
| 2009/0198121 A1 | 8/2009 | Hoheisel | |
| 2009/0216113 A1 | 8/2009 | Meier et al. | |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |

(56) References Cited

U.S. PATENT DOCUMENTS

| | | |
|---|---|---|
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0051794 A1 | 2/2016 | Guibin et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0119339 A1* | 5/2017 | Johnson ............... A61B 6/58 |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2019/0046279 A1 | 2/2019 | Hille et al. |
| 2019/0328482 A1* | 10/2019 | Izmirli ............. A61B 6/0492 |
| 2020/0320721 A1* | 10/2020 | Holladay ............. G06T 3/147 |

FOREIGN PATENT DOCUMENTS

| | | |
|---|---|---|
| CN | 206026424 U | 3/2017 |
| EP | 3295887 A1 | 3/2018 |
| JP | H0928701 A | 2/1997 |
| JP | 2009028701 A | 2/2009 |
| JP | 2018011938 A | 1/2018 |
| JP | 2018051306 A | 4/2018 |

* cited by examiner

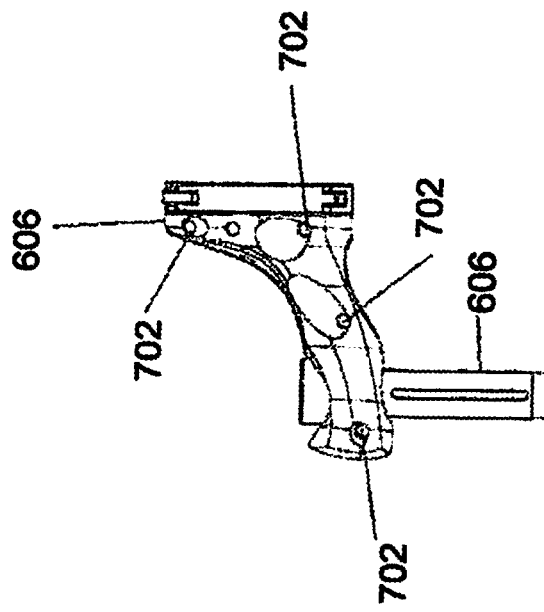
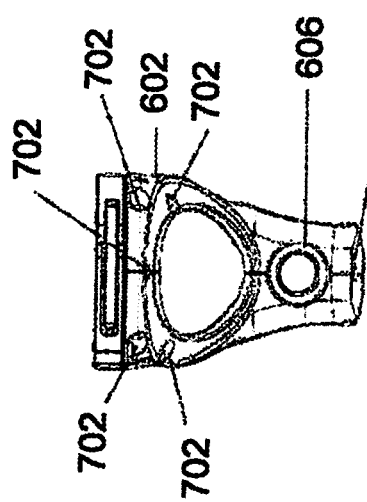
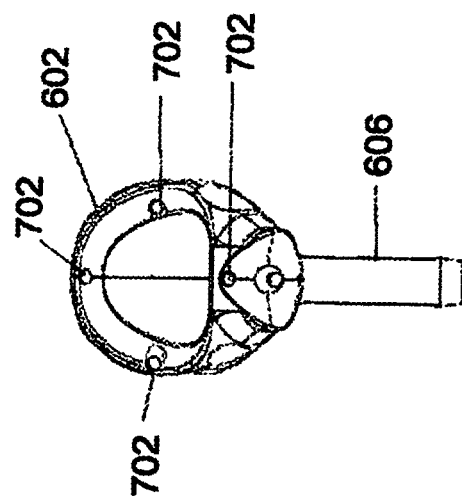

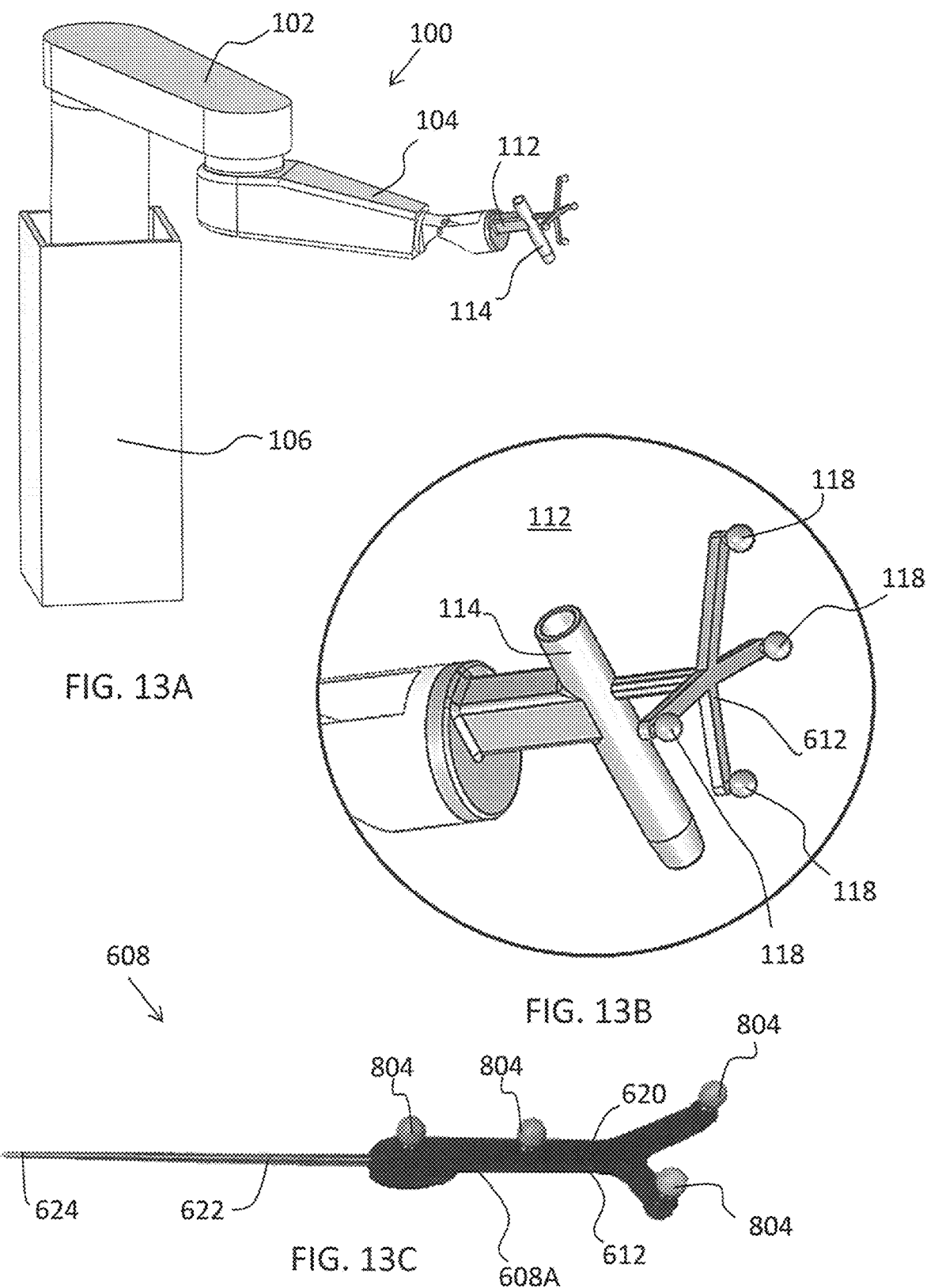

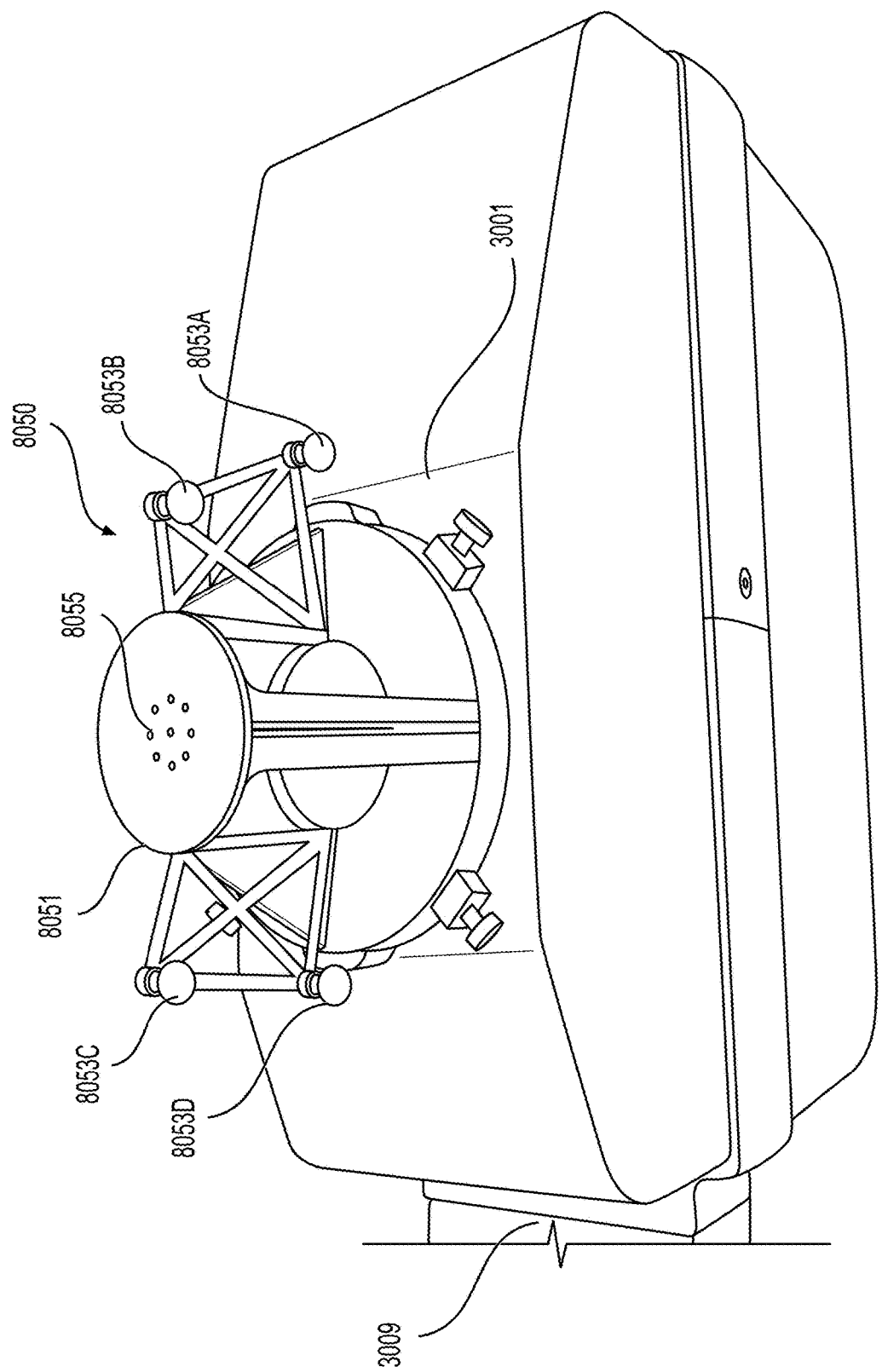

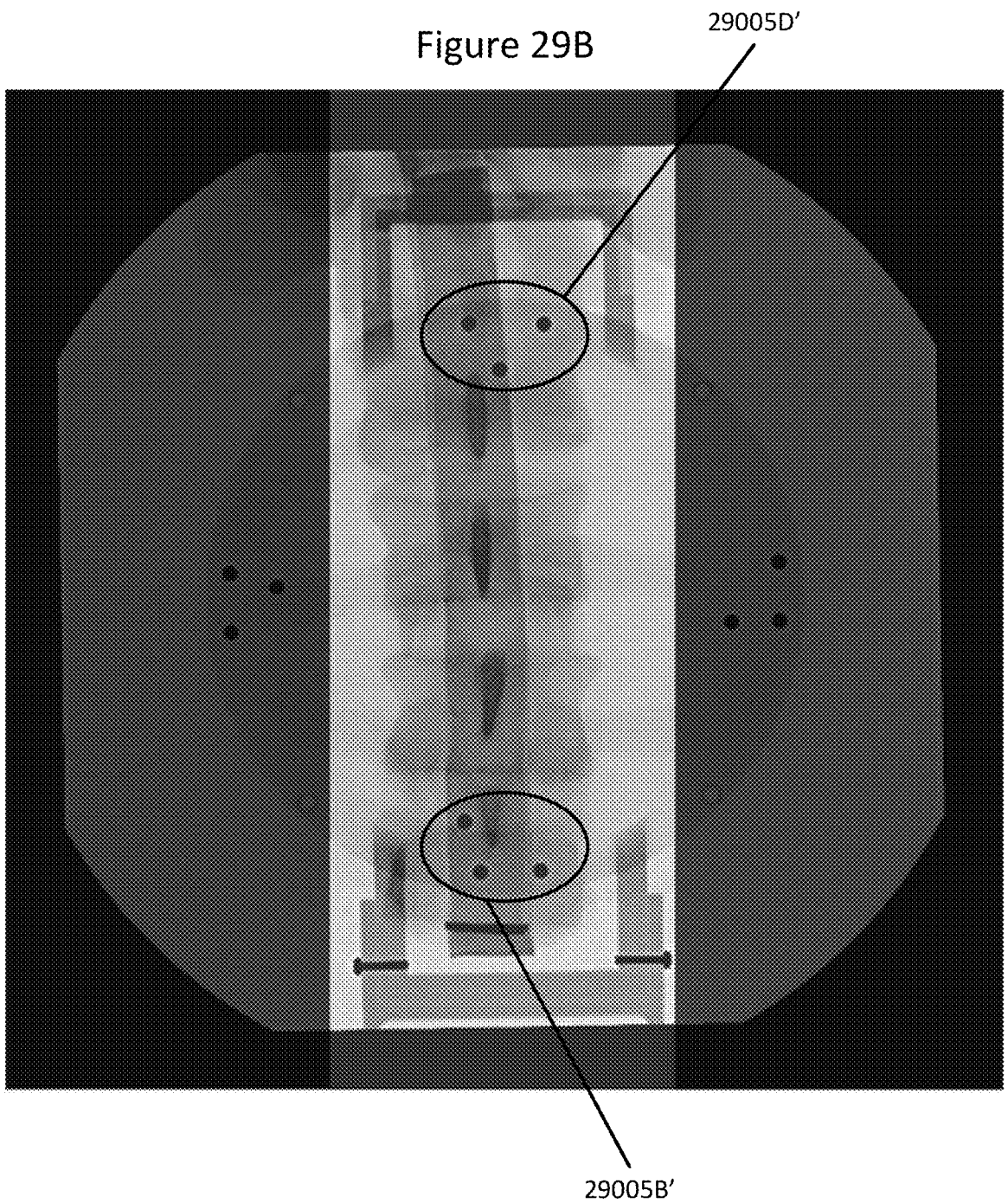

29005A'

29005C'

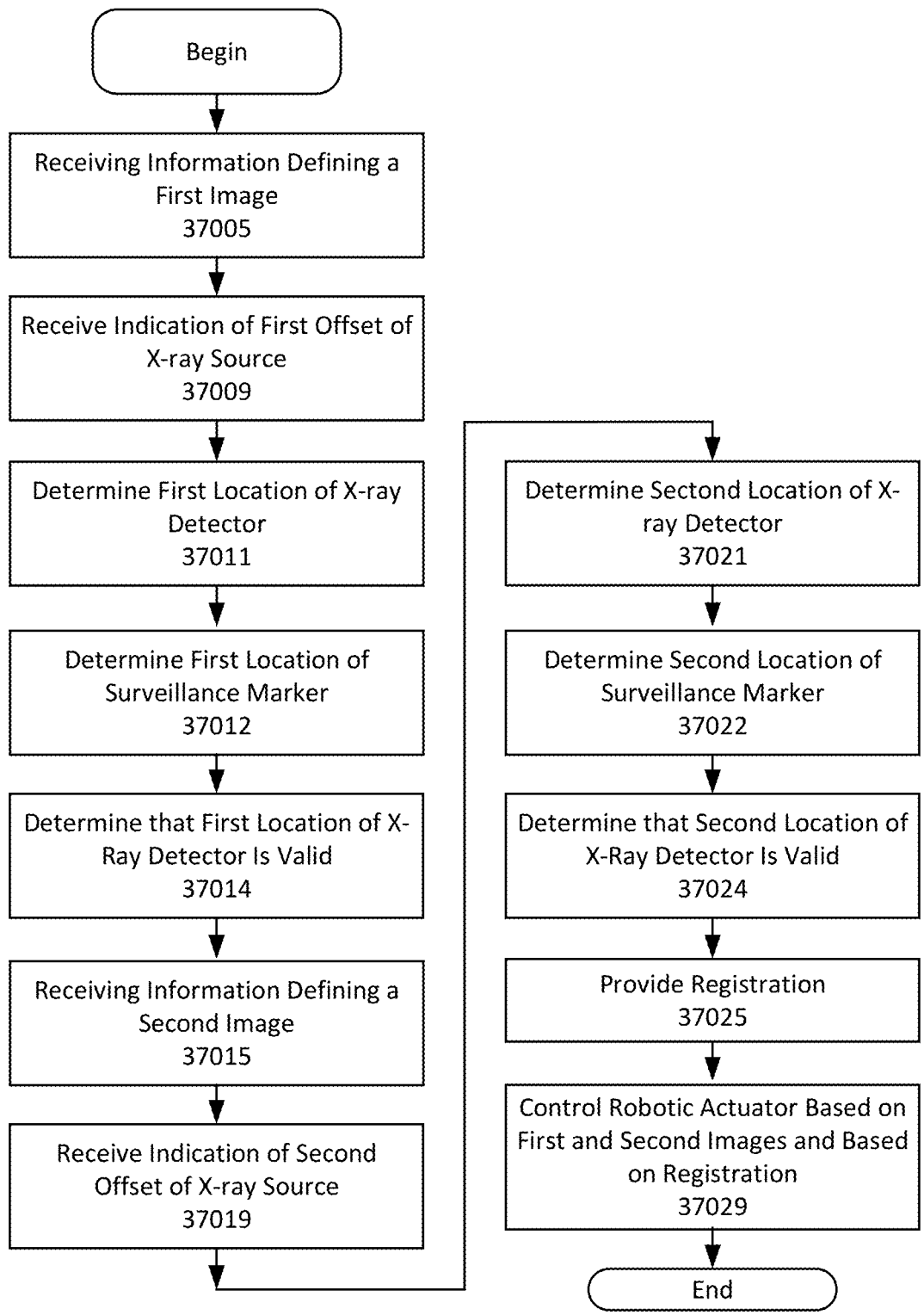

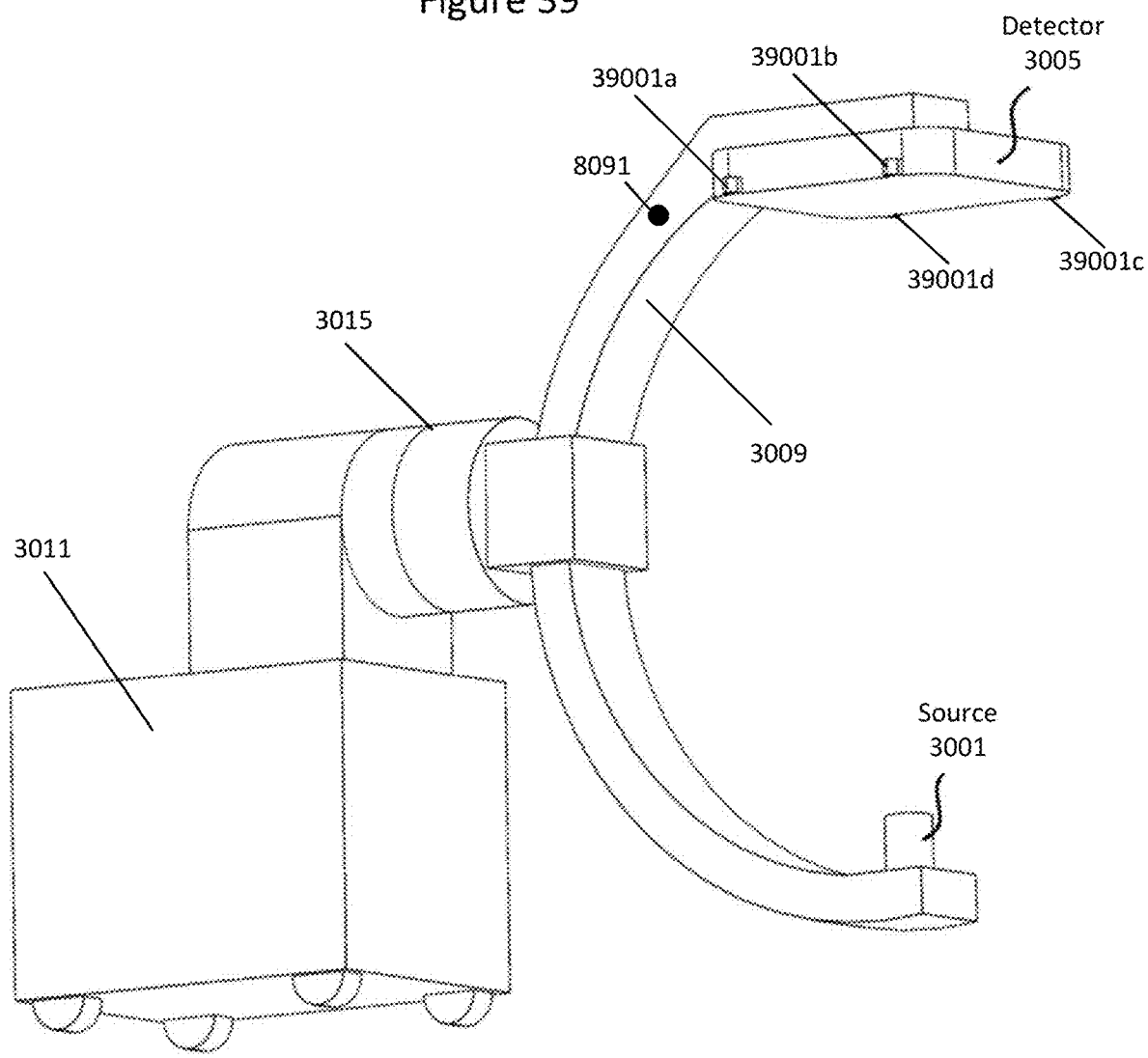

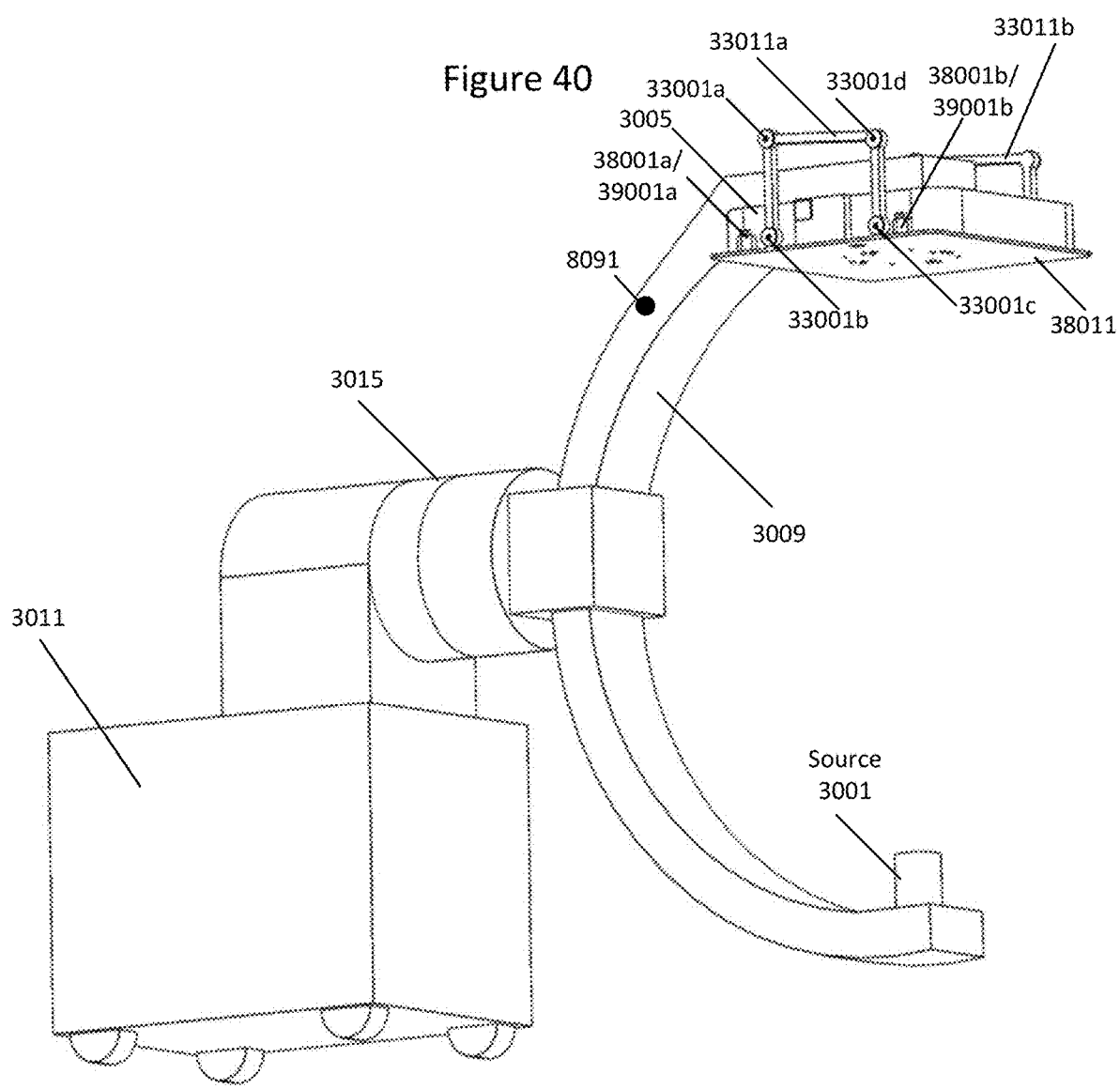

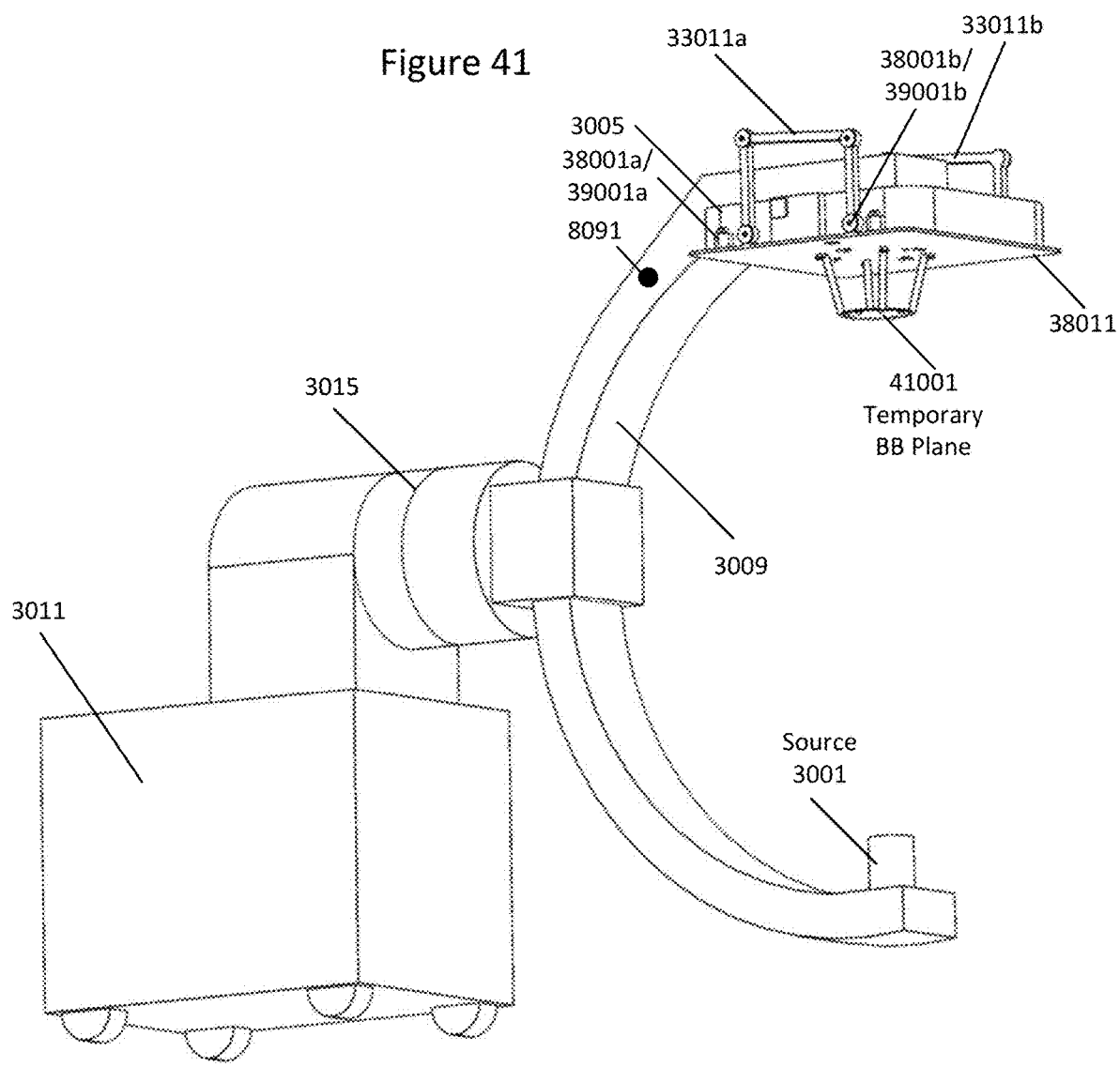

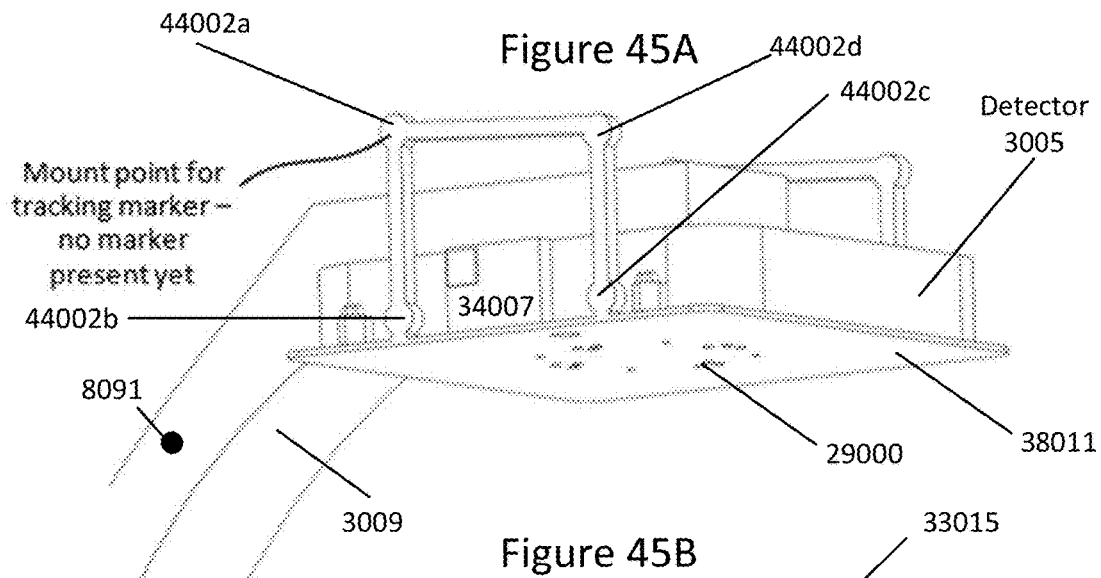
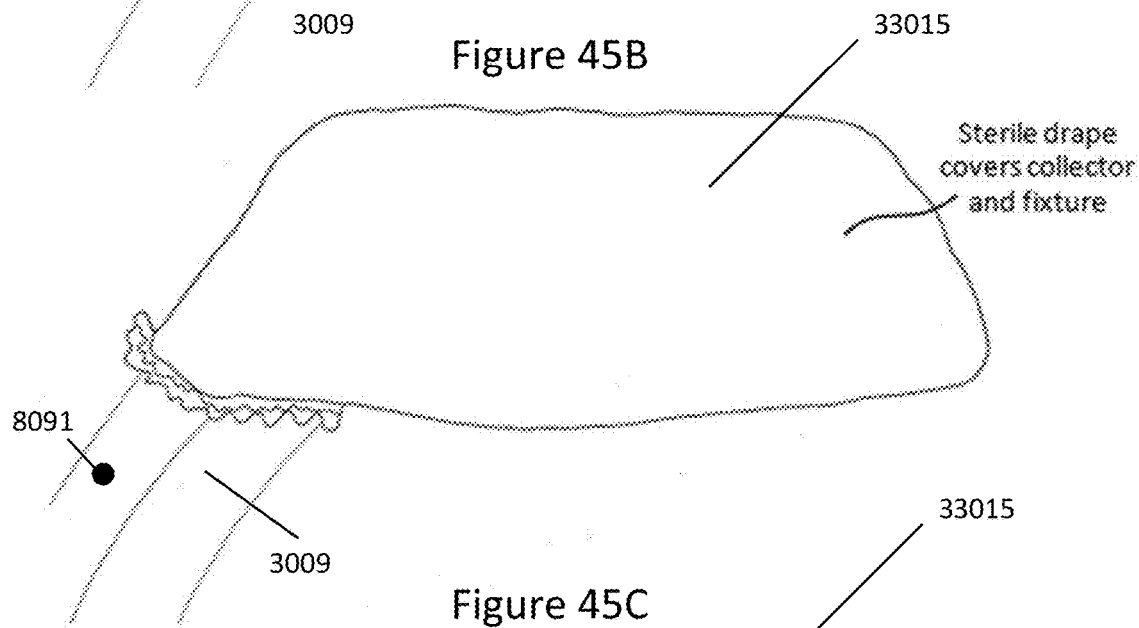
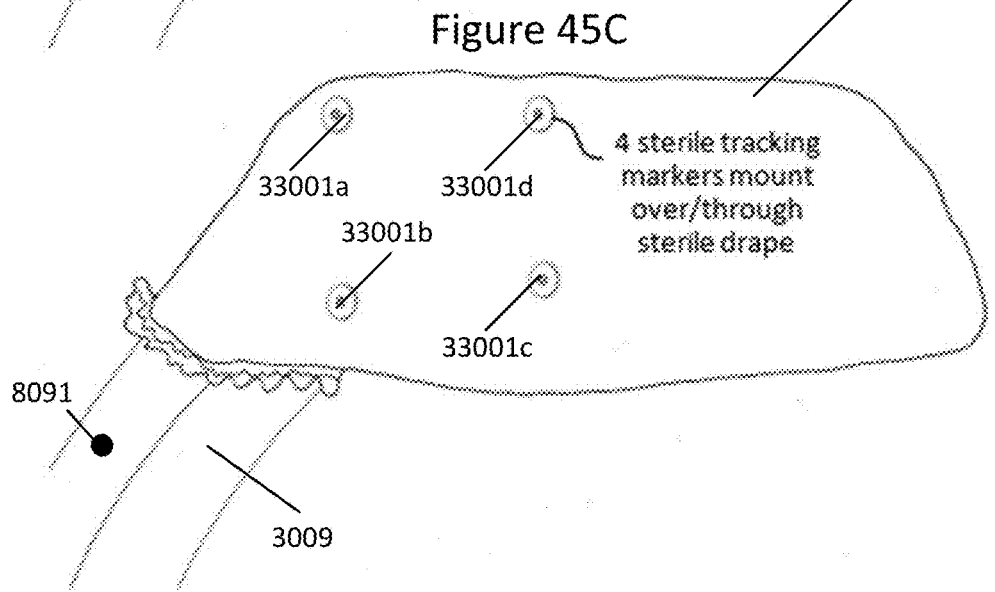

FIXTURES FOR FLUOROSCOPIC IMAGING SYSTEMS AND RELATED NAVIGATION SYSTEMS AND METHODS

CROSS REFERENCE TO RELATED APPLICATIONS

This application is a continuation application which claims priority to U.S. patent application Ser. No. 16/860,125 filed on Apr. 28, 2020 which is incorporated in its entirety herein.

FIELD

The present disclosure relates to medical devices, and more particularly, fluoroscopic x-ray imaging systems and related methods and devices.

BACKGROUND

Prior to and/or during a surgical procedure performed using surgical navigation, registration between a coordinate system of a fluoroscopic x-ray imaging system, a coordinate system of a tracking system (e.g., a camera coordinate system), and/or a coordinate system of a pre-operative image of the anatomy (e.g., an MRI or CT scan) may be desired. Because the fluoroscopic imaging system is a large piece of equipment with an x-ray source and an x-ray detector supported at opposite ends of a large C-arm, the C-arm may flex differently in different positions so that relative positions of the x-ray source and the x-ray detector may be different at different positions of the C-arm, making it difficult to properly register resulting images with respect to other coordinate systems.

SUMMARY

According to some embodiments of inventive concepts, a surgical imaging system is configured for use with a fluoroscopic imaging system. The fluoroscopic imaging system includes a C-arm, an x-ray source at a first end of the C-arm, and an x-ray detector at a second end of the C-arm, and the fluoroscopic imaging system is configured to generate x-ray images based on x-rays received at the x-ray detector from the x-ray source. The surgical imaging system includes a fixture and a medical navigation system. The fixture includes an x-ray opaque fiducial pattern in a single plane, and the fixture is coupled with the x-ray detector so that the x-ray opaque fiducial pattern is on a surface of the x-ray detector between the x-ray detector and the x-ray emitter. The medical navigation system is configured to receive a first patient image from the fluoroscopic imaging system corresponding to a first orientation of the C-arm with the first patient image including first shadows corresponding to the x-ray opaque fiducial pattern. The medical navigation system is also configured to receive a second patient image from the fluoroscopic imaging system corresponding to a second orientation of the C-arm with the second patient image including second shadows corresponding to the x-ray opaque fiducial pattern. The medical navigation system is further configured to provide a registration between a tracking coordinate system for a physical space monitored by tracking cameras and an image coordinate system for the first patient image and the second patient image based on a correlation of offsets of the x-ray source relative to the x-ray detector as a function of an orientation of the x-ray detector relative to gravity and based on the first shadows in the first patient image and the second shadows in the second patient image.

According to some embodiments of inventive concepts, a fixture is provided for a fluoroscopic x-ray imaging system, wherein the fluoroscopic x-ray imaging system includes a C-arm, an x-ray source at a first end of the C-arm, and an x-ray detector at a second end of the C-arm. The fixture includes a processor and memory coupled with the processor. The memory includes instructions that are executable by the processor so that the fixture is configured to detect an x-ray emission from the x-ray source toward the x-ray detector, determine an offset of the x-ray source relative to the x-ray detector responsive to detecting the x-ray emission, and provide an indication of the offset of the x-ray source to a medical navigation system.

According to some other embodiments of inventive concepts, a method is provided to operate a fixture for a fluoroscopic x-ray imaging system including a C-arm, an x-ray source at a first end of the C-arm, and an x-ray detector at a second end of the C-arm. An x-ray emission from the x-ray source toward the x-ray detector is detected. An offset of the x-ray source relative to the x-ray detector is determined responsive to detecting the x-ray emission. The offset of the x-ray source is provided to a medical navigation system.

According to still other embodiments of inventive concepts, a medical navigation system includes a processor and memory coupled with the processor wherein the memory includes instructions that are executable by the processor so that the medical navigation system is configured to perform the following operations. The processor is configured to receive information defining a first image from a fluoroscopic x-ray imaging system, wherein the fluoroscopic x-ray imaging system includes a C-arm, an x-ray source at a first end of the C-arm, and an x-ray detector at a second end of the C-arm. The processor is configured to provide/receive an indication of a first offset of the x-ray source relative to the x-ray detector, with the first offset being associated with the first image. The processor is configured to receive information defining a second image from the fluoroscopic x-ray imaging system, with the first image and the second image being different. The processor is configured to provide/receive an indication of a second offset of the x-ray source relative to x-ray detector, with the second offset being associated with the second image and with the first offset and the second offset being different The processor is configured to provide a registration between a tracking coordinate system for a physical space monitored by tracking sensors and an image coordinate system for the first and second images from the fluoroscopic x-ray imaging system, with the registration being provided based on the indications of the first offset and the second offset.

According to yet other embodiments of inventive concepts, a method is provided to operate a medical navigation system. Information defining a first image is received from a fluoroscopic x-ray imaging system, with the fluoroscopic x-ray imaging system including a C-arm, an x-ray source at a first end of the C-arm, and an x-ray detector at a second end of the C-arm. An indication of a first offset of the x-ray source relative to the x-ray detector is provided/received with the first offset being associated with the first image. Information defining a second image is received from the fluoroscopic x-ray imaging system, with the first and second images being different. An indication of a second offset of the x-ray source relative to the x-ray detector is provided/received, with the second offset being associated with the second image and with the first offset and the second offset being different. A registration between a tracking coordinate system for a physical space monitored by tracking sensors and an image coordinate system for the first and second images from the fluoroscopic x-ray imaging system is provided based on the indications of the first and second offsets.

Other methods and related systems, and corresponding methods and computer program products according to embodiments of the inventive subject matter will be or become apparent to one with skill in the art upon review of the following drawings and detailed description. It is intended that all such systems, and corresponding methods and computer program products be included within this description, be within the scope of the present inventive subject matter and be protected by the accompanying claims. Moreover, it is intended that all embodiments disclosed herein can be implemented separately or combined in any way and/or combination.

DESCRIPTION OF THE DRAWINGS

The accompanying drawings, which are included to provide a further understanding of the disclosure and are incorporated in and constitute a part of this application, illustrate certain non-limiting embodiments of inventive concepts. In the drawings:

FIGS. 7A-7C illustrate an end-effector in accordance with an exemplary embodiment;

FIG. 13A illustrates a portion of a robot including the robot arm and an end-effector in accordance with an exemplary embodiment;

FIG. 13B is a close-up view of the end-effector, with a plurality of tracking markers rigidly affixed thereon, shown in FIG. 13A;

FIG. 13C is a tool or instrument with a plurality of tracking markers rigidly affixed thereon according to one embodiment;

FIGS. 27A, 27B, and 27C are photographs illustrating fixtures that may be used for calibration according to some embodiments of inventive concepts;

FIGS. 29A, 29B, and 29C are photographs illustrating use of BBs/fiducials in a fixture to provide top-bottom/left-right collimation according to some embodiments of inventive concepts;

FIG. 37 is a flow chart illustrating operations of a robotic system according to some embodiments of inventive concepts;

FIG. 39 is a plan view of a fluoroscopic x-ray imaging system including mounting sockets for a fixture according to some embodiments of inventive concepts;

FIG. 40 is a plan view of a fixture mounted on an x-ray detector of a fluoroscopic x-ray imaging system according to some embodiments of inventive concepts;

FIG. 41 is a plan view of a fixture and a temporary x-ray opaque fiducial pattern mounted on an x-ray detector of a fluoroscopic x-ray imaging system according to some embodiments of inventive concepts;

FIGS. 45A, 45B, and 45C are enlarged plan views illustrating a fixture mounted on an x-ray detector of a fluoroscopic imaging system, a sterile drape covering the fixture and the x-ray detector, and application of tracking markers over/through the sterile drape according to some embodiments of inventive concepts.

DETAILED DESCRIPTION

Figure 1:
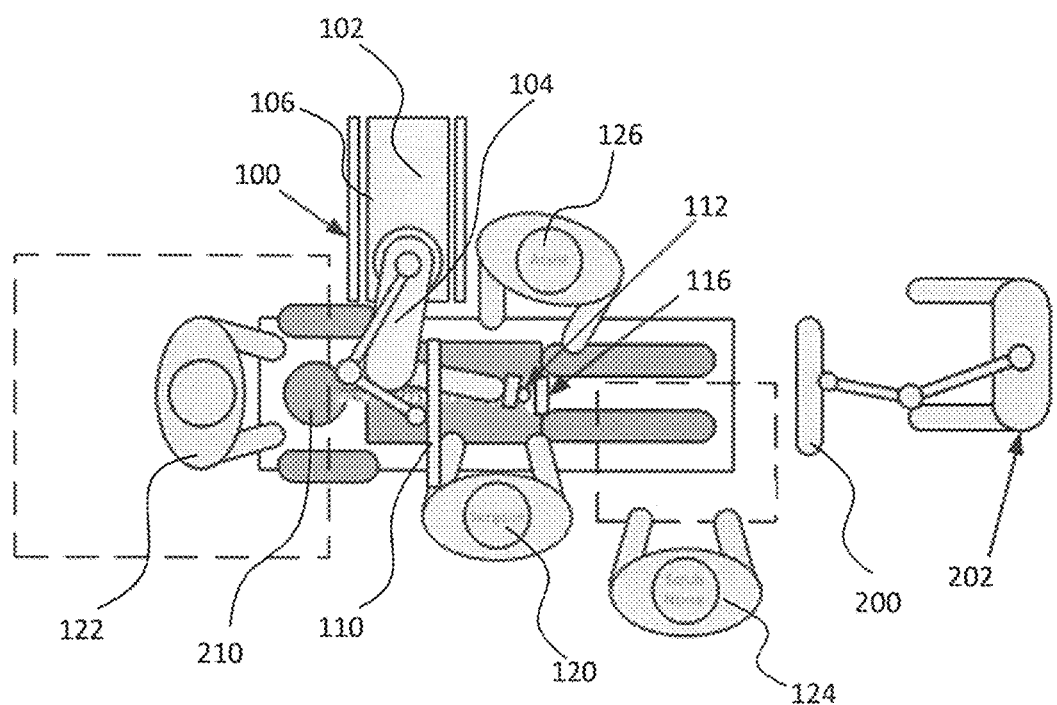
FIG. 1 is an overhead view of a potential arrangement for locations of the robotic system, patient, surgeon, and other medical personnel during a surgical procedure.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 2:
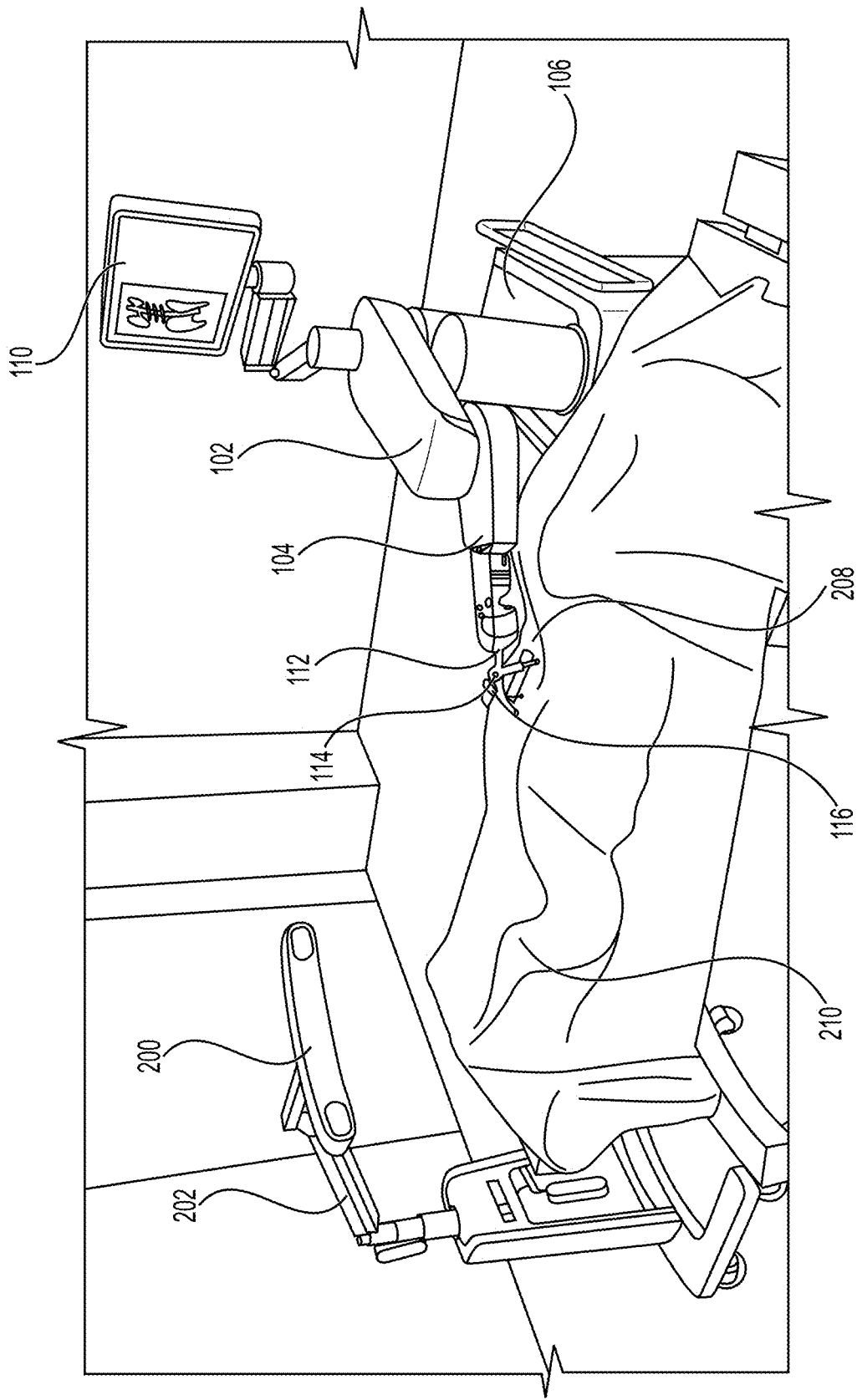
FIG. 2 illustrates the robotic system including positioning of the surgical robot and the camera relative to the patient according to one embodiment.

Turning now to the drawing, FIGS. 1 and 2 illustrate a surgical robot system 100 in accordance with an exemplary embodiment. Surgical robot system 100 may include, for example, a surgical robot 102, one or more robot arms 104, a base 106, a display 110, an end-effector 112, for example, including a guide tube 114, and one or more tracking markers 118. The surgical robot system 100 may include a patient tracking device 116 also including one or more tracking markers 118, which is adapted to be secured directly to the patient 210 (e.g., to a bone of the patient 210). The surgical robot system 100 may also use a camera 200, for example, positioned on a camera stand 202. The camera stand 202 can have any suitable configuration to move, orient, and support the camera 200 in a desired position. The camera 200 may include any suitable camera or cameras, such as one or more infrared cameras (e.g., bifocal or stereophotogrammetric cameras), able to identify, for example, active and passive tracking markers 118 (shown as part of patient tracking device 116 in FIG. 2 and shown by enlarged view in FIGS. 13A-13B) in a given measurement volume viewable from the perspective of the camera 200. The camera 200 may scan the given measurement volume and detect the light that comes from the markers 118 in order to identify and determine the position of the markers 118 in three-dimensions. For example, active markers 118 may include infrared-emitting markers that are activated by an electrical signal (e.g., infrared light emitting diodes (LEDs)), and/or passive markers 118 may include retro-reflective markers that reflect infrared light (e.g., they reflect incoming IR radiation into the direction of the incoming light), for example, emitted by illuminators on the camera 200 or other suitable device.

FIGS. 1 and 2 illustrate a potential configuration for the placement of the surgical robot system 100 in an operating room environment. For example, the robot 102 may be positioned near or next to patient 210. Although depicted near the head of the patient 210, it will be appreciated that the robot 102 can be positioned at any suitable location near the patient 210 depending on the area of the patient 210 undergoing the operation. The camera 200 may be separated from the robot system 100 and positioned at the foot of patient 210. This location allows the camera 200 to have a direct visual line of sight to the surgical field 208. Again, it is contemplated that the camera 200 may be located at any suitable position having line of sight to the surgical field 208. In the configuration shown, the surgeon 120 may be positioned across from the robot 102, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. The traditional areas for the anesthesiologist 122 and the nurse or scrub tech 124 may remain unimpeded by the locations of the robot 102 and camera 200.

With respect to the other components of the robot 102, the display 110 can be attached to the surgical robot 102 and in other exemplary embodiments, display 110 can be detached from surgical robot 102, either within a surgical room with the surgical robot 102, or in a remote location. End-effector 112 may be coupled to the robot arm 104 and controlled by at least one motor. In exemplary embodiments, end-effector 112 can comprise a guide tube 114, which is able to receive and orient a surgical instrument 608 (described further herein) used to perform surgery on the patient 210. As used herein, the term "end-effector" is used interchangeably with the terms "end-effectuator" and "effectuator element." Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument 608 in a desired manner.

The surgical robot 102 is able to control the translation and orientation of the end-effector 112. The robot 102 is able to move end-effector 112 along x-, y-, and z-axes, for example. The end-effector 112 can be configured for selective rotation about one or more of the x-, y-, and z-axis, and a Z Frame axis (such that one or more of the Euler Angles (e.g., roll, pitch, and/or yaw) associated with end-effector 112 can be selectively controlled). In some exemplary embodiments, selective control of the translation and orientation of end-effector 112 can permit performance of medical procedures with significantly improved accuracy compared to conventional robots that use, for example, a six degree of freedom robot arm comprising only rotational axes. For example, the surgical robot system 100 may be used to operate on patient 210, and robot arm 104 can be positioned above the body of patient 210, with end-effector 112 selectively angled relative to the z-axis toward the body of patient 210.

In some exemplary embodiments, the position of the surgical instrument 608 can be dynamically updated so that surgical robot 102 can be aware of the location of the surgical instrument 608 at all times during the procedure. Consequently, in some exemplary embodiments, surgical robot 102 can move the surgical instrument 608 to the desired position quickly without any further assistance from a physician (unless the physician so desires). In some further embodiments, surgical robot 102 can be configured to correct the path of the surgical instrument 608 if the surgical instrument 608 strays from the selected, preplanned trajectory. In some exemplary embodiments, surgical robot 102 can be configured to permit stoppage, modification, and/or manual control of the movement of end-effector 112 and/or the surgical instrument 608. Thus, in use, in exemplary embodiments, a physician or other user can operate the system 100, and has the option to stop, modify, or manually control the autonomous movement of end-effector 112 and/or the surgical instrument 608. Further details of surgical robot system 100 including the control and movement of a surgical instrument 608 by surgical robot 102 can be found in co-pending U.S. Pat. No. 9,782,229, the disclosure of which is hereby incorporated herein by reference in its entirety.

The robotic surgical system 100 can comprise one or more tracking markers 118 configured to track the movement of robot arm 104, end-effector 112, patient 210, and/or the surgical instrument 608 in three dimensions. In exemplary embodiments, a plurality of tracking markers 118 can be mounted (or otherwise secured) thereon to an outer surface of the robot 102, such as, for example and without limitation, on base 106 of robot 102, on robot arm 104, and/or on the end-effector 112. In exemplary embodiments, at least one tracking marker 118 of the plurality of tracking markers 118 can be mounted or otherwise secured to the end-effector 112. One or more tracking markers 118 can further be mounted (or otherwise secured) to the patient 210. In exemplary embodiments, the plurality of tracking markers 118 can be positioned on the patient 210 spaced apart from the surgical field 208 to reduce the likelihood of being obscured by the surgeon, surgical tools, or other parts of the robot 102. Further, one or more tracking markers 118 can be further mounted (or otherwise secured) to the surgical tools 608 (e.g., a screwdriver, dilator, implant inserter, or the like). Thus, the tracking markers 118 enable each of the marked objects (e.g., the end-effector 112, the patient 210, and the surgical tools 608) to be tracked by the robot 102. In exemplary embodiments, system 100 can use tracking information collected from each of the marked objects to calculate the orientation and location, for example, of the end-effector 112, the surgical instrument 608 (e.g., positioned in the tube 114 of the end-effector 112), and the relative position of the patient 210.

The markers 118 may include radiopaque or optical markers. The markers 118 may be suitably shaped include spherical, spheroid, cylindrical, cube, cuboid, or the like. In exemplary embodiments, one or more of markers 118 may be optical markers. In some embodiments, the positioning of one or more tracking markers 118 on end-effector 112 may increase/maximize accuracy of positional measurements by serving to check or verify a position of end-effector 112. Further details of surgical robot system 100 including the control, movement and tracking of surgical robot 102 and of a surgical instrument 608 can be found in U.S. patent publication No. 2016/0242849, the disclosure of which is incorporated herein by reference in its entirety.

Exemplary embodiments include one or more markers 118 coupled to the surgical instrument 608. In exemplary embodiments, these markers 118, for example, coupled to the patient 210 and surgical instruments 608, as well as markers 118 coupled to the end-effector 112 of the robot 102 can comprise conventional infrared light-emitting diodes (LEDs) or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 118 can comprise conventional reflective spheres capable of being tracked using a commercially available optical tracking system such as Polaris Spectra. Polaris Spectra is also a registered trademark of Northern Digital, Inc. In an exemplary embodiment, the markers 118 coupled to the end-effector 112 are active markers which comprise infrared light-emitting diodes which may be turned on and off, and the markers 118 coupled to the patient 210 and the surgical instruments 608 comprise passive reflective spheres.

In exemplary embodiments, light emitted from and/or reflected by markers 118 can be detected by camera 200 and can be used to monitor the location and movement of the marked objects. In alternative embodiments, markers 118 can comprise a radio-frequency and/or electromagnetic reflector or transceiver and the camera 200 can include or be replaced by a radio-frequency and/or electromagnetic transceiver.

Figure 3:
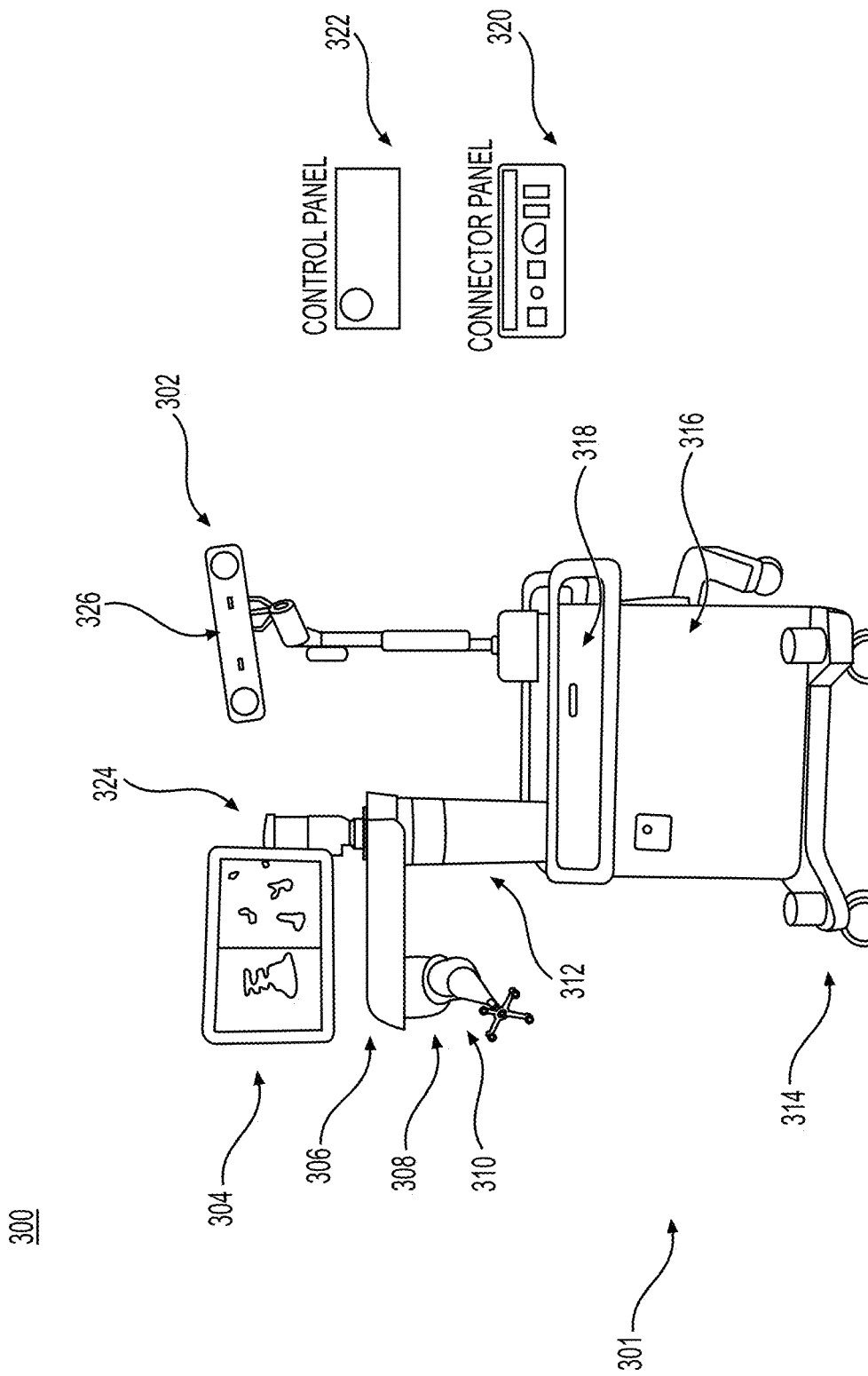
FIG. 3 illustrates a surgical robotic system in accordance with an exemplary embodiment.

Similar to surgical robot system 100, FIG. 3 illustrates a surgical robot system 300 and camera stand 302, in a docked configuration, consistent with an exemplary embodiment of the present disclosure. Surgical robot system 300 may comprise a robot 301 including a display 304, upper arm 306, lower arm 308, end-effector 310, vertical column 312, casters 314, cabinet 316, tablet drawer 318, connector panel 320, control panel 322, and ring of information 324. Camera stand 302 may comprise camera 326. These components are described in greater with respect to FIG. 5. FIG. 3 illustrates the surgical robot system 300 in a docked configuration where the camera stand 302 is nested with the robot 301, for example, when not in use. It will be appreciated by those skilled in the art that the camera 326 and robot 301 may be separated from one another and positioned at any appropriate location during the surgical procedure, for example, as shown in FIGS. 1 and 2.

Figure 4:
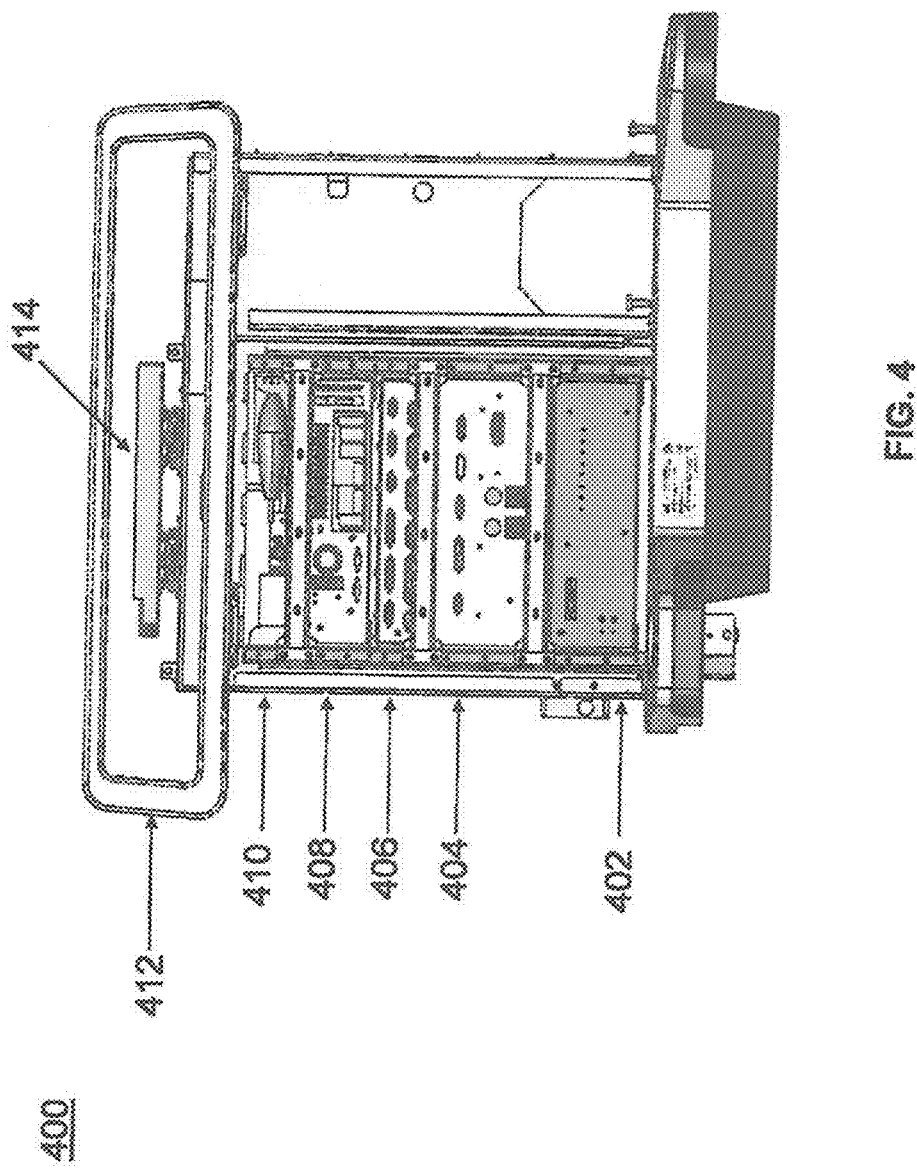
FIG. 4 illustrates a portion of a surgical robot in accordance with an exemplary embodiment.

FIG. 4 illustrates a base 400 consistent with an exemplary embodiment of the present disclosure. Base 400 may be a portion of surgical robot system 300 and comprise cabinet 316. Cabinet 316 may house certain components of surgical robot system 300 including but not limited to a battery 402, a power distribution module 404, a platform interface board module 406, a computer 408, a handle 412, and a tablet drawer 414. The connections and relationship between these components is described in greater detail with respect to FIG. 5.

Figure 5:
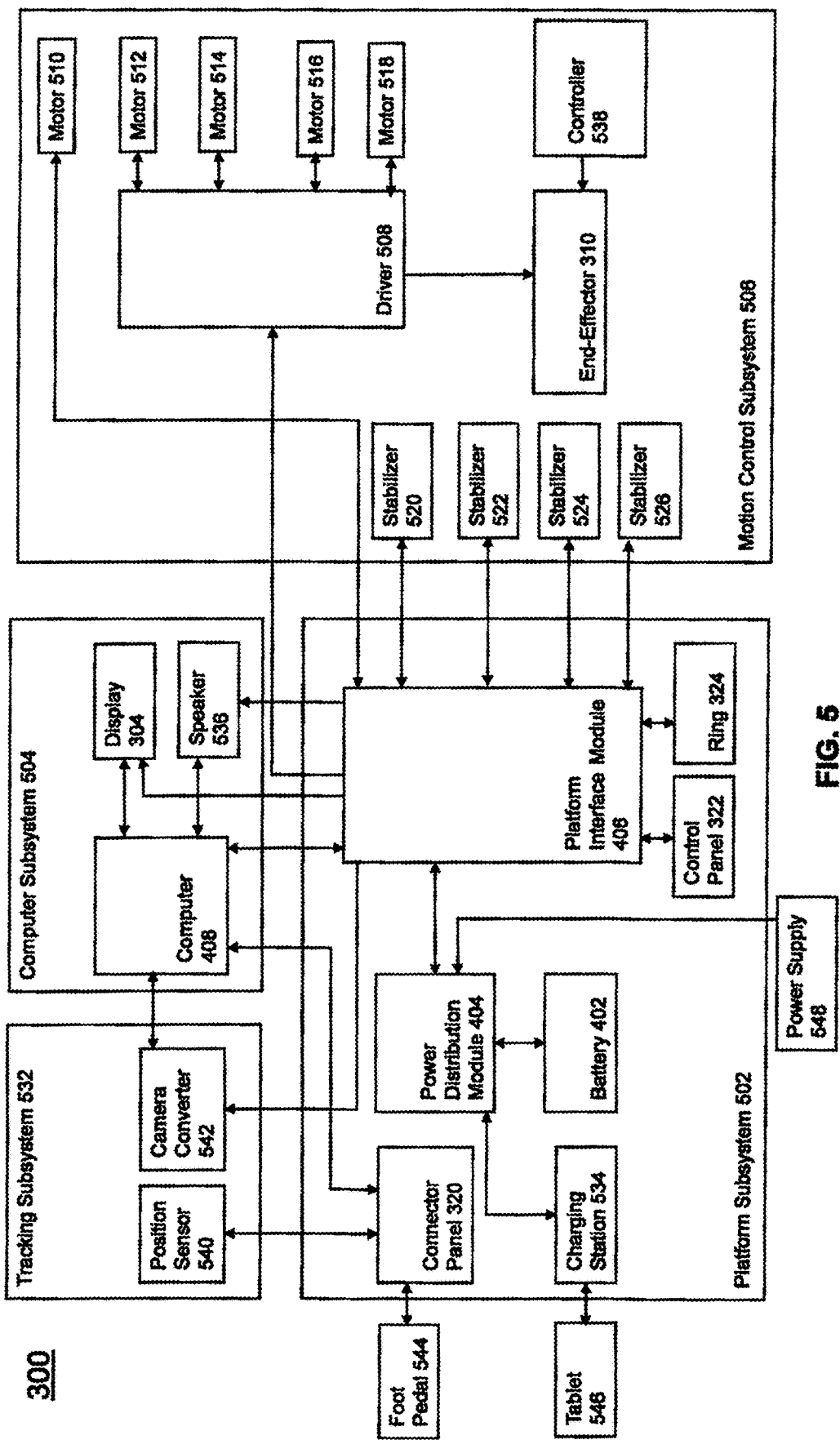
FIG. 5 illustrates a block diagram of a surgical robot in accordance with an exemplary embodiment.

FIG. 5 illustrates a block diagram of certain components of an exemplary embodiment of surgical robot system 300. Surgical robot system 300 may comprise platform subsystem 502, computer subsystem 504, motion control subsystem 506, and tracking subsystem 532. Platform subsystem 502 may further comprise battery 402, power distribution module 404, platform interface board module 406, and tablet charging station 534. Computer subsystem 504 may further comprise computer 408, display 304, and speaker 536. Motion control subsystem 506 may further comprise driver circuit 508, motors 510, 512, 514, 516, 518, stabilizers 520, 522, 524, 526, end-effector 310, and controller 538. Tracking subsystem 532 may further comprise position sensor 540 and camera converter 542. System 300 may also comprise a foot pedal 544 and tablet 546.

Input power is supplied to system 300 via a power source 548 which may be provided to power distribution module 404. Power distribution module 404 receives input power and is configured to generate different power supply voltages that are provided to other modules, components, and subsystems of system 300. Power distribution module 404 may be configured to provide different voltage supplies to platform interface module 406, which may be provided to other components such as computer 408, display 304, speaker 536, driver 508 to, for example, power motors 512, 514, 516, 518 and end-effector 310, motor 510, ring 324, camera converter 542, and other components for system 300 for example, fans for cooling the electrical components within cabinet 316.

Power distribution module 404 may also provide power to other components such as tablet charging station 534 that may be located within tablet drawer 318. Tablet charging station 534 may be in wireless or wired communication with tablet 546 for charging table 546. Tablet 546 may be used by a surgeon consistent with the present disclosure and described herein.

Power distribution module 404 may also be connected to battery 402, which serves as temporary power source in the event that power distribution module 404 does not receive power from input power 548. At other times, power distribution module 404 may serve to charge battery 402 if necessary.

Other components of platform subsystem 502 may also include connector panel 320, control panel 322, and ring 324. Connector panel 320 may serve to connect different devices and components to system 300 and/or associated components and modules. Connector panel 320 may contain one or more ports that receive lines or connections from different components. For example, connector panel 320 may have a ground terminal port that may ground system 300 to other equipment, a port to connect foot pedal 544 to system 300, a port to connect to tracking subsystem 532, which may comprise position sensor 540, camera converter 542, and cameras 326 associated with camera stand 302. Connector panel 320 may also include other ports to allow USB, Ethernet, HDMI communications to other components, such as computer 408.

Control panel 322 may provide various buttons or indicators that control operation of system 300 and/or provide information regarding system 300. For example, control panel 322 may include buttons to power on or off system 300, lift or lower vertical column 312, and lift or lower stabilizers 520-526 that may be designed to engage casters 314 to lock system 300 from physically moving. Other buttons may stop system 300 in the event of an emergency, which may remove all motor power and apply mechanical brakes to stop all motion from occurring. Control panel 322 may also have indicators notifying the user of certain system conditions such as a line power indicator or status of charge for battery 402.

Ring 324 may be a visual indicator to notify the user of system 300 of different modes that system 300 is operating under and certain warnings to the user.

Computer subsystem 504 includes computer 408, display 304, and speaker 536. Computer 504 includes an operating system and software to operate system 300. Computer 504 may receive and process information from other components (for example, tracking subsystem 532, platform subsystem 502, and/or motion control subsystem 506) in order to display information to the user. Further, computer subsystem 504 may also include speaker 536 to provide audio to the user.

Tracking subsystem 532 may include position sensor 504 and converter 542. Tracking subsystem 532 may correspond to camera stand 302 including camera 326 as described with respect to FIG. 3. Position sensor 504 may be camera 326. Tracking subsystem may track the location of certain markers that are located on the different components of system 300 and/or instruments used by a user during a surgical procedure. This tracking may be conducted in a manner consistent with the present disclosure including the use of infrared technology that tracks the location of active or passive elements, such as LEDs or reflective markers, respectively. The location, orientation, and position of structures having these types of markers may be provided to computer 408 which may be shown to a user on display 304. For example, a surgical instrument 608 having these types of markers and tracked in this manner (which may be referred to as a navigational space) may be shown to a user in relation to a three dimensional image of a patient's anatomical structure.

Motion control subsystem 506 may be configured to physically move vertical column 312, upper arm 306, lower arm 308, or rotate end-effector 310. The physical movement may be conducted through the use of one or more motors 510-518. For example, motor 510 may be configured to vertically lift or lower vertical column 312. Motor 512 may be configured to laterally move upper arm 308 around a point of engagement with vertical column 312 as shown in FIG. 3. Motor 514 may be configured to laterally move lower arm 308 around a point of engagement with upper arm 308 as shown in FIG. 3. Motors 516 and 518 may be configured to move end-effector 310 in a manner such that one may control the roll and one may control the tilt, thereby providing multiple angles that end-effector 310 may be moved. These movements may be achieved by controller 538 which may control these movements through load cells disposed on end-effector 310 and activated by a user engaging these load cells to move system 300 in a desired manner.

Moreover, system 300 may provide for automatic movement of vertical column 312, upper arm 306, and lower arm 308 through a user indicating on display 304 (which may be a touchscreen input device) the location of a surgical instrument or component on a three dimensional image of the patient's anatomy on display 304. The user may initiate this automatic movement by stepping on foot pedal 544 or some other input means.

Figure 6:
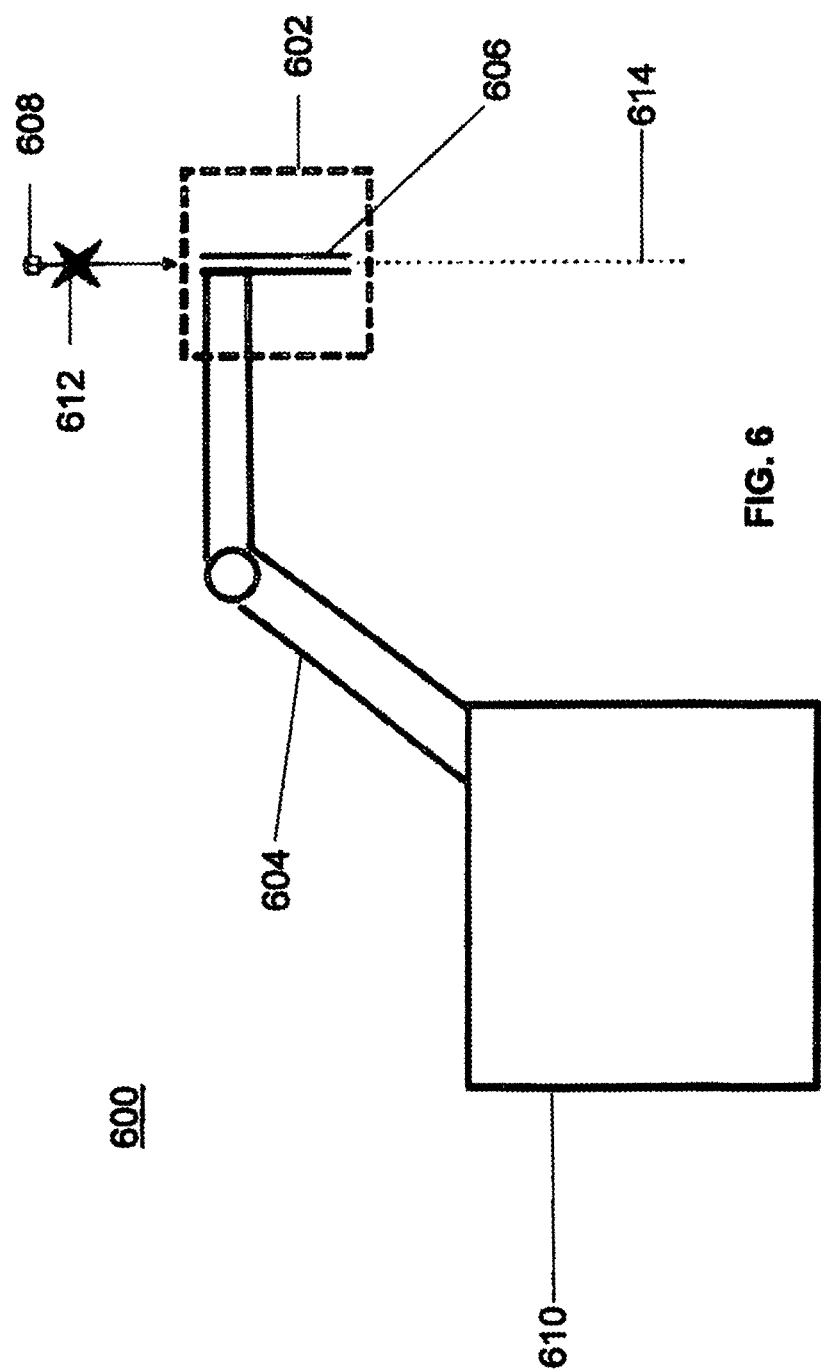
FIG. 6 illustrates a surgical robot in accordance with an exemplary embodiment.

FIG. 6 illustrates a surgical robot system 600 consistent with an exemplary embodiment. Surgical robot system 600 may comprise end-effector 602, robot arm 604, guide tube 606, instrument 608, and robot base 610. Instrument tool 608 may be attached to a tracking array 612 including one or more tracking markers (such as markers 118) and have an associated trajectory 614. Trajectory 614 may represent a path of movement that instrument tool 608 is configured to travel once it is positioned through or secured in guide tube 606, for example, a path of insertion of instrument tool 608 into a patient. In an exemplary operation, robot base 610 may be configured to be in electronic communication with robot arm 604 and end-effector 602 so that surgical robot system 600 may assist a user (for example, a surgeon) in operating on the patient 210. Surgical robot system 600 may be consistent with previously described surgical robot system 100 and 300.

Figure 8:
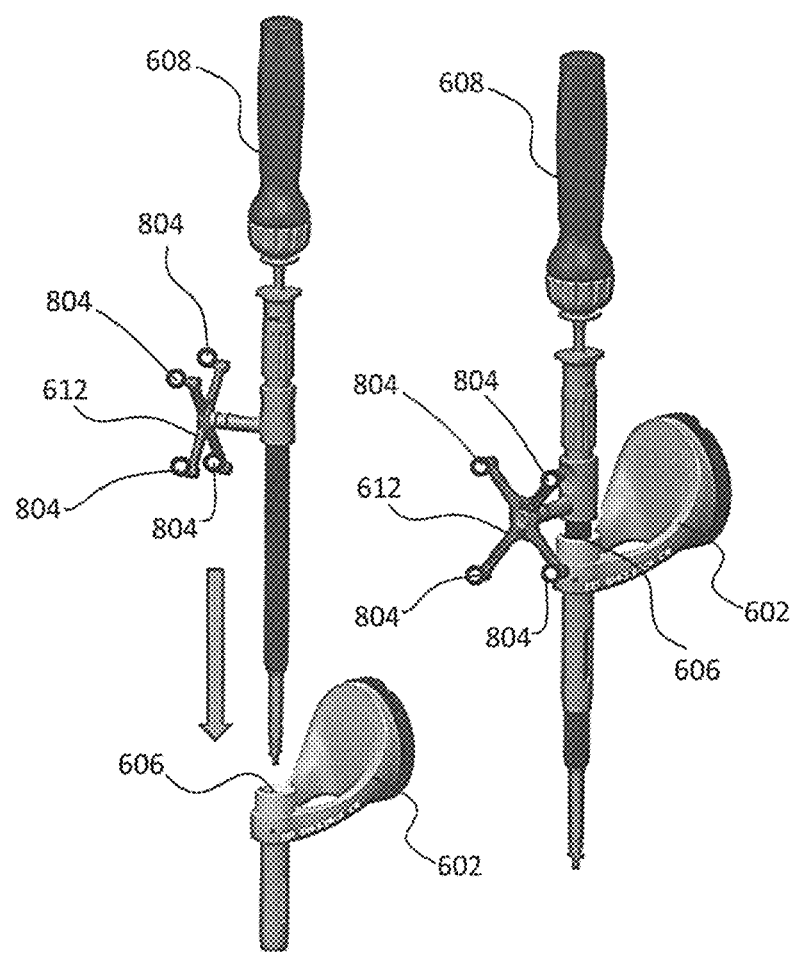
FIG. 8 illustrates a surgical instrument and the end-effector, before and after, inserting the surgical instrument into the guide tube of the end-effector according to one embodiment.

A tracking array 612 may be mounted on instrument 608 to monitor the location and orientation of instrument tool 608. The tracking array 612 may be attached to an instrument 608 and may comprise tracking markers 804. As best seen in FIG. 8, tracking markers 804 may be, for example, light emitting diodes and/or other types of reflective markers (e.g., markers 118 as described elsewhere herein). The tracking devices may be one or more line of sight devices associated with the surgical robot system. As an example, the tracking devices may be one or more cameras 200, 326 associated with the surgical robot system 100, 300 and may also track tracking array 612 for a defined domain or relative orientations of the instrument 608 in relation to the robot arm 604, the robot base 610, end-effector 602, and/or the patient 210. The tracking devices may be consistent with those structures described in connection with camera stand 302 and tracking subsystem 532.

FIGS. 7A, 7B, and 7C illustrate a top view, front view, and side view, respectively, of end-effector 602 consistent with an exemplary embodiment. End-effector 602 may comprise one or more tracking markers 702. Tracking markers 702 may be light emitting diodes or other types of active and passive markers, such as tracking markers 118 that have been previously described. In an exemplary embodiment, the tracking markers 702 are active infrared-emitting markers that are activated by an electrical signal (e.g., infrared light emitting diodes (LEDs)). Thus, tracking markers 702 may be activated such that the infrared markers 702 are visible to the camera 200, 326 or may be deactivated such that the infrared markers 702 are not visible to the camera 200, 326. Thus, when the markers 702 are active, the end-effector 602 may be controlled by the system 100, 300, 600, and when the markers 702 are deactivated, the end-effector 602 may be locked in position and unable to be moved by the system 100, 300, 600.

Markers 702 may be disposed on or within end-effector 602 in a manner such that the markers 702 are visible by one or more cameras 200, 326 or other tracking devices associated with the surgical robot system 100, 300, 600. The camera 200, 326 or other tracking devices may track end-effector 602 as it moves to different positions and viewing angles by following the movement of tracking markers 702. The location of markers 702 and/or end-effector 602 may be shown on a display 110, 304 associated with the surgical robot system 100, 300, 600, for example, display 110 as shown in FIG. 2 and/or display 304 shown in FIG. 3. This display 110, 304 may allow a user to ensure that end-effector 602 is in a desirable position in relation to robot arm 604, robot base 610, the patient 210, and/or the user.

For example, as shown in FIG. 7A, markers 702 may be placed around the surface of end-effector 602 so that a tracking device placed away from the surgical field 208 and facing toward the robot 102, 301 and the camera 200, 326 is able to view at least 3 of the markers 702 through a range of common orientations of the end-effector 602 relative to the tracking device. For example, distribution of markers 702 in this way allows end-effector 602 to be monitored by the tracking devices when end-effector 602 is translated and rotated in the surgical field 208.

In addition, in exemplary embodiments, end-effector 602 may be equipped with infrared (IR) receivers that can detect when an external camera 200, 326 is getting ready to read markers 702. Upon this detection, end-effector 602 may then illuminate markers 702. The detection by the IR receivers that the external camera 200, 326 is ready to read markers 702 may signal the need to synchronize a duty cycle of markers 702, which may be light emitting diodes, to an external camera 200, 326. This may also allow for lower power consumption by the robotic system as a whole, whereby markers 702 would only be illuminated at the appropriate time instead of being illuminated continuously. Further, in exemplary embodiments, markers 702 may be powered off to prevent interference with other navigation tools, such as different types of surgical instruments 608.

FIG. 8 depicts one type of surgical instrument 608 including a tracking array 612 and tracking markers 804. Tracking markers 804 may be of any type described herein including but not limited to light emitting diodes or reflective spheres. Markers 804 are monitored by tracking devices associated with the surgical robot system 100, 300, 600 and may be one or more of the line of sight cameras 200, 326. The cameras 200, 326 may track the location of instrument 608 based on the position and orientation of tracking array 612 and markers 804. A user, such as a surgeon 120, may orient instrument 608 in a manner so that tracking array 612 and markers 804 are sufficiently recognized by the tracking device or camera 200, 326 to display instrument 608 and markers 804 on, for example, display 110 of the exemplary surgical robot system.

The manner in which a surgeon 120 may place instrument 608 into guide tube 606 of the end-effector 602 and adjust the instrument 608 is evident in FIG. 8. The hollow tube or guide tube 114, 606 of the end-effector 112, 310, 602 is sized and configured to receive at least a portion of the surgical instrument 608. The guide tube 114, 606 is configured to be oriented by the robot arm 104 such that insertion and trajectory for the surgical instrument 608 is able to reach a desired anatomical target within or upon the body of the patient 210. The surgical instrument 608 may include at least a portion of a generally cylindrical instrument. Although a screwdriver is exemplified as the surgical tool 608, it will be appreciated that any suitable surgical tool 608 may be positioned by the end-effector 602. By way of example, the surgical instrument 608 may include one or more of a guide wire, cannula, a retractor, a drill, a reamer, a screwdriver, an insertion tool, a removal tool, or the like. Although the hollow tube 114, 606 is generally shown as having a cylindrical configuration, it will be appreciated by those of skill in the art that the guide tube 114, 606 may have any suitable shape, size and configuration desired to accommodate the surgical instrument 608 and access the surgical site.

Figure 9:
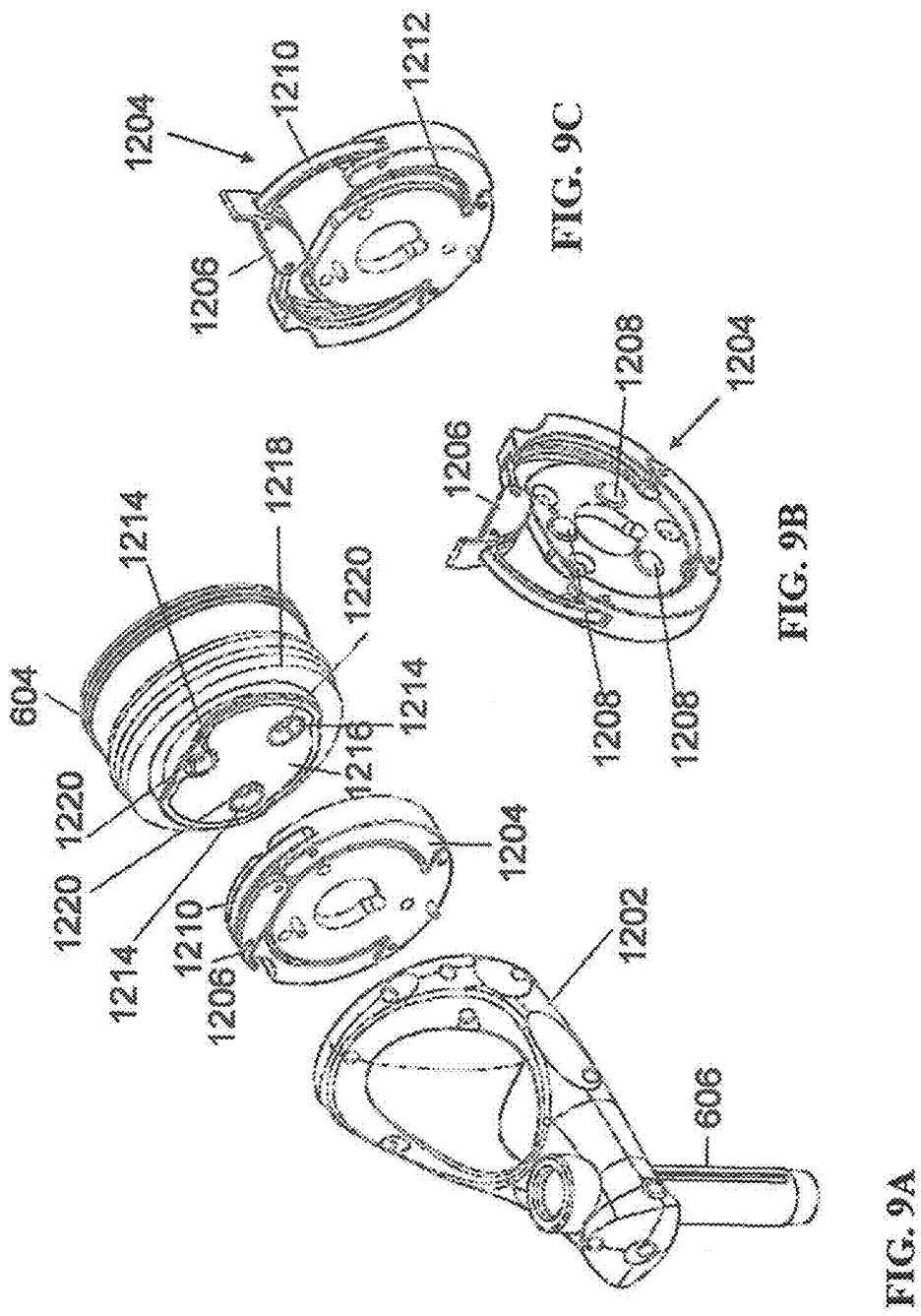
FIGS. 9A-9C illustrate portions of an end-effector and robot arm in accordance with an exemplary embodiment.

FIGS. 9A-9C illustrate end-effector 602 and a portion of robot arm 604 consistent with an exemplary embodiment. End-effector 602 may further comprise body 1202 and clamp 1204. Clamp 1204 may comprise handle 1206, balls 1208, spring 1210, and lip 1212. Robot arm 604 may further comprise depressions 1214, mounting plate 1216, lip 1218, and magnets 1220.

End-effector 602 may mechanically interface and/or engage with the surgical robot system and robot arm 604 through one or more couplings. For example, end-effector 602 may engage with robot arm 604 through a locating coupling and/or a reinforcing coupling. Through these couplings, end-effector 602 may fasten with robot arm 604 outside a flexible and sterile barrier. In an exemplary embodiment, the locating coupling may be a magnetically kinematic mount and the reinforcing coupling may be a five bar over center clamping linkage.

With respect to the locating coupling, robot arm 604 may comprise mounting plate 1216, which may be non-magnetic material, one or more depressions 1214, lip 1218, and magnets 1220. Magnet 1220 is mounted below each of depressions 1214. Portions of clamp 1204 may comprise magnetic material and be attracted by one or more magnets 1220. Through the magnetic attraction of clamp 1204 and robot arm 604, balls 1208 become seated into respective depressions 1214. For example, balls 1208 as shown in FIG. 9B would be seated in depressions 1214 as shown in FIG. 9A. This seating may be considered a magnetically-assisted kinematic coupling. Magnets 1220 may be configured to be strong enough to support the entire weight of end-effector 602 regardless of the orientation of end-effector 602. The locating coupling may be any style of kinematic mount that uniquely restrains six degrees of freedom.

With respect to the reinforcing coupling, portions of clamp 1204 may be configured to be a fixed ground link and as such clamp 1204 may serve as a five bar linkage. Closing clamp handle 1206 may fasten end-effector 602 to robot arm 604 as lip 1212 and lip 1218 engage clamp 1204 in a manner to secure end-effector 602 and robot arm 604. When clamp handle 1206 is closed, spring 1210 may be stretched or stressed while clamp 1204 is in a locked position. The locked position may be a position that provides for linkage past center. Because of a closed position that is past center, the linkage will not open absent a force applied to clamp handle 1206 to release clamp 1204. Thus, in a locked position, end-effector 602 may be robustly secured to robot arm 604.

Spring 1210 may be a curved beam in tension. Spring 1210 may be comprised of a material that exhibits high stiffness and high yield strain such as virgin PEEK (polyether-ether-ketone). The linkage between end-effector 602 and robot arm 604 may provide for a sterile barrier between end-effector 602 and robot arm 604 without impeding fastening of the two couplings.

The reinforcing coupling may be a linkage with multiple spring members. The reinforcing coupling may latch with a cam or friction based mechanism. The reinforcing coupling may also be a sufficiently powerful electromagnet that will support fastening end-effector 102 to robot arm 604. The reinforcing coupling may be a multi-piece collar completely separate from either end-effector 602 and/or robot arm 604 that slips over an interface between end-effector 602 and robot arm 604 and tightens with a screw mechanism, an over center linkage, or a cam mechanism.

Figure 10:
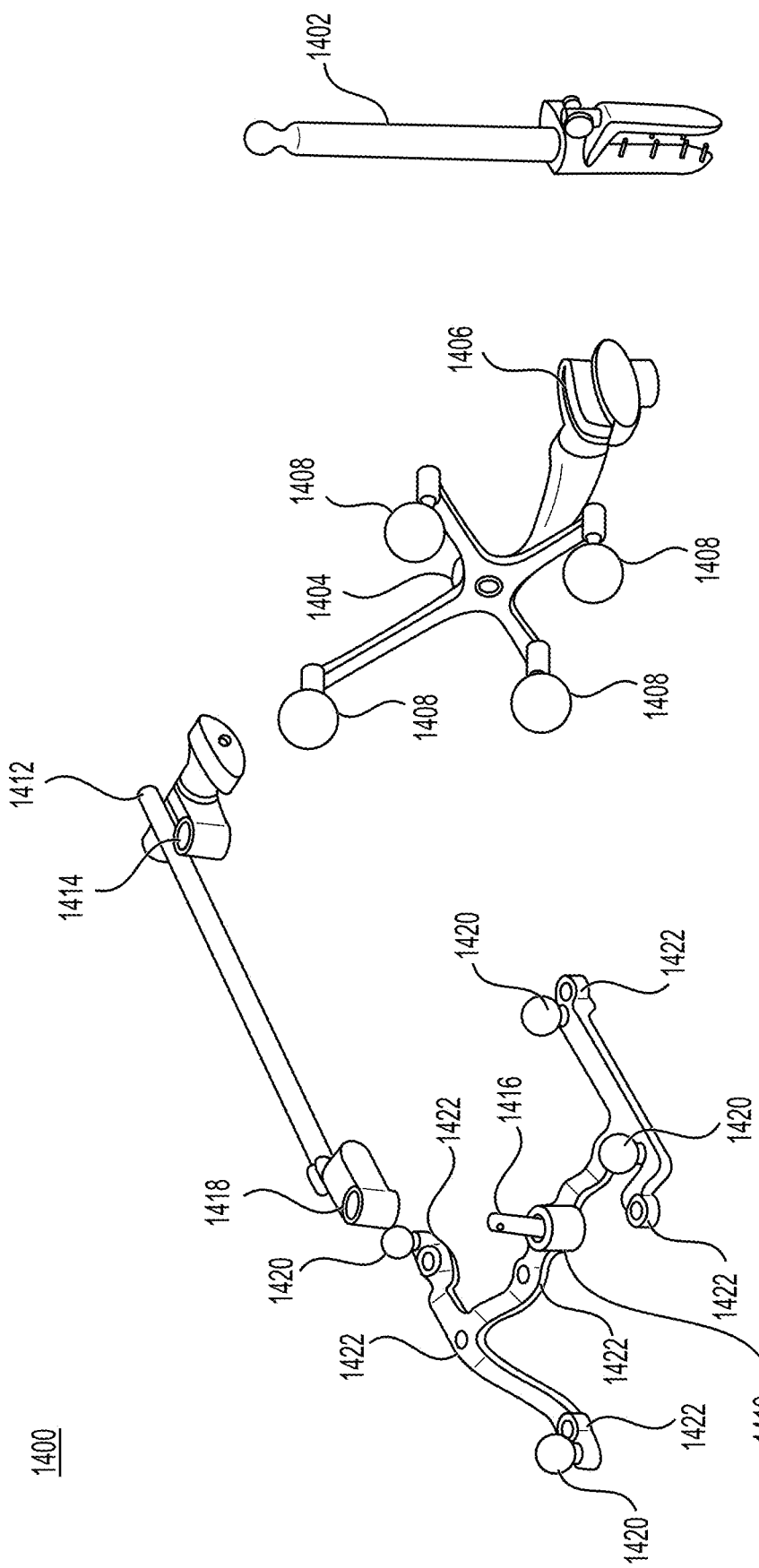
FIG. 10 illustrates a dynamic reference array, an imaging array, and other components in accordance with an exemplary embodiment.
Figure 11:
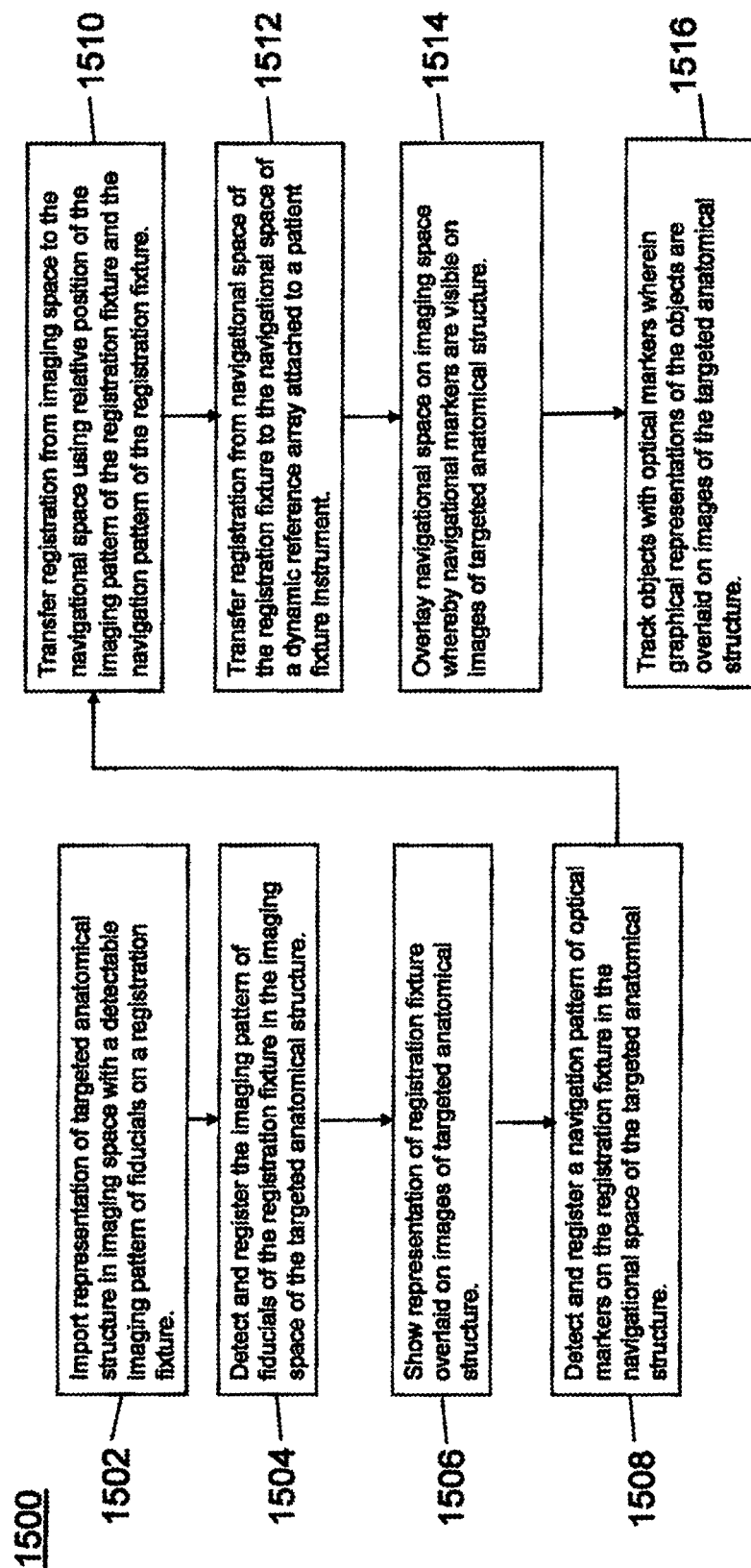
FIG. 11 illustrates a method of registration in accordance with an exemplary embodiment.

Referring to FIGS. 10 and 11, prior to or during a surgical procedure, certain registration procedures may be conducted to track objects and a target anatomical structure of the patient 210 both in a navigation space and an image space. To conduct such registration, a registration system 1400 may be used as illustrated in FIG. 10.

To track the position of the patient 210, a patient tracking device 116 may include a patient fixation instrument 1402 to be secured to a rigid anatomical structure of the patient 210 and a dynamic reference base (DRB) 1404 may be securely attached to the patient fixation instrument 1402. For example, patient fixation instrument 1402 may be inserted into opening 1406 of dynamic reference base 1404. Dynamic reference base 1404 may contain markers 1408 that are visible to tracking devices, such as tracking subsystem 532. These markers 1408 may be optical markers or reflective spheres, such as tracking markers 118, as previously discussed herein.

Patient fixation instrument 1402 is attached to a rigid anatomy of the patient 210 and may remain attached throughout the surgical procedure. In an exemplary embodiment, patient fixation instrument 1402 is attached to a rigid area of the patient 210, for example, a bone that is located away from the targeted anatomical structure subject to the surgical procedure. In order to track the targeted anatomical structure, dynamic reference base 1404 is associated with the targeted anatomical structure through the use of a registration fixture that is temporarily placed on or near the targeted anatomical structure in order to register the dynamic reference base 1404 with the location of the targeted anatomical structure.

A registration fixture 1410 is attached to patient fixation instrument 1402 through the use of a pivot arm 1412. Pivot arm 1412 is attached to patient fixation instrument 1402 by inserting patient fixation instrument 1402 through an opening 1414 of registration fixture 1410. Pivot arm 1412 is attached to registration fixture 1410 by, for example, inserting a knob 1416 through an opening 1418 of pivot arm 1412.

Using pivot arm 1412, registration fixture 1410 may be placed over the targeted anatomical structure and its location may be determined in an image space and navigation space using tracking markers 1420 and/or fiducials 1422 on registration fixture 1410. Registration fixture 1410 may contain a collection of markers 1420 that are visible in a navigational space (for example, markers 1420 may be detectable by tracking subsystem 532). Tracking markers 1420 may be optical markers visible in infrared light as previously described herein. Registration fixture 1410 may also contain a collection of fiducials 1422, for example, such as bearing balls, that are visible in an imaging space (for example, a three dimension CT image). As described in greater detail with respect to FIG. 11, using registration fixture 1410, the targeted anatomical structure may be associated with dynamic reference base 1404 thereby allowing depictions of objects in the navigational space to be overlaid on images of the anatomical structure. Dynamic reference base 1404, located at a position away from the targeted anatomical structure, may become a reference point thereby allowing removal of registration fixture 1410 and/or pivot arm 1412 from the surgical area.

FIG. 11 provides an exemplary method 1500 for registration consistent with the present disclosure. Method 1500 begins at step 1502 wherein a graphical representation (or image(s)) of the targeted anatomical structure may be imported into system 100, 300 600, for example computer 408. The graphical representation may be three dimensional CT or a fluoroscope scan of the targeted anatomical structure of the patient 210 which includes registration fixture 1410 and a detectable imaging pattern of fiducials 1420.

At step 1504, an imaging pattern of fiducials 1420 is detected and registered in the imaging space and stored in computer 408. Optionally, at this time at step 1506, a graphical representation of the registration fixture 1410 may be overlaid on the images of the targeted anatomical structure.

At step 1508, a navigational pattern of registration fixture 1410 is detected and registered by recognizing markers 1420. Markers 1420 may be optical markers that are recognized in the navigation space through infrared light by tracking subsystem 532 via position sensor 540. Thus, the location, orientation, and other information of the targeted anatomical structure is registered in the navigation space. Therefore, registration fixture 1410 may be recognized in both the image space through the use of fiducials 1422 and the navigation space through the use of markers 1420. At step 1510, the registration of registration fixture 1410 in the image space is transferred to the navigation space. This transferal is done, for example, by using the relative position of the imaging pattern of fiducials 1422 compared to the position of the navigation pattern of markers 1420.

At step 1512, registration of the navigation space of registration fixture 1410 (having been registered with the image space) is further transferred to the navigation space of dynamic registration array 1404 attached to patient fixture instrument 1402. Thus, registration fixture 1410 may be removed and dynamic reference base 1404 may be used to track the targeted anatomical structure in both the navigation and image space because the navigation space is associated with the image space.

At steps 1514 and 1516, the navigation space may be overlaid on the image space and objects with markers visible in the navigation space (for example, surgical instruments 608 with optical markers 804). The objects may be tracked through graphical representations of the surgical instrument 608 on the images of the targeted anatomical structure.

Figure 12A:
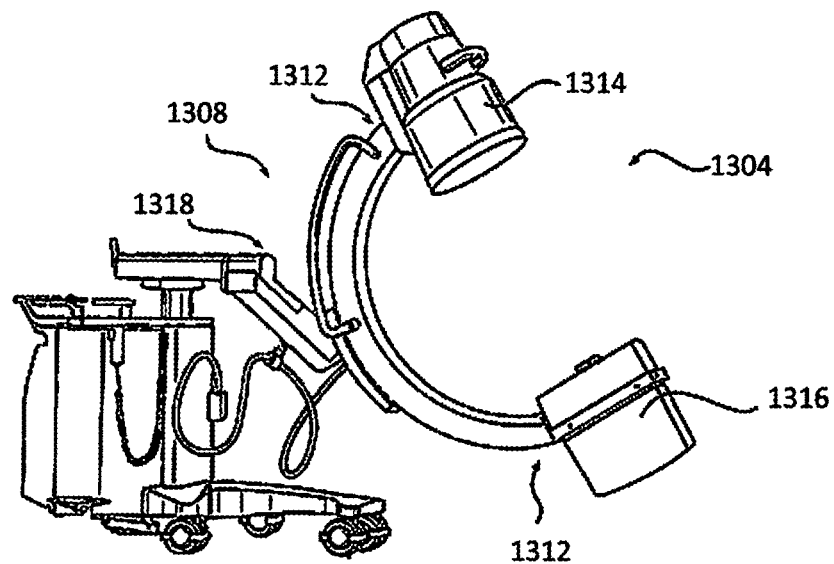
FIG. 12A-12B illustrate embodiments of imaging devices according to exemplary embodiments.
Figure 12B:
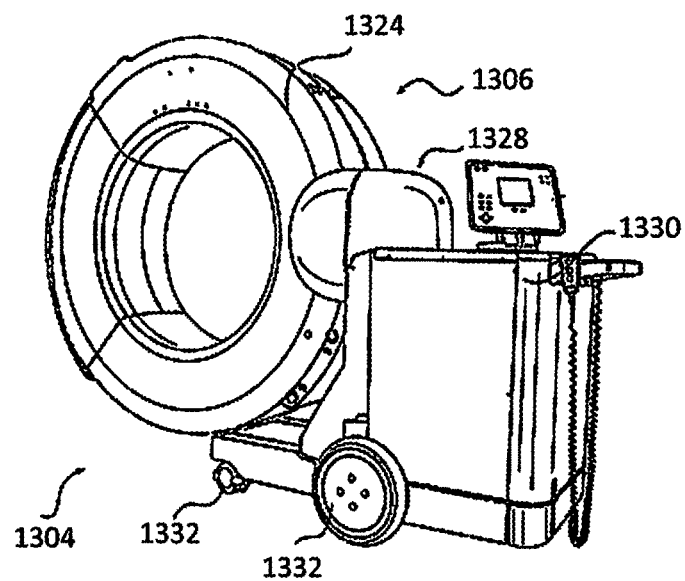

FIGS. 12A-12B illustrate imaging devices 1304 that may be used in conjunction with robot systems 100, 300, 600 to acquire pre-operative, intra-operative, post-operative, and/or real-time image data of patient 210. Any appropriate subject matter may be imaged for any appropriate procedure using the imaging system 1304. The imaging system 1304 may be any imaging device such as imaging device 1306 and/or a C-arm 1308 device. It may be desirable to take x-rays of patient 210 from a number of different positions, without the need for frequent manual repositioning of patient 210 which may be required in an x-ray system. As illustrated in FIG. 12A, the imaging system 1304 may be in the form of a C-arm 1308 that includes an elongated C-shaped member terminating in opposing distal ends 1312 of the "C" shape. C-shaped member 1130 may further comprise an x-ray source 1314 and an x-ray detector 1316 (also referred to as an image receptor). The space within C-arm 1308 of the arm may provide room for the physician to attend to the patient substantially free of interference from x-ray support structure 1318. As illustrated in FIG. 12B, the imaging system may include imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 210 to be acquired from multiple directions or in multiple planes. Although certain imaging systems 1304 are exemplified herein, it will be appreciated that any suitable imaging system may be selected by one of ordinary skill in the art.

Turning now to FIGS. 13A-13C, the surgical robot system 100, 300, 600 relies on accurate positioning of the end-effector 112, 602, surgical instruments 608, and/or the patient 210 (e.g., patient tracking device 116) relative to the desired surgical area. In the embodiments shown in FIGS. 13A-13C, the tracking markers 118, 804 are rigidly attached to a portion of the instrument 608 and/or end-effector 112.

FIG. 13A depicts part of the surgical robot system 100 with the robot 102 including base 106, robot arm 104, and end-effector 112. The other elements, not illustrated, such as the display, cameras, etc. may also be present as described herein. FIG. 13B depicts a close-up view of the end-effector 112 with guide tube 114 and a plurality of tracking markers 118 rigidly affixed to the end-effector 112. In this embodiment, the plurality of tracking markers 118 are attached to the guide tube 112. FIG. 13C depicts an instrument 608 (in this case, a probe 608A) with a plurality of tracking markers 804 rigidly affixed to the instrument 608. As described elsewhere herein, the instrument 608 could include any suitable surgical instrument, such as, but not limited to, guide wire, cannula, a retractor, a drill, a reamer, a screwdriver, an insertion tool, a removal tool, or the like.

When tracking an instrument 608, end-effector 112, or other object to be tracked in 3D, an array of tracking markers 118, 804 may be rigidly attached to a portion of the tool 608 or end-effector 112. Preferably, the tracking markers 118, 804 are attached such that the markers 118, 804 are out of the way (e.g., not impeding the surgical operation, visibility, etc.). The markers 118, 804 may be affixed to the instrument 608, end-effector 112, or other object to be tracked, for example, with an array 612. Usually three or four markers 118, 804 are used with an array 612. The array 612 may include a linear section, a cross piece, and may be asymmetric such that the markers 118, 804 are at different relative positions and locations with respect to one another. For example, as shown in FIG. 13C, a probe 608A with a 4-marker tracking array 612 is shown, and FIG. 13B depicts the end-effector 112 with a different 4-marker tracking array 612.

In FIG. 13C, the tracking array 612 functions as the handle 620 of the probe 608A. Thus, the four markers 804 are attached to the handle 620 of the probe 608A, which is out of the way of the shaft 622 and tip 624. Stereophotogrammetric tracking of these four markers 804 allows the instrument 608 to be tracked as a rigid body and for the tracking system 100, 300, 600 to precisely determine the position of the tip 624 and the orientation of the shaft 622 while the probe 608A is moved around in front of tracking cameras 200, 326.

To enable automatic tracking of one or more tools 608, end-effector 112, or other object to be tracked in 3D (e.g., multiple rigid bodies), the markers 118, 804 on each tool 608, end-effector 112, or the like, are arranged asymmetrically with a known inter-marker spacing. The reason for asymmetric alignment is so that it is unambiguous which marker 118, 804 corresponds to a particular location on the rigid body and whether markers 118, 804 are being viewed from the front or back, i.e., mirrored. For example, if the markers 118, 804 were arranged in a square on the tool 608 or end-effector 112, it would be unclear to the system 100, 300, 600 which marker 118, 804 corresponded to which corner of the square. For example, for the probe 608A, it would be unclear which marker 804 was closest to the shaft 622. Thus, it would be unknown which way the shaft 622 was extending from the array 612. Accordingly, each array 612 and thus each tool 608, end-effector 112, or other object to be tracked should have a unique marker pattern to allow it to be distinguished from other tools 608 or other objects being tracked. Asymmetry and unique marker patterns allow the system 100, 300, 600 to detect individual markers 118, 804 then to check the marker spacing against a stored template to determine which tool 608, end effector 112, or other object they represent. Detected markers 118, 804 can then be sorted automatically and assigned to each tracked object in the correct order. Without this information, rigid body calculations could not then be performed to extract key geometric information, for example, such as tool tip 624 and alignment of the shaft 622, unless the user manually specified which detected marker 118, 804 corresponded to which position on each rigid body. These concepts are commonly known to those skilled in the methods of 3D optical tracking.

Figures 14A, 14B:
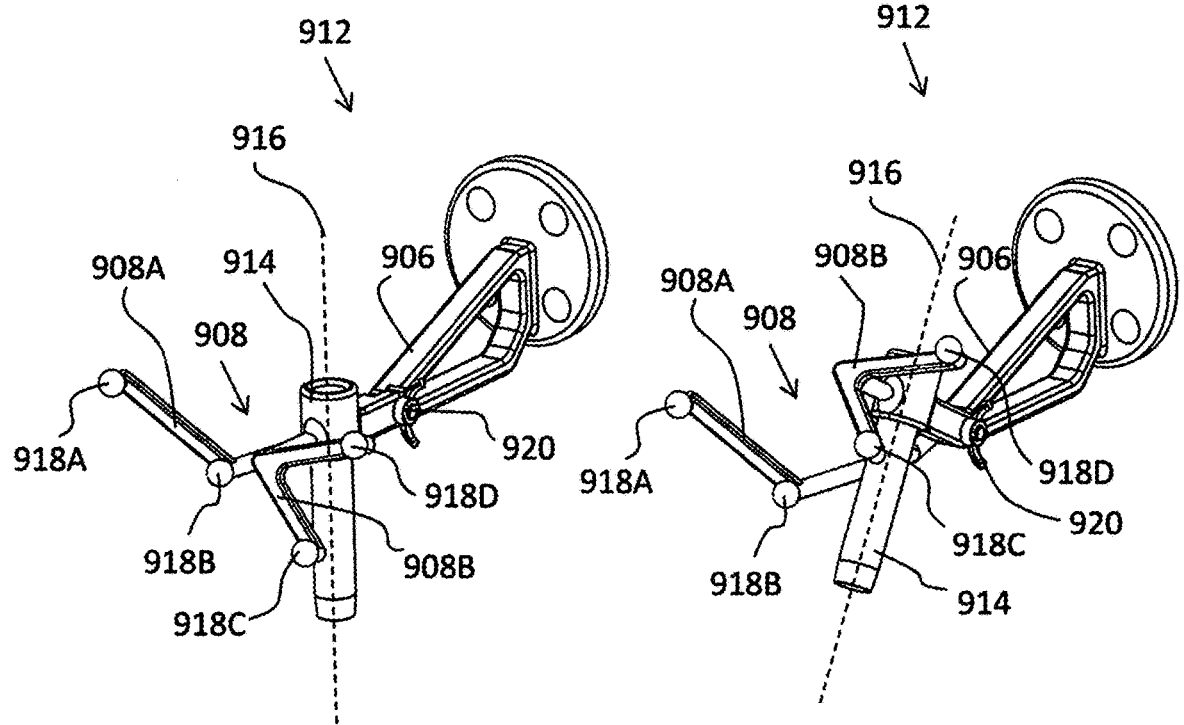
FIG. 14A is an alternative version of an end-effector with moveable tracking markers in a first configuration.
FIG. 14B is the end-effector shown in FIG. 14A with the moveable tracking markers in a second configuration.
Figure 14C:
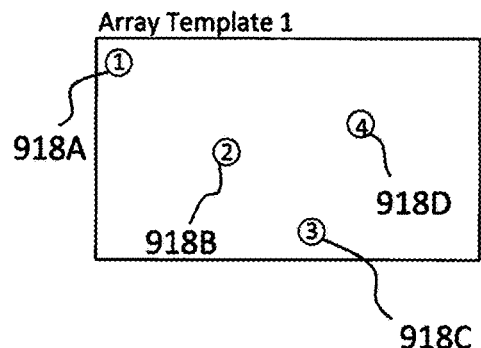
FIG. 14C shows the template of tracking markers in the first configuration from FIG. 14A.
Figure 14D:
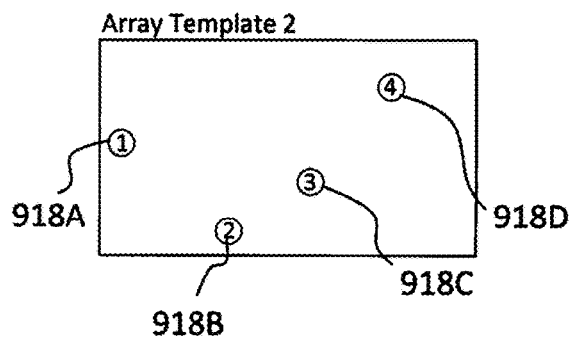
FIG. 14D shows the template of tracking markers in the second configuration from FIG. 14B.

Turning now to FIGS. 14A-14D, an alternative version of an end-effector 912 with moveable tracking markers 918A-918D is shown. In FIG. 14A, an array with moveable tracking markers 918A-918D are shown in a first configuration, and in FIG. 14B the moveable tracking markers 918A-918D are shown in a second configuration, which is angled relative to the first configuration. FIG. 14C shows the template of the tracking markers 918A-918D, for example, as seen by the cameras 200, 326 in the first configuration of FIG. 14A; and FIG. 14D shows the template of tracking markers 918A-918D, for example, as seen by the cameras 200, 326 in the second configuration of FIG. 14B.

In this embodiment, 4-marker array tracking is contemplated wherein the markers 918A-918D are not all in fixed position relative to the rigid body and instead, one or more of the array markers 918A-918D can be adjusted, for example, during testing, to give updated information about the rigid body that is being tracked without disrupting the process for automatic detection and sorting of the tracked markers 918A-918D.

When tracking any tool, such as a guide tube 914 connected to the end effector 912 of a robot system 100, 300, 600, the tracking array's primary purpose is to update the position of the end effector 912 in the camera coordinate system. When using the rigid system, for example, as shown in FIG. 13B, the array 612 of reflective markers 118 rigidly extend from the guide tube 114. Because the tracking markers 118 are rigidly connected, knowledge of the marker locations in the camera coordinate system also provides exact location of the centerline, tip, and tail of the guide tube 114 in the camera coordinate system. Typically, information about the position of the end effector 112 from such an array 612 and information about the location of a target trajectory from another tracked source are used to calculate the required moves that must be input for each axis of the robot 102 that will move the guide tube 114 into alignment with the trajectory and move the tip to a particular location along the trajectory vector.

Sometimes, the desired trajectory is in an awkward or unreachable location, but if the guide tube 114 could be swiveled, it could be reached. For example, a very steep trajectory pointing away from the base 106 of the robot 102 might be reachable if the guide tube 114 could be swiveled upward beyond the limit of the pitch (wrist up-down angle) axis, but might not be reachable if the guide tube 114 is attached parallel to the plate connecting it to the end of the wrist. To reach such a trajectory, the base 106 of the robot 102 might be moved or a different end effector 112 with a different guide tube attachment might be exchanged with the working end effector. Both of these solutions may be time consuming and cumbersome.

As best seen in FIGS. 14A and 14B, if the array 908 is configured such that one or more of the markers 918A-918D are not in a fixed position and instead, one or more of the markers 918A-918D can be adjusted, swiveled, pivoted, or moved, the robot 102 can provide updated information about the object being tracked without disrupting the detection and tracking process. For example, one of the markers 918A-918D may be fixed in position and the other markers 918A-918D may be moveable; two of the markers 918A-918D may be fixed in position and the other markers 918A-918D may be moveable; three of the markers 918A-918D may be fixed in position and the other marker 918A-918D may be moveable; or all of the markers 918A-918D may be moveable.

In the embodiment shown in FIGS. 14A and 14B, markers 918A, 918B are rigidly connected directly to a base 906 of the end-effector 912, and markers 918C, 918D are rigidly connected to the tube 914. Similar to array 612, array 908 may be provided to attach the markers 918A-918D to the end-effector 912, instrument 608, or other object to be tracked. In this case, however, the array 908 is comprised of a plurality of separate components. For example, markers 918A, 918B may be connected to the base 906 with a first array 908A, and markers 918C, 918D may be connected to the guide tube 914 with a second array 908B. Marker 918A may be affixed to a first end of the first array 908A and marker 918B may be separated a linear distance and affixed to a second end of the first array 908A. While first array 908 is substantially linear, second array 908B has a bent or V-shaped configuration, with respective root ends, connected to the guide tube 914, and diverging therefrom to distal ends in a V-shape with marker 918C at one distal end and marker 918D at the other distal end. Although specific configurations are exemplified herein, it will be appreciated that other asymmetric designs including different numbers and types of arrays 908A, 908B and different arrangements, numbers, and types of markers 918A-918D are contemplated.

The guide tube 914 may be moveable, swivelable, or pivotable relative to the base 906, for example, across a hinge 920 or other connector to the base 906. Thus, markers 918C, 918D are moveable such that when the guide tube 914 pivots, swivels, or moves, markers 918C, 918D also pivot, swivel, or move. As best seen in FIG. 14A, guide tube 914 has a longitudinal axis 916 which is aligned in a substantially normal or vertical orientation such that markers 918A-918D have a first configuration. Turning now to FIG. 14B, the guide tube 914 is pivoted, swiveled, or moved such that the longitudinal axis 916 is now angled relative to the vertical orientation such that markers 918A-918D have a second configuration, different from the first configuration.

In contrast to the embodiment described for FIGS. 14A-14D, if a swivel existed between the guide tube 914 and the arm 104 (e.g., the wrist attachment) with all four markers 918A-918D remaining attached rigidly to the guide tube 914 and this swivel was adjusted by the user, the robotic system 100, 300, 600 would not be able to automatically detect that the guide tube 914 orientation had changed. The robotic system 100, 300, 600 would track the positions of the marker array 908 and would calculate incorrect robot axis moves assuming the guide tube 914 was attached to the wrist (the robot arm 104) in the previous orientation. By keeping one or more markers 918A-918D (e.g., two markers 918C, 918D) rigidly on the tube 914 and one or more markers 918A-918D (e.g., two markers 918A, 918B) across the swivel, automatic detection of the new position becomes possible and correct robot moves are calculated based on the detection of a new tool or end-effector 112, 912 on the end of the robot arm 104.

One or more of the markers 918A-918D are configured to be moved, pivoted, swiveled, or the like according to any suitable means. For example, the markers 918A-918D may be moved by a hinge 920, such as a clamp, spring, lever, slide, toggle, or the like, or any other suitable mechanism for moving the markers 918A-918D individually or in combination, moving the arrays 908A, 908B individually or in combination, moving any portion of the end-effector 912 relative to another portion, or moving any portion of the tool 608 relative to another portion.

As shown in FIGS. 14A and 14B, the array 908 and guide tube 914 may become reconfigurable by simply loosening the clamp or hinge 920, moving part of the array 908A, 908B relative to the other part 908A, 908B, and retightening the hinge 920 such that the guide tube 914 is oriented in a different position. For example, two markers 918C, 918D may be rigidly interconnected with the tube 914 and two markers 918A, 918B may be rigidly interconnected across the hinge 920 to the base 906 of the end-effector 912 that attaches to the robot arm 104. The hinge 920 may be in the form of a clamp, such as a wing nut or the like, which can be loosened and retightened to allow the user to quickly switch between the first configuration (FIG. 14A) and the second configuration (FIG. 14B).

The cameras 200, 326 detect the markers 918A-918D, for example, in one of the templates identified in FIGS. 14C and 14D. If the array 908 is in the first configuration (FIG. 14A) and tracking cameras 200, 326 detect the markers 918A-918D, then the tracked markers match Array Template 1 as shown in FIG. 14C. If the array 908 is the second configuration (FIG. 14B) and tracking cameras 200, 326 detect the same markers 918A-918D, then the tracked markers match Array Template 2 as shown in FIG. 14D. Array Template 1 and Array Template 2 are recognized by the system 100, 300, 600 as two distinct tools, each with its own uniquely defined spatial relationship between guide tube 914, markers 918A-918D, and robot attachment. The user could therefore adjust the position of the end-effector 912 between the first and second configurations without notifying the system 100, 300, 600 of the change and the system 100, 300, 600 would appropriately adjust the movements of the robot 102 to stay on trajectory.

In this embodiment, there are two assembly positions in which the marker array matches unique templates that allow the system 100, 300, 600 to recognize the assembly as two different tools or two different end effectors. In any position of the swivel between or outside of these two positions (namely, Array Template 1 and Array Template 2 shown in FIGS. 14C and 14D, respectively), the markers 918A-918D would not match any template and the system 100, 300, 600 would not detect any array present despite individual markers 918A-918D being detected by cameras 200, 326, with the result being the same as if the markers 918A-918D were temporarily blocked from view of the cameras 200, 326. It will be appreciated that other array templates may exist for other configurations, for example, identifying different instruments 608 or other end-effectors 112, 912, etc.

In the embodiment described, two discrete assembly positions are shown in FIGS. 14A and 14B. It will be appreciated, however, that there could be multiple discrete positions on a swivel joint, linear joint, combination of swivel and linear joints, pegboard, or other assembly where unique marker templates may be created by adjusting the position of one or more markers 918A-918D of the array relative to the others, with each discrete position matching a particular template and defining a unique tool 608 or end-effector 112, 912 with different known attributes. In addition, although exemplified for end effector 912, it will be appreciated that moveable and fixed markers 918A-918D may be used with any suitable instrument 608 or other object to be tracked.

When using an external 3D tracking system 100, 300, 600 to track a full rigid body array of three or more markers attached to a robot's end effector 112 (for example, as depicted in FIGS. 13A and 13B), it is possible to directly track or to calculate the 3D position of every section of the robot 102 in the coordinate system of the cameras 200, 326. The geometric orientations of joints relative to the tracker are known by design, and the linear or angular positions of joints are known from encoders for each motor of the robot 102, fully defining the 3D positions of all of the moving parts from the end effector 112 to the base 116. Similarly, if a tracker were mounted on the base 106 of the robot 102 (not shown), it is likewise possible to track or calculate the 3D position of every section of the robot 102 from base 106 to end effector 112 based on known joint geometry and joint positions from each motor's encoder.

In some situations, it may be desirable to track the positions of all segments of the robot 102 from fewer than three markers 118 rigidly attached to the end effector 112. Specifically, if a tool 608 is introduced into the guide tube 114, it may be desirable to track full rigid body motion of the robot 902 with only one additional marker 118 being tracked.

Turning now to FIGS. 15A-15E, an alternative version of an end-effector 1012 having only a single tracking marker 1018 is shown. End-effector 1012 may be similar to the other end-effectors described herein, and may include a guide tube 1014 extending along a longitudinal axis 1016. A single tracking marker 1018, similar to the other tracking markers described herein, may be rigidly affixed to the guide tube 1014. This single marker 1018 can serve the purpose of adding missing degrees of freedom to allow full rigid body tracking and/or can serve the purpose of acting as a surveillance marker to ensure that assumptions about robot and camera positioning are valid.

The single tracking marker 1018 may be attached to the robotic end effector 1012 as a rigid extension to the end effector 1012 that protrudes in any convenient direction and does not obstruct the surgeon's view. The tracking marker 1018 may be affixed to the guide tube 1014 or any other suitable location of on the end-effector 1012. When affixed to the guide tube 1014, the tracking marker 1018 may be positioned at a location between first and second ends of the guide tube 1014. For example, in FIG. 15A, the single tracking marker 1018 is shown as a reflective sphere mounted on the end of a narrow shaft 1017 that extends forward from the guide tube 1014 and is positioned longitudinally above a mid-point of the guide tube 1014 and below the entry of the guide tube 1014. This position allows the marker 1018 to be generally visible by cameras 200, 326 but also would not obstruct vision of the surgeon 120 or collide with other tools or objects in the vicinity of surgery. In addition, the guide tube 1014 with the marker 1018 in this position is designed for the marker array on any tool 608 introduced into the guide tube 1014 to be visible at the same time as the single marker 1018 on the guide tube 1014 is visible.

Figure 15A:
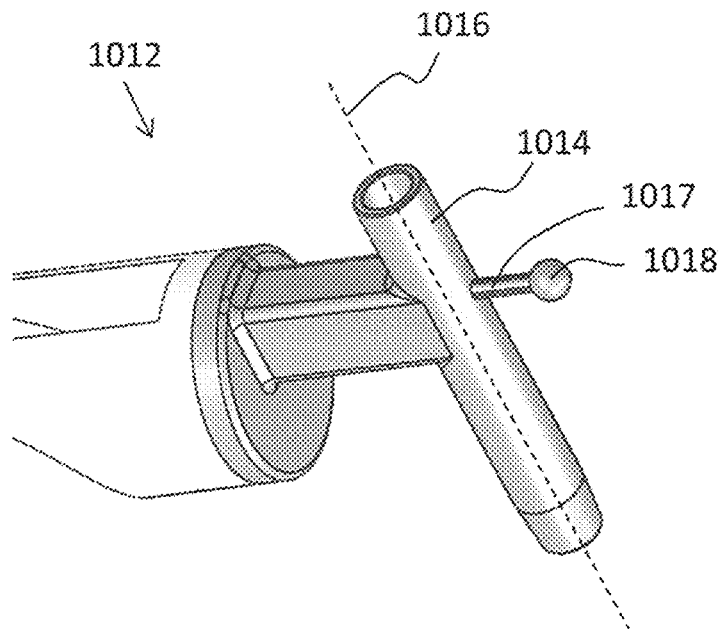
FIG. 15A shows an alternative version of the end-effector having only a single tracking marker affixed thereto.
Figure 15B:
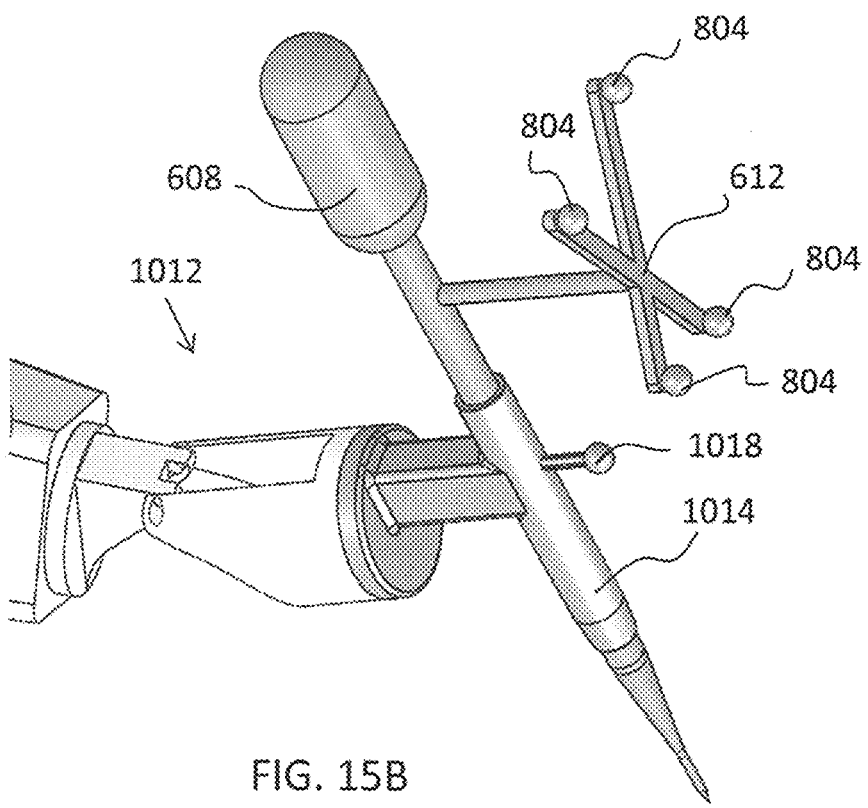
FIG. 15B shows the end-effector of FIG. 15A with an instrument disposed through the guide tube.

As shown in FIG. 15B, when a snugly fitting tool or instrument 608 is placed within the guide tube 1014, the instrument 608 becomes mechanically constrained in 4 of 6 degrees of freedom. That is, the instrument 608 cannot be rotated in any direction except about the longitudinal axis 1016 of the guide tube 1014 and the instrument 608 cannot be translated in any direction except along the longitudinal axis 1016 of the guide tube 1014. In other words, the instrument 608 can only be translated along and rotated about the centerline of the guide tube 1014. If two more parameters are known, such as (1) an angle of rotation about the longitudinal axis 1016 of the guide tube 1014; and (2) a position along the guide tube 1014, then the position of the end effector 1012 in the camera coordinate system becomes fully defined.

Figure 15C:
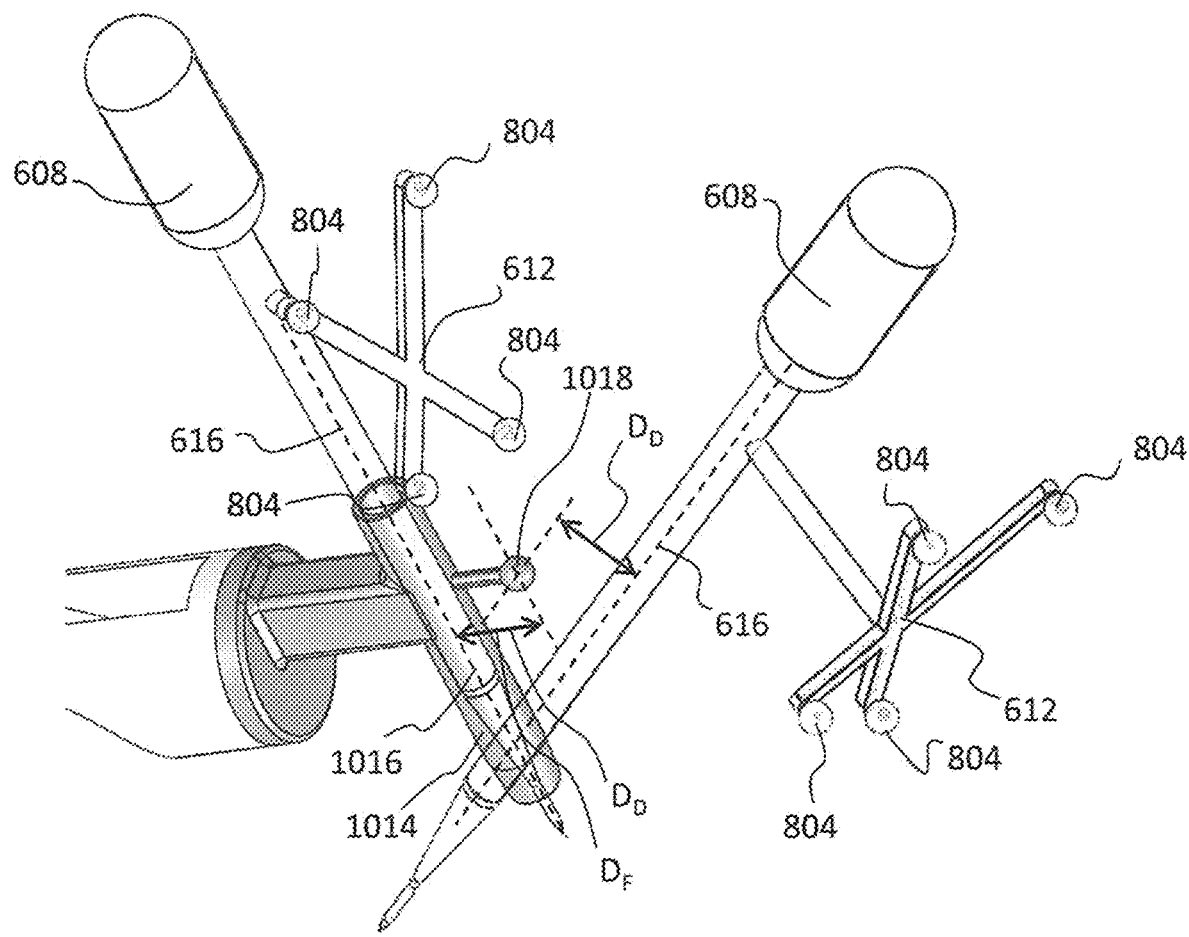
FIG. 15C shows the end-effector of FIG. 15A with the instrument in two different positions, and the resulting logic to determine if the instrument is positioned within the guide tube or outside of the guide tube.

Referring now to FIG. 15C, the system 100, 300, 600 should be able to know when a tool 608 is actually positioned inside of the guide tube 1014 and is not instead outside of the guide tube 1014 and just somewhere in view of the cameras 200, 326. The tool 608 has a longitudinal axis or centerline 616 and an array 612 with a plurality of tracked markers 804. The rigid body calculations may be used to determine where the centerline 616 of the tool 608 is located in the camera coordinate system based on the tracked position of the array 612 on the tool 608.

The fixed normal (perpendicular) distance DF from the single marker 1018 to the centerline or longitudinal axis 1016 of the guide tube 1014 is fixed and is known geometrically, and the position of the single marker 1018 can be tracked. Therefore, when a detected distance DD from tool centerline 616 to single marker 1018 matches the known fixed distance DF from the guide tube centerline 1016 to the single marker 1018, it can be determined that the tool 608 is either within the guide tube 1014 (centerlines 616, 1016 of tool 608 and guide tube 1014 coincident) or happens to be at some point in the locus of possible positions where this distance DD matches the fixed distance DF. For example, in FIG. 15C, the normal detected distance DD from tool centerline 616 to the single marker 1018 matches the fixed distance DF from guide tube centerline 1016 to the single marker 1018 in both frames of data (tracked marker coordinates) represented by the transparent tool 608 in two positions, and thus, additional considerations may be needed to determine when the tool 608 is located in the guide tube 1014.

Figure 15D:
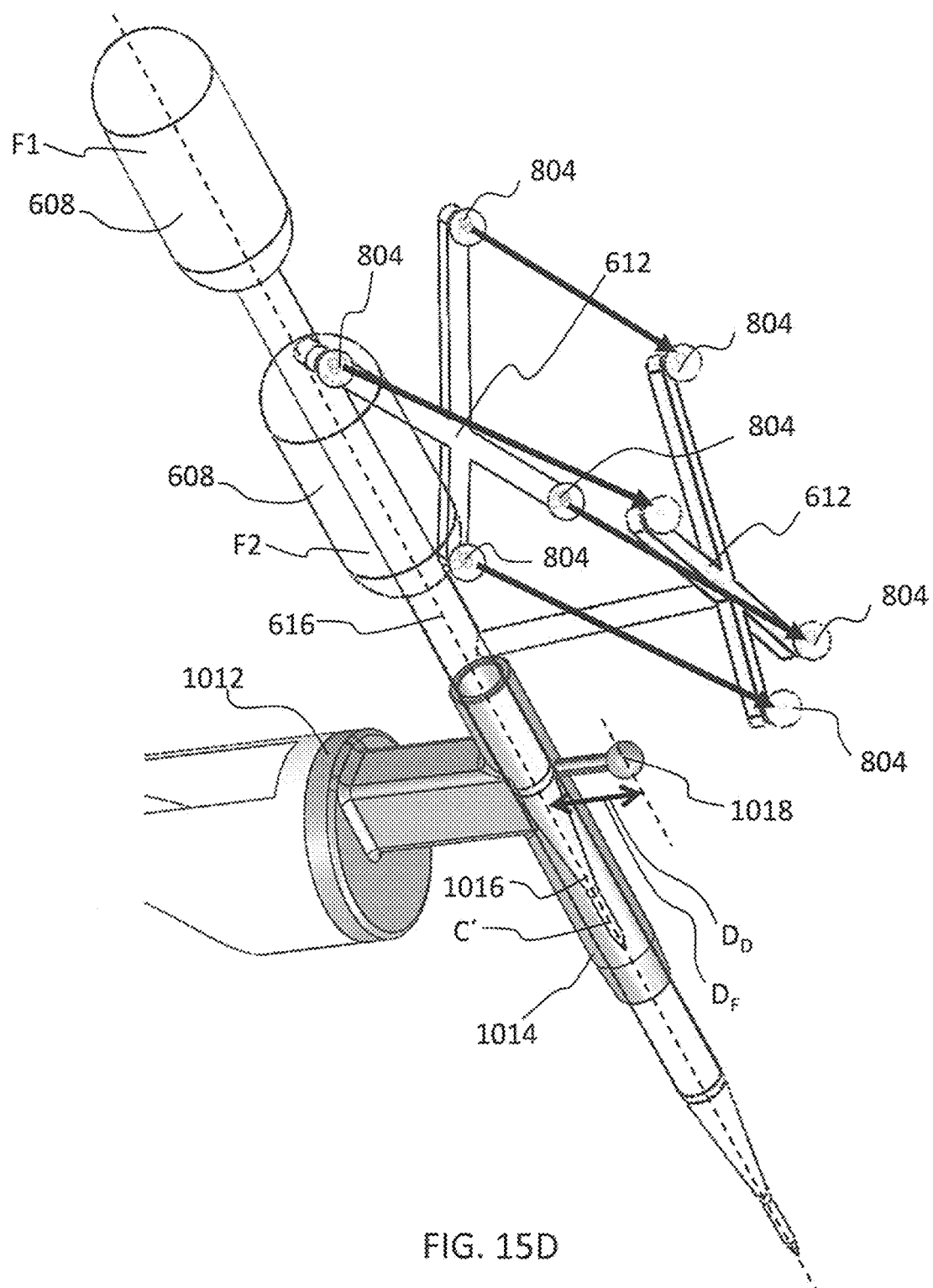
FIG. 15D shows the end-effector of FIG. 15A with the instrument in the guide tube at two different frames and its relative distance to the single tracking marker on the guide tube.

Turning now to FIG. 15D, programmed logic can be used to look for frames of tracking data in which the detected distance DD from tool centerline 616 to single marker 1018 remains fixed at the correct length despite the tool 608 moving in space by more than some minimum distance relative to the single sphere 1018 to satisfy the condition that the tool 608 is moving within the guide tube 1014. For example, a first frame F1 may be detected with the tool 608 in a first position and a second frame F2 may be detected with the tool 608 in a second position (namely, moved linearly with respect to the first position). The markers 804 on the tool array 612 may move by more than a given amount (e.g., more than 5 mm total) from the first frame F1 to the second frame F2. Even with this movement, the detected distance DD from the tool centerline vector C' to the single marker 1018 is substantially identical in both the first frame F1 and the second frame F2.

Logistically, the surgeon 120 or user could place the tool 608 within the guide tube 1014 and slightly rotate it or slide it down into the guide tube 1014 and the system 100, 300, 600 would be able to detect that the tool 608 is within the guide tube 1014 from tracking of the five markers (four markers 804 on tool 608 plus single marker 1018 on guide tube 1014). Knowing that the tool 608 is within the guide tube 1014, all 6 degrees of freedom may be calculated that define the position and orientation of the robotic end effector 1012 in space. Without the single marker 1018, even if it is known with certainty that the tool 608 is within the guide tube 1014, it is unknown where the guide tube 1014 is located along the tool's centerline vector C' and how the guide tube 1014 is rotated relative to the centerline vector C'.

Figure 15E:
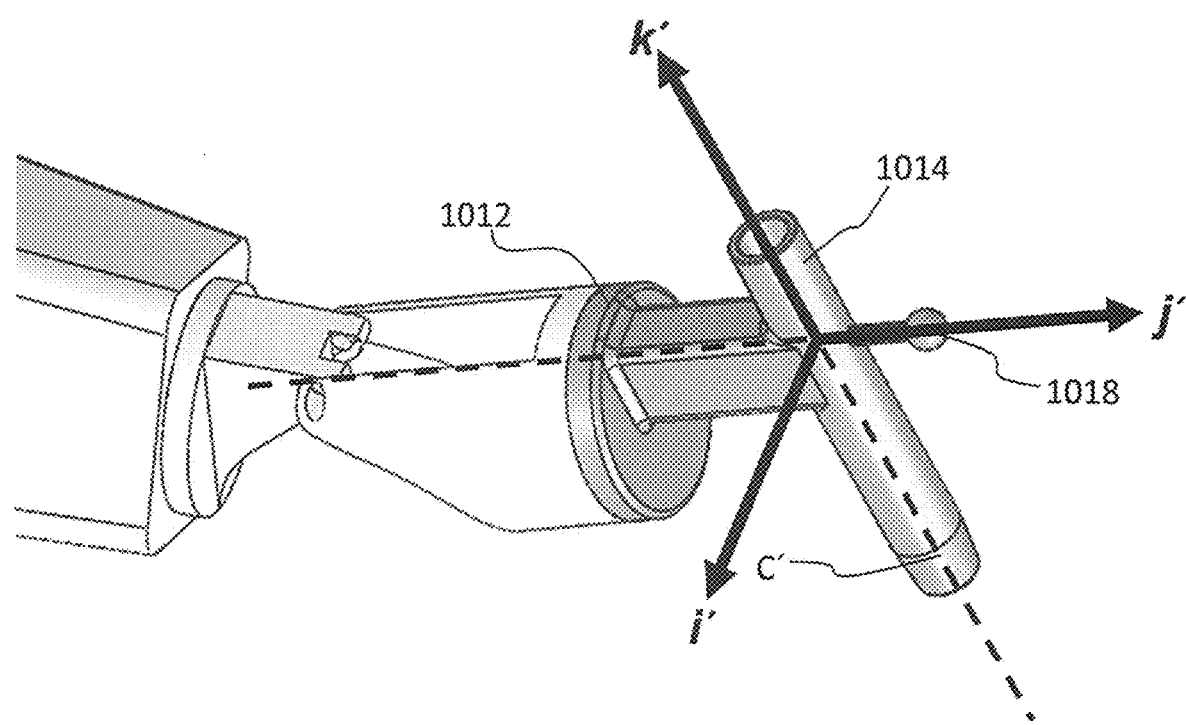
FIG. 15E shows the end-effector of FIG. 15A relative to a coordinate system.

With emphasis on FIG. 15E, the presence of the single marker 1018 being tracked as well as the four markers 804 on the tool 608, it is possible to construct the centerline vector C' of the guide tube 1014 and tool 608 and the normal vector through the single marker 1018 and through the centerline vector C'. This normal vector has an orientation that is in a known orientation relative to the forearm of the robot distal to the wrist (in this example, oriented parallel to that segment) and intersects the centerline vector C' at a specific fixed position. For convenience, three mutually orthogonal vectors k', j', i' can be constructed, as shown in FIG. 15E, defining rigid body position and orientation of the guide tube 1014. One of the three mutually orthogonal vectors k' is constructed from the centerline vector C', the second vector j' is constructed from the normal vector through the single marker 1018, and the third vector i' is the vector cross product of the first and second vectors k', j'. The robot's joint positions relative to these vectors k', j', I' are known and fixed when all joints are at zero, and therefore rigid body calculations can be used to determine the location of any section of the robot relative to these vectors k', j', i' when the robot is at a home position. During robot movement, if the positions of the tool markers 804 (while the tool 608 is in the guide tube 1014) and the position of the single marker 1018 are detected from the tracking system, and angles/linear positions of each joint are known from encoders, then position and orientation of any section of the robot can be determined.

In some embodiments, it may be useful to fix the orientation of the tool 608 relative to the guide tube 1014. For example, the end effector guide tube 1014 may be oriented in a particular position about its axis 1016 to allow machining or implant positioning. Although the orientation of anything attached to the tool 608 inserted into the guide tube 1014 is known from the tracked markers 804 on the tool 608, the rotational orientation of the guide tube 1014 itself in the camera coordinate system is unknown without the additional tracking marker 1018 (or multiple tracking markers in other embodiments) on the guide tube 1014. This marker 1018 provides essentially a "clock position" from $-180°$ to $+180°$ based on the orientation of the marker 1018 relative to the centerline vector C'. Thus, the single marker 1018 can provide additional degrees of freedom to allow full rigid body tracking and/or can act as a surveillance marker to ensure that assumptions about the robot and camera positioning are valid.

Figure 16:
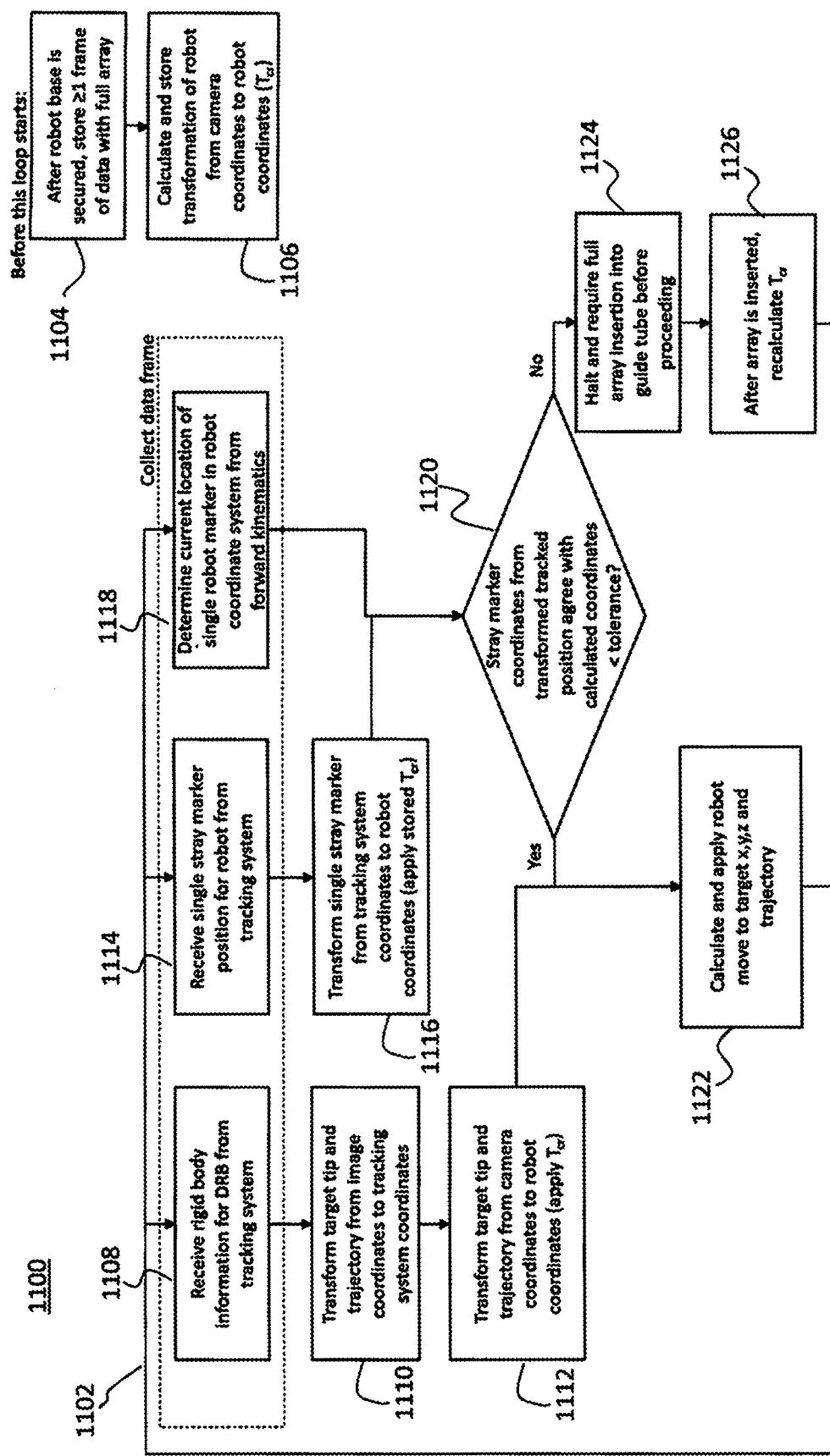
FIG. 16 is a block diagram of a method for navigating and moving the end-effector of the robot to a desired target trajectory.

FIG. 16 is a block diagram of a method 1100 for navigating and moving the end-effector 1012 (or any other end-effector described herein) of the robot 102 to a desired target trajectory. Another use of the single marker 1018 on the robotic end effector 1012 or guide tube 1014 is as part of the method 1100 enabling the automated safe movement of the robot 102 without a full tracking array attached to the robot 102. This method 1100 functions when the tracking cameras 200, 326 do not move relative to the robot 102 (i.e., they are in a fixed position), the tracking system's coordinate system and robot's coordinate system are co-registered, and the robot 102 is calibrated such that the position and orientation of the guide tube 1014 can be accurately determined in the robot's Cartesian coordinate system based only on the encoded positions of each robotic axis.

For this method 1100, the coordinate systems of the tracker and the robot must be co-registered, meaning that the coordinate transformation from the tracking system's Cartesian coordinate system to the robot's Cartesian coordinate system is needed. For convenience, this coordinate transformation can be a 4×4 matrix of translations and rotations that is well known in the field of robotics. This transformation will be termed Tcr to refer to "transformation—camera to robot". Once this transformation is known, any new frame of tracking data, which is received as x,y,z coordinates in vector form for each tracked marker, can be multiplied by the 4×4 matrix and the resulting x,y,z coordinates will be in the robot's coordinate system. To obtain Tcr, a full tracking array on the robot is tracked while it is rigidly attached to the robot at a location that is known in the robot's coordinate system, then known rigid body methods are used to calculate the transformation of coordinates. It should be evident that any tool 608 inserted into the guide tube 1014 of the robot 102 can provide the same rigid body information as a rigidly attached array when the additional marker 1018 is also read. That is, the tool 608 need only be inserted to any position within the guide tube 1014 and at any rotation within the guide tube 1014, not to a fixed position and orientation. Thus, it is possible to determine Tcr by inserting any tool 608 with a tracking array 612 into the guide tube 1014 and reading the tool's array 612 plus the single marker 1018 of the guide tube 1014 while at the same time determining from the encoders on each axis the current location of the guide tube 1014 in the robot's coordinate system.

Logic for navigating and moving the robot 102 to a target trajectory is provided in the method 1100 of FIG. 16. Before entering the loop 1102, it is assumed that the transformation Tcr was previously stored. Thus, before entering loop 1102, in step 1104, after the robot base 106 is secured, greater than or equal to one frame of tracking data of a tool inserted in the guide tube while the robot is static is stored; and in step 1106, the transformation of robot guide tube position from camera coordinates to robot coordinates Tcr is calculated from this static data and previous calibration data. Tcr should remain valid as long as the cameras 200, 326 do not move relative to the robot 102. If the cameras 200, 326 move relative to the robot 102, and Tcr needs to be re-obtained, the system 100, 300, 600 can be made to prompt the user to insert a tool 608 into the guide tube 1014 and then automatically perform the necessary calculations.

In the flowchart of method 1100, each frame of data collected consists of the tracked position of the DRB 1404 on the patient 210, the tracked position of the single marker 1018 on the end effector 1014, and a snapshot of the positions of each robotic axis. From the positions of the robot's axes, the location of the single marker 1018 on the end effector 1012 is calculated. This calculated position is compared to the actual position of the marker 1018 as recorded from the tracking system. If the values agree, it can be assured that the robot 102 is in a known location. The transformation Tcr is applied to the tracked position of the DRB 1404 so that the target for the robot 102 can be provided in terms of the robot's coordinate system. The robot 102 can then be commanded to move to reach the target.

After steps 1104, 1106, loop 1102 includes step 1108 receiving rigid body information for DRB 1404 from the tracking system; step 1110 transforming target tip and trajectory from image coordinates to tracking system coordinates; and step 1112 transforming target tip and trajectory from camera coordinates to robot coordinates (apply Tcr). Loop 1102 further includes step 1114 receiving a single stray marker position for robot from tracking system; and step 1116 transforming the single stray marker from tracking system coordinates to robot coordinates (apply stored Tcr). Loop 1102 also includes step 1118 determining current location of the single robot marker 1018 in the robot coordinate system from forward kinematics. The information from steps 1116 and 1118 is used to determine step 1120 whether the stray marker coordinates from transformed tracked position agree with the calculated coordinates being less than a given tolerance. If yes, proceed to step 1122, calculate and apply robot move to target x, y, z and trajectory. If no, proceed to step 1124, halt and require full array insertion into guide tube 1014 before proceeding; step 1126 after array is inserted, recalculate Tcr; and then proceed to repeat steps 1108, 1114, and 1118.

This method 1100 has advantages over a method in which the continuous monitoring of the single marker 1018 to verify the location is omitted. Without the single marker 1018, it would still be possible to determine the position of the end effector 1012 using Tcr and to send the end-effector 1012 to a target location but it would not be possible to verify that the robot 102 was actually in the expected location. For example, if the cameras 200, 326 had been bumped and Tcr was no longer valid, the robot 102 would move to an erroneous location. For this reason, the single marker 1018 provides value with regard to safety.

For a given fixed position of the robot 102, it is theoretically possible to move the tracking cameras 200, 326 to a new location in which the single tracked marker 1018 remains unmoved since it is a single point, not an array. In such a case, the system 100, 300, 600 would not detect any error since there would be agreement in the calculated and tracked locations of the single marker 1018. However, once the robot's axes caused the guide tube 1012 to move to a new location, the calculated and tracked positions would disagree and the safety check would be effective.

The term "surveillance marker" may be used, for example, in reference to a single marker that is in a fixed location relative to the DRB 1404. In this instance, if the DRB 1404 is bumped or otherwise dislodged, the relative location of the surveillance marker changes and the surgeon 120 can be alerted that there may be a problem with navigation. Similarly, in the embodiments described herein, with a single marker 1018 on the robot's guide tube 1014, the system 100, 300, 600 can continuously check whether the cameras 200, 326 have moved relative to the robot 102. If registration of the tracking system's coordinate system to the robot's coordinate system is lost, such as by cameras 200, 326 being bumped or malfunctioning or by the robot malfunctioning, the system 100, 300, 600 can alert the user and corrections can be made. Thus, this single marker 1018 can also be thought of as a surveillance marker for the robot 102.

It should be clear that with a full array permanently mounted on the robot 102 (e.g., the plurality of tracking markers 702 on end-effector 602 shown in FIGS. 7A-7C) such functionality of a single marker 1018 as a robot surveillance marker is not needed because it is not required that the cameras 200, 326 be in a fixed position relative to the robot 102, and Tcr is updated at each frame based on the tracked position of the robot 102. Reasons to use a single marker 1018 instead of a full array are that the full array is more bulky and obtrusive, thereby blocking the surgeon's view and access to the surgical field 208 more than a single marker 1018, and line of sight to a full array is more easily blocked than line of sight to a single marker 1018.

Turning now to FIGS. 17A-17B and 18A-18B, instruments 608, such as implant holders 608B, 608C, are depicted which include both fixed and moveable tracking markers 804, 806. The implant holders 608B, 608C may have a handle 620 and an outer shaft 622 extending from the handle 620. The shaft 622 may be positioned substantially perpendicular to the handle 620, as shown, or in any other suitable orientation. An inner shaft 626 may extend through the outer shaft 622 with a knob 628 at one end. Implant 10, 12 connects to the shaft 622, at the other end, at tip 624 of the implant holder 608B, 608C using typical connection mechanisms known to those of skill in the art. The knob 628 may be rotated, for example, to expand or articulate the implant 10, 12. U.S. Pat. Nos. 8,709,086 and 8,491,659, the disclosures of which are incorporated by reference herein, describe expandable fusion devices and methods of installation.

When tracking the tool 608, such as implant holder 608B, 608C, the tracking array 612 may contain a combination of fixed markers 804 and one or more moveable markers 806 which make up the array 612 or is otherwise attached to the implant holder 608B, 608C. The navigation array 612 may include at least one or more (e.g., at least two) fixed position markers 804, which are positioned with a known location relative to the implant holder instrument 608B, 608C. These fixed markers 804 would not be able to move in any orientation relative to the instrument geometry and would be useful in defining where the instrument 608 is in space. In addition, at least one marker 806 is present which can be attached to the array 612 or the instrument itself which is capable of moving within a pre-determined boundary (e.g., sliding, rotating, etc.) relative to the fixed markers 804. The system 100, 300, 600 (e.g., the software) correlates the position of the moveable marker 806 to a particular position, orientation, or other attribute of the implant 10 (such as height of an expandable interbody spacer shown in FIGS. 17A-17B or angle of an articulating interbody spacer shown in FIGS. 18A-18B). Thus, the system and/or the user can determine the height or angle of the implant 10, 12 based on the location of the moveable marker 806.

Figure 17A:
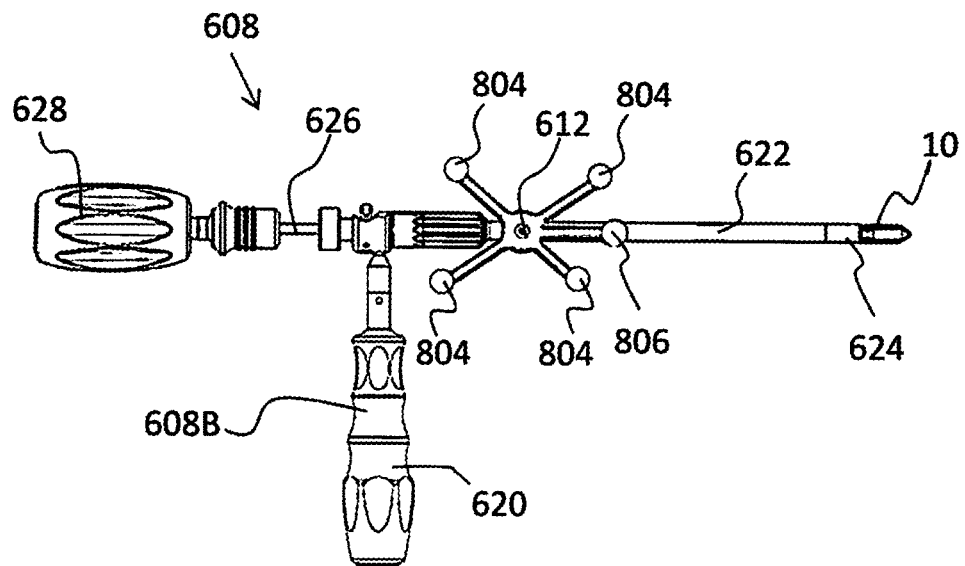
FIGS. 17A-17B depict an instrument for inserting an expandable implant having fixed and moveable tracking markers in contracted and expanded positions, respectively.
Figure 17B:
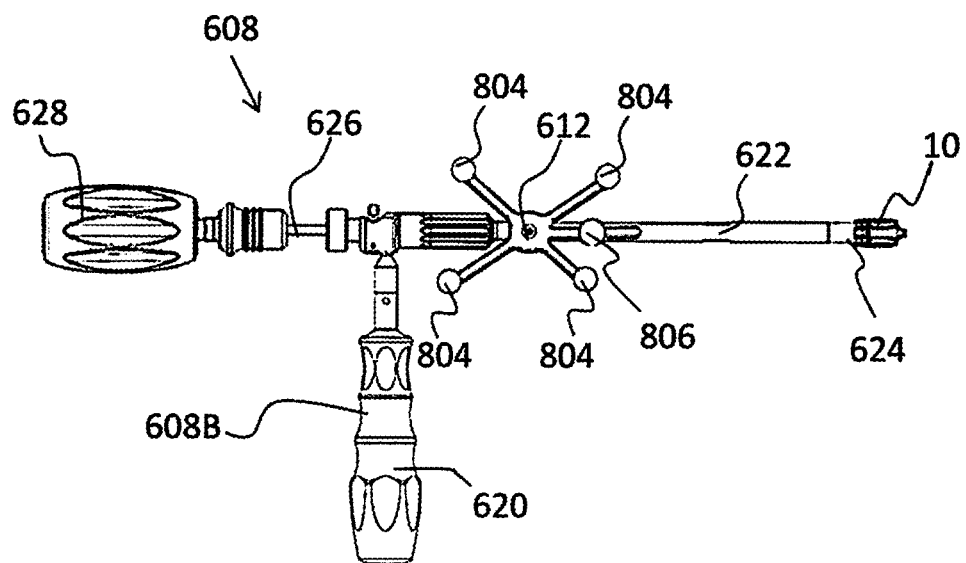

In the embodiment shown in FIGS. 17A-17B, four fixed markers 804 are used to define the implant holder 608B and a fifth moveable marker 806 is able to slide within a pre-determined path to provide feedback on the implant height (e.g., a contracted position or an expanded position). FIG. 17A shows the expandable spacer 10 at its initial height, and FIG. 17B shows the spacer 10 in the expanded state with the moveable marker 806 translated to a different position. In this case, the moveable marker 806 moves closer to the fixed markers 804 when the implant 10 is expanded, although it is contemplated that this movement may be reversed or otherwise different. The amount of linear translation of the marker 806 would correspond to the height of the implant 10. Although only two positions are shown, it would be possible to have this as a continuous function whereby any given expansion height could be correlated to a specific position of the moveable marker 806.

Figure 18A:
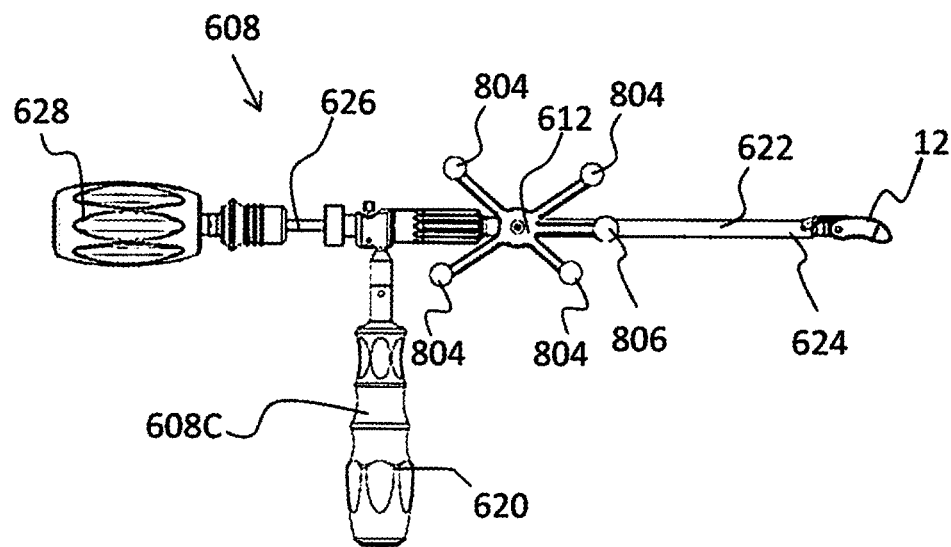
FIGS. 18A-18B depict an instrument for inserting an articulating implant having fixed and moveable tracking markers in insertion and angled positions, respectively.
Figure 18B:
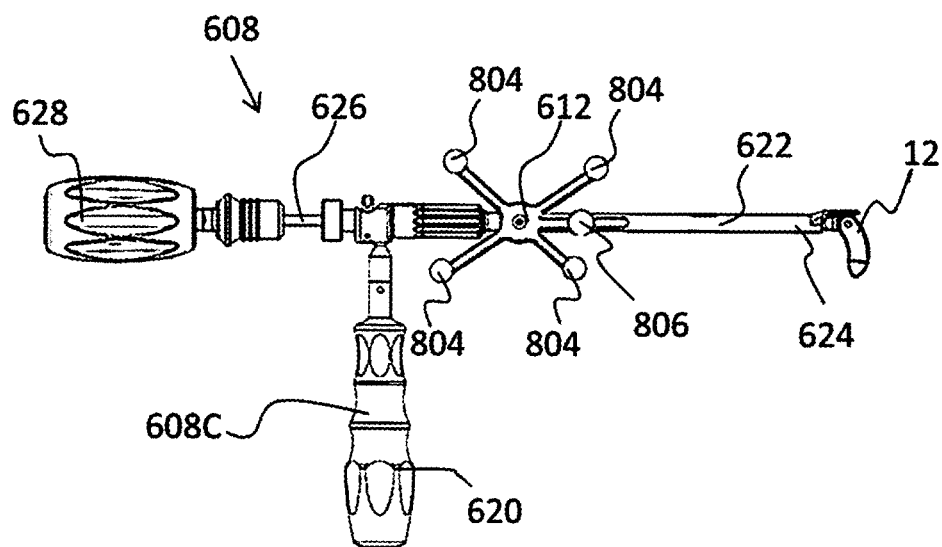

Turning now to FIGS. 18A-18B, four fixed markers 804 are used to define the implant holder 608C and a fifth, moveable marker 806 is configured to slide within a pre-determined path to provide feedback on the implant articulation angle. FIG. 18A shows the articulating spacer 12 at its initial linear state, and FIG. 18B shows the spacer 12 in an articulated state at some offset angle with the moveable marker 806 translated to a different position. The amount of linear translation of the marker 806 would correspond to the articulation angle of the implant 12. Although only two positions are shown, it would be possible to have this as a continuous function whereby any given articulation angle could be correlated to a specific position of the moveable marker 806.

In these embodiments, the moveable marker 806 slides continuously to provide feedback about an attribute of the implant 10, 12 based on position. It is also contemplated that there may be discreet positions that the moveable marker 806 must be in which would also be able to provide further information about an implant attribute. In this case, each discreet configuration of all markers 804, 806 correlates to a specific geometry of the implant holder 608B, 608C and the implant 10, 12 in a specific orientation or at a specific height. In addition, any motion of the moveable marker 806 could be used for other variable attributes of any other type of navigated implant.

Although depicted and described with respect to linear movement of the moveable marker 806, the moveable marker 806 should not be limited to just sliding as there may be applications where rotation of the marker 806 or other movements could be useful to provide information about the implant 10, 12. Any relative change in position between the set of fixed markers 804 and the moveable marker 806 could be relevant information for the implant 10, 12 or other device. In addition, although expandable and articulating implants 10, 12 are exemplified, the instrument 608 could work with other medical devices and materials, such as spacers, cages, plates, fasteners, nails, screws, rods, pins, wire structures, sutures, anchor clips, staples, stents, bone grafts, biologics, cements, or the like.

Figure 19A:
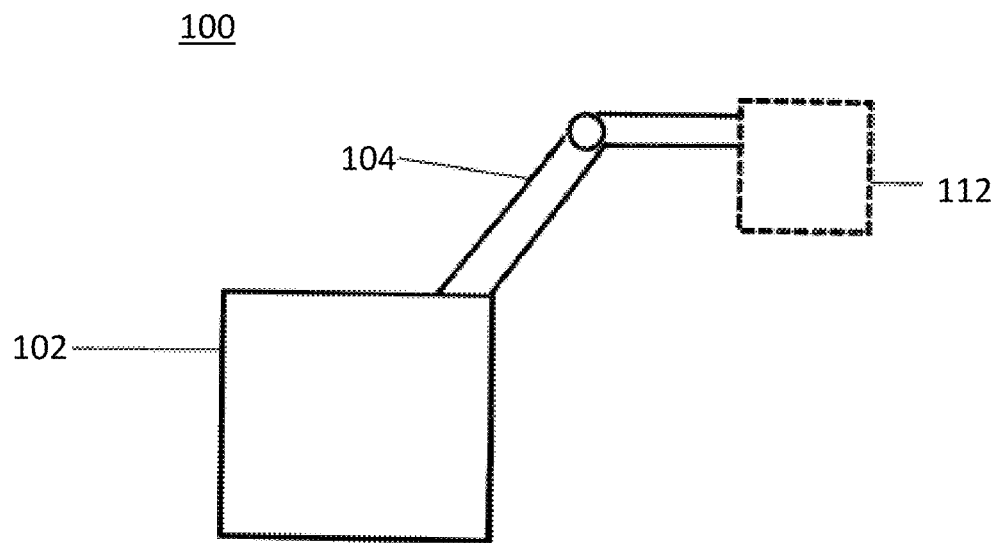
FIG. 19A depicts an embodiment of a robot with interchangeable or alternative end-effectors.

Turning now to FIG. 19A, it is envisioned that the robot end-effector 112 is interchangeable with other types of end-effectors 112. Moreover, it is contemplated that each end-effector 112 may be able to perform one or more functions based on a desired surgical procedure. For example, the end-effector 112 having a guide tube 114 may be used for guiding an instrument 608 as described herein. In addition, end-effector 112 may be replaced with a different or alternative end-effector 112 that controls a surgical device, instrument, or implant, for example.

The alternative end-effector 112 may include one or more devices or instruments coupled to and controllable by the robot. By way of non-limiting example, the end-effector 112, as depicted in FIG. 19A, may comprise a retractor (for example, one or more retractors disclosed in U.S. Pat. Nos. 8,992,425 and 8,968,363) or one or more mechanisms for inserting or installing surgical devices such as expandable intervertebral fusion devices (such as expandable implants exemplified in U.S. Pat. Nos. 8,845,734; 9,510,954; and 9,456,903), stand-alone intervertebral fusion devices (such as implants exemplified in U.S. Pat. Nos. 9,364,343 and 9,480,579), expandable corpectomy devices (such as corpectomy implants exemplified in U.S. Pat. Nos. 9,393,128 and 9,173,747), articulating spacers (such as implants exemplified in U.S. Pat. No. 9,259,327), facet prostheses (such as devices exemplified in U.S. Pat. No. 9,539,031), laminoplasty devices (such as devices exemplified in U.S. Pat. No. 9,486,253), spinous process spacers (such as implants exemplified in U.S. Pat. No. 9,592,082), inflatables, fasteners including polyaxial screws, uniplanar screws, pedicle screws, posted screws, and the like, bone fixation plates, rod constructs and revision devices (such as devices exemplified in U.S. Pat. No. 8,882,803), artificial and natural discs, motion preserving devices and implants, spinal cord stimulators (such as devices exemplified in U.S. Pat. No. 9,440,076), and other surgical devices. The end-effector 112 may include one or instruments directly or indirectly coupled to the robot for providing bone cement, bone grafts, living cells, pharmaceuticals, or other deliverable to a surgical target. The end-effector 112 may also include one or more instruments designed for performing a discectomy, kyphoplasty, vertebrostenting, dilation, or other surgical procedure.

The end-effector itself and/or the implant, device, or instrument may include one or more markers 118 such that the location and position of the markers 118 may be identified in three-dimensions. It is contemplated that the markers 118 may include active or passive markers 118, as described herein, that may be directly or indirectly visible to the cameras 200. Thus, one or more markers 118 located on an implant 10, for example, may provide for tracking of the implant 10 before, during, and after implantation.

Figure 19B:
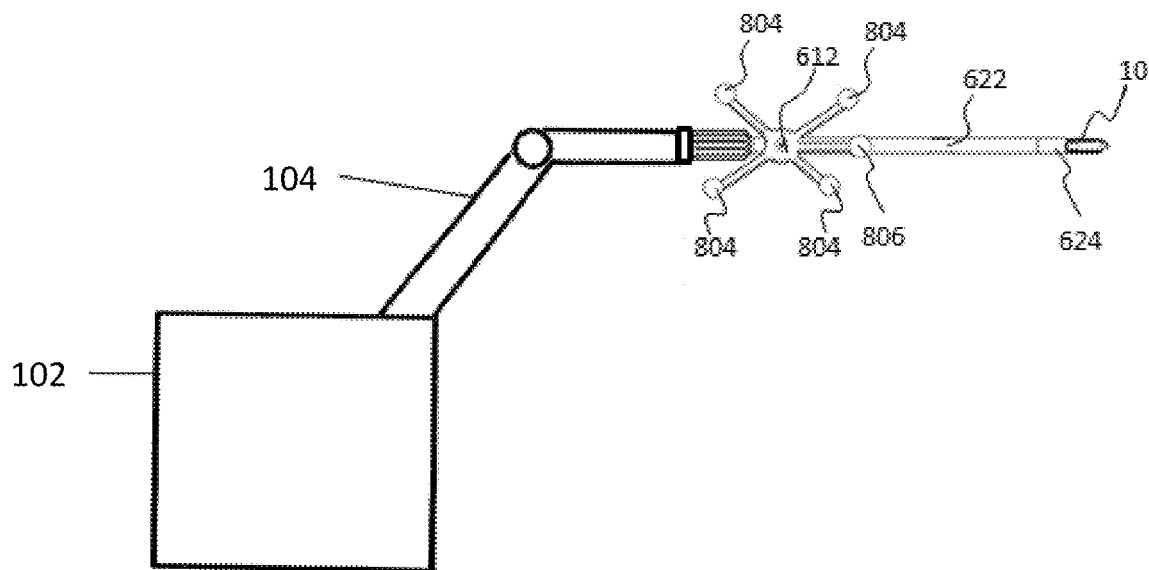
FIG. 19B depicts an embodiment of a robot with an instrument style end-effector coupled thereto.

As shown in FIG. 19B, the end-effector 112 may include an instrument 608 or portion thereof that is coupled to the robot arm 104 (for example, the instrument 608 may be coupled to the robot arm 104 by the coupling mechanism shown in FIGS. 9A-9C) and is controllable by the robot system 100. Thus, in the embodiment shown in FIG. 19B, the robot system 100 is able to insert implant 10 into a patient and expand or contract the expandable implant 10. Accordingly, the robot system 100 may be configured to assist a surgeon or to operate partially or completely independently thereof. Thus, it is envisioned that the robot system 100 may be capable of controlling each alternative end-effector 112 for its specified function or surgical procedure. Although the robot and associated systems described above are generally described with reference to spine applications, it is also contemplated that the robot system is configured for use in other surgical applications, including but not limited to, surgeries in trauma or other orthopedic applications (such as the placement of intramedullary nails, plates, and the like), cranial, neuro, cardiothoracic, vascular, colorectal, oncological, dental, and other surgical operations and procedures. According to some embodiments discussed below, robot systems may be used for brain surgery applications.

Current 2-BB-plane methods to register fluoroscopic x-ray images (also referred to as fluoroscopic images, fluoro images, fluoroscopic shots, fluoro shots, fluoroscopic x-ray shots, etc.) to optical tracking cameras when using fluoro-only or pre-op computerized tomography (CT) scan workflows in surgical navigation may have shortcomings as discussed below.

1) It may be difficult to automatically and/or accurately locate shadows of metal BBs of a fluoroscopic fixture in the presence of other shadows on fluoroscopic x-ray images.
2) The presence of multiple BBs or other radio-opaque fiducials on fluoroscopic x-ray images may cause undesirable clutter on the images.
3) The height of the outer BB plane may make it difficult to get the fluoroscopic x-ray detector close enough to the patient, causing fluoroscopic x-ray images to be too magnified (e.g., with a field of view that is too narrow).
4) Because the registration algorithm may require several BBs to be accurately found on the fluoroscopic x-ray images, it may not be possible to collimate the images to the desired extent.

According to some embodiments of inventive concepts, some or all of the above issues may be addressed.

Surgical navigation often uses/requires the registration of a pair of fluoroscopic x-ray images to an optical tracking system used to provide robotic control/navigation and/or surgical planning. For example, the current ExcelsiusGPS application allows planning of screw placements, positioning of the robot, and/or navigation of tools based on two registered fluoroscopic x-ray image shots alone (fluoro workflow). The current ExcelsiusGPS application also allows co-registration of a pair of registered fluoroscopic x-ray image shots to a prior CT scan (pre-operative CT workflow). In both workflows, accurate registration of the pair of fluoro images to the optical tracking cameras may be necessary.

Figure 22:
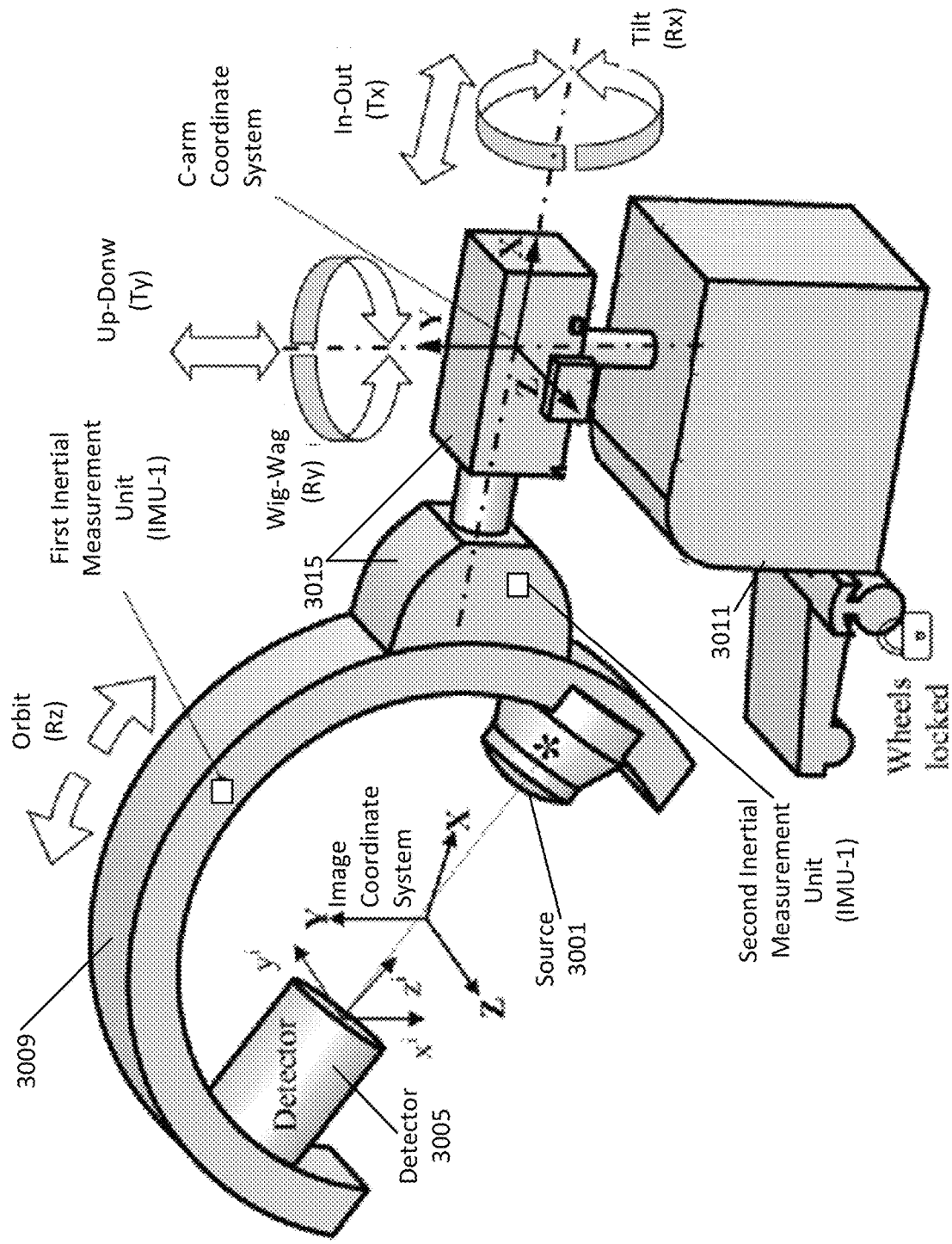
FIG. 22 is a diagram illustrating a configuration of a fluoroscopic x-ray imaging system according to some embodiments of inventive concepts.

A C-arm fluoroscopic x-ray imaging system (also referred to as a fluoroscopy unit/system or fluoroscopic unit/system) is illustrated in FIG. 22. As shown, an x-ray source 3001 (also referred to as a source, an emitter, an x-ray emitter, etc.) and an x-ray detector 3005 (also referred to as a detector, collector, or image intensifier) are mounted on a C-arm 3009. The C-arm 3009 may be mounted to a base 3011 of the system via a positioning mechanism 3015 that is configured to provide in-out Tx and up-down Ty translational movement and to provide tilt Rx, wig-wag Ry, and orbit Rz rotational movement of the C-arm 3009 relative to the base 3011. By positioning the source 3001 and detector 3005 on opposite sides of the patient (e.g., a patient lying on an operating table), x-ray radiation can be transmitted by source 3001 through the patient to detector 3005, and the detected radiation from detector 3005 can be processed to generate a fluoroscopic x-ray image of the patient's anatomy (also referred to as a fluoro shot), and the C-arm 3009 can be rotated about tilt Rx, wig-wag Ry, and/or orbit Rz so that multiple images of the same anatomy/tissue may be generated from different angles of tilt Rx, wig-wag Ry, and/or orbit Rz. A 3-D reference tracking volume may be determined using two images taken from different angles of tilt Rx, wig-wag Ry, and/or orbit Rz, and this 3-D reference tracking volume may be used to predict how objects in the path of x-rays would appear on the images, and vice versa. That is, by tracking the positions of the collector and emitter when x-ray shots are taken and detecting shadows of reference fiducials in these x-ray shots, there is a closed-form mathematical solution that allows the position of any new object appearing in the 3-D reference volume (defined in camera coordinates) to be mapped to the 2-D shots, and the position of any object simultaneously appearing in both of the 2-D shots to be mapped to the 3-D reference space of the cameras.

In the fluoro workflow, the registration of the tracked reference space to the x-ray images is all that is used or needed to allow planning and navigation, where screws or other surgical implants are planned on the 2-D shots and tool and robot positions can be driven or observed where they appear on the 2-D shot. It is often useful to register the 3-D reference space described above to the 3-D image volume of a CT scan, cone-beam CT volume, or MM volume. Once reference space and image volume are registered, planning and navigation of surgical implants can be performed relative to the image volume in 3-D. Some embodiments disclosed herein, relate to registration of a tracked 3-D reference space to the 2-D fluoro shots.

Figure 20:
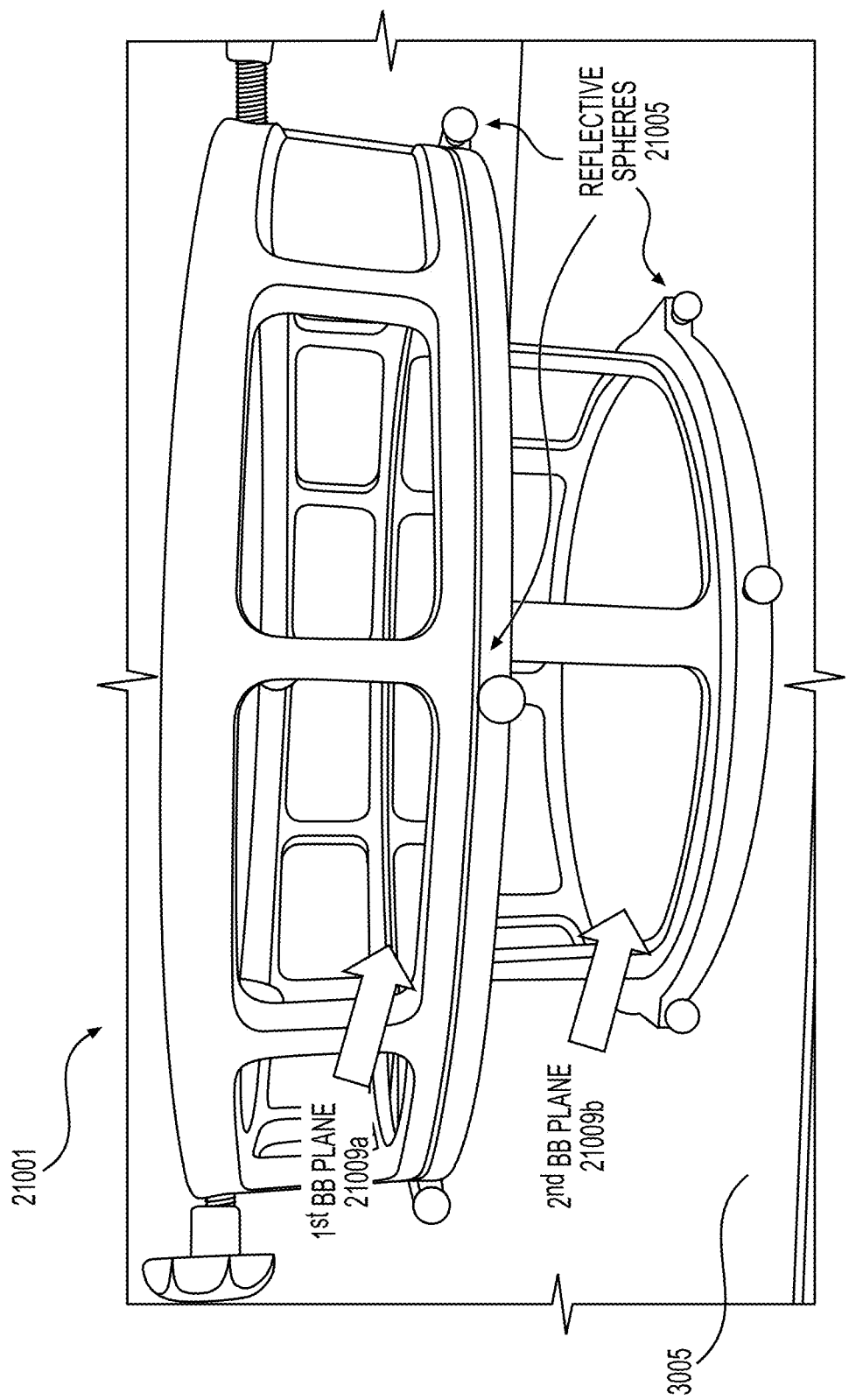
FIG. 20 is a photograph illustrating a fixture including multiple BB/fiducial planes.

One method to register a pair of fluoro shots to an optical tracking system is to utilize a fixture 21001 (also referred to as a fluoro fixture) that is attached to the detector 3005 (also referred to as an image intensifier) of the fluoroscopy system of FIG. 22. As shown in FIG. 20, this fixture 21001 has optical tracking markers 21005 (e.g. reflective spheres or light-emitting diodes) used by the optical tracking system to track its position relative to the patient, and the fixture 21001 has multiple arrays of metal spheres (BBs) or other radio-opaque fiducials that are dispersed/embedded in at least two planes to create a pattern of x-ray shadows on the fluoroscopic images/shots. In the example of FIG. 20, a first BB plane 21009a is spaced apart from the detector 3005, and a second BB plane 21009b is mounted adjacent the detector 3005 so that the second BB plane 21009b is between the first BB plane 21009a and the detector 3005. The BBs of FIG. 20 are not visible, but are embedded in a radiolucent material comprising the respective BB planes so that each BB blocks x-rays to provide a respective shadow in a fluoroscopic image generated using detector 3005. The positions of the fluoroscopic fixture's optical tracking markers 21005 are captured by the optical tracking system at the time the fluoroscopic shot/image is taken, allowing the location of the image plane of detector 3005 to be accurately tracked. From image processing, the shadows created by the BBs and cast on the image plane allow the location of the source 3001 to be accurately determined using the geometric constraints of a pinhole camera model as shown in FIG. 21.

FIG. 20 illustrates a Globus fluoroscopic registration fixture 21001. The fixture 21001 clamps on to the x-ray detector 3005 (e.g., image intensifier) of a C-arm fluoroscopy system. Six reflective spheres 21005 are used to provide optical tracking by the optical tracking system and two BB planes 21009a and 21009b comprised of black plastic (with 161 BBs embedded therein) are shown.

Figure 21:
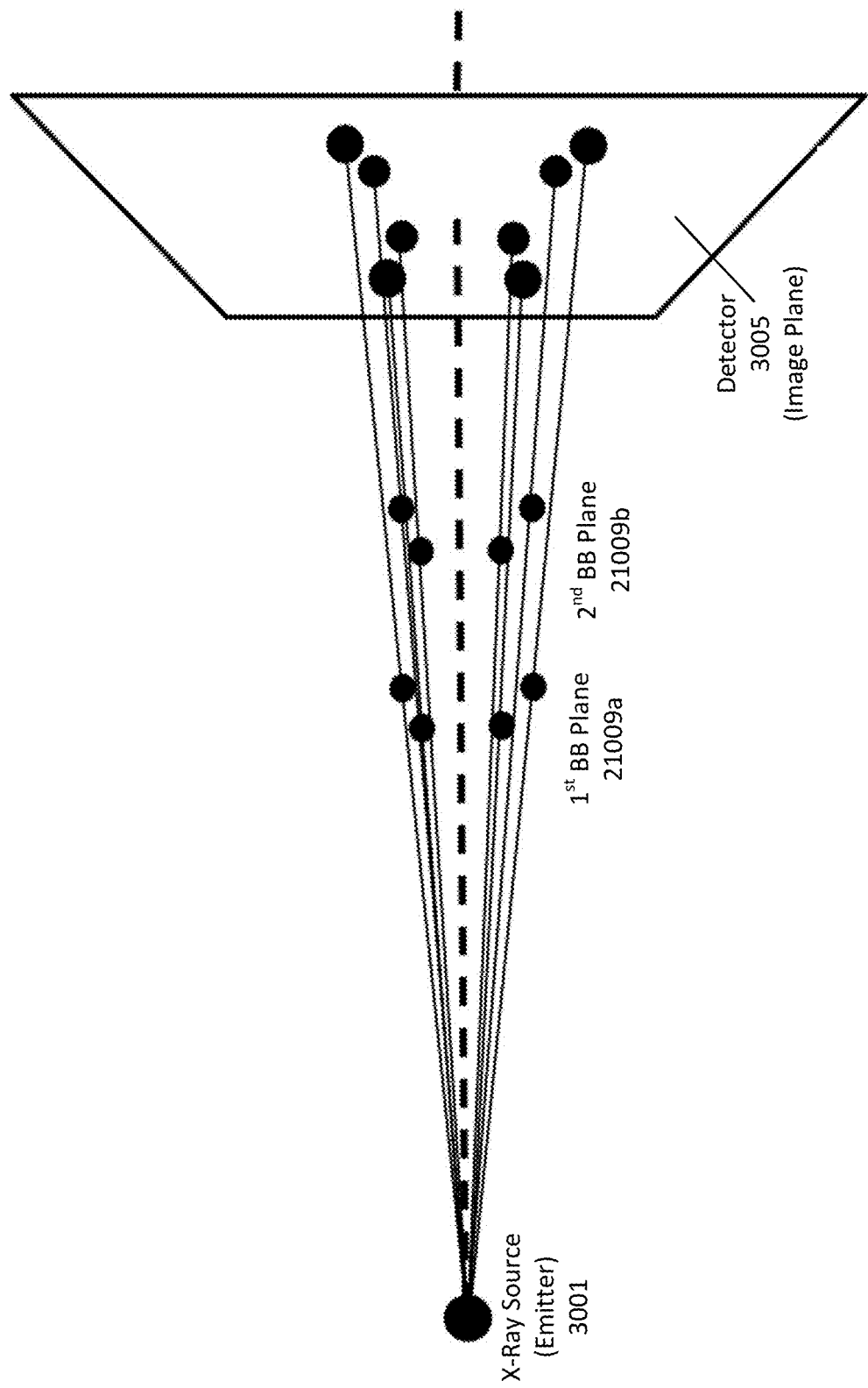
FIG. 21 is a schematic diagram illustrating a pinhole camera model.

FIG. 21 is a schematic diagram illustrating concepts of a pinhole camera model. X-rays from a point source (i.e., x-ray source 3001, also referred to as an x-ray emitter, an emitter, or a source) travel through tissue (between x-ray source 3001 and 1st BB plane 21009a) until reaching the detector 3005 (image intensifier), where the image is generated. If the spacing between BBs and planes is known, the pattern of the x-ray shadows projected on the 2D image plane of detector 3005 dictates where the x-ray source 3001 must have been located relative to the detector 3005 to create the shot.

With the location of the source 3001 and detector 3005 accurately determined in camera space (of the optical tracking system), it is possible to exactly define the mathematical transformations to move back and forth between camera space (of the optical tracking system) and the 2D image planes (one plane of each of the pair of fluoroscopic images). For example, if an object is in a known location in camera space, its projection's representation can be rendered onto each image plane exactly where the object's projections would appear as if a new pair of fluoroscopic images/shots were taken from the same orientations of the C-arm 3009, source 3001, and detector 3005. Conversely, if an object's projections are added to the two 2D image planes (like a projected screw image added to the surgical plan on antero-posterior (A-P) and lateral fluoroscopic images/shots), the 3D location of the object in camera space can be exactly determined. Note that there are constraints on where an object's projected image can be placed on the two 2D image planes simultaneously to be in a valid location that would correctly project simultaneously on both images. Consider the analogy of looking at a point in space from front and side perspectives. From a front perspective, it is unclear how far toward the front or back that point is located, but it is certain where from left to right and up to down the point is located. Looking at the same point from the side, it is unclear how far toward the left or right of the 3D (3-dimensional) space that point is, but it is certain where from front to back and up to down the point is located. If moving the 2D (2-dimensional) position of the point as viewed from the front perspective, it is allowed to go anywhere from left to right and the point location would be unchanged from the side perspective, but it cannot be at a different position up to down unless the position of the point on the side perspective changes its up-down location to match.

Although the methods described above for using the tracked fixture 21001 of FIG. 20 and geometric constraints are effective in accurately determining the locations of the detector 3005 image plane and source 3001 in optical camera space to enable registration of fluoroscopic images/shots to the optical camera space, there may be shortcomings with this method. For example, it may be difficult to automatically locate or accurately locate the shadows of metal BBs (or other fiducials) of the fluoroscopic fixture 21001 in the presence of other shadows on the fluoroscopic image caused, for example, by metallic surgical implants. Some fluoroscopic images/shots may have dark regions of comparable contrast to the metal in the BBs or other fiducials. In such cases, the algorithm may be unable to find or use these fiducial shadows for registration and the accuracy of registration may be reduced or registration may not be possible.

Another shortcoming of methods using fixture 21001 is that the many BBs or other radio-opaque fiducials on fluoroscopic images must be present for registration, but the BBs may be undesirable to the surgeon who is using the images as a visual aid for surgery. For example, the BBs or other fiducials may obscure part of an anatomical structure that the surgeon needs to see clearly.

A further shortcoming of methods using fixture 21001 of FIG. 20 is that it may be difficult/impossible to collimate the fluoroscopic images if they are to be used in registration. Collimation is where lead shields are moved in from one or more sides of the x-ray source 3001 to prevent x-rays from reaching outer portions of the collector 3005 and appearing on the fluoroscopic image. Collimation may be useful when some of the x-rays go through tissue but other x-rays go through air only. For example, when taking a lateral fluoroscopic image/shot of a patient, the area to be visualized (torso) is very wide and deep but very short in the antero-posterior (A-P) direction (top to bottom). It may therefore be useful to collimate the x-ray image from the top (or top and bottom) to reduce/prevent the sharp change in image contrast between tissue and air that would otherwise be seen. However, the fluoroscopic images/shots for registration rely on being able to visualize enough fiducial BBs in each shot, and collimation would block some of the BBs.

A further shortcoming of methods using fixture 21001 of FIG. 20 is that the two planes of BBs that are used/required by the pinhole camera model to localize the source 3001 are bulky and obtrusive. Although one plane of BBs is flush against the face of x-ray detector 3005, the second plane typically must protrude outward at least 100 mm from the face of x-ray detector 3005 to achieve the desired accuracy in source 3001 localization. This protrusion of the outer BB plane may make it difficult to get the fluoroscopic unit close enough to the patient. The farther the fluoroscopic unit is from the patient, the more magnified the fluoroscopic image appears due to parallax (resulting in a narrower field of view). Because of this limitation, the fluoroscopic image may be more magnified than the surgeon wants, encompassing, for example, only one spinal level instead of two.

All of the issues discussed above stem from the usage of two planes of BBs in the calibration algorithm, and so it may be beneficial to eliminate the need for multiple planes of BBs. Instead of using detected BBs in the above method to determine locations of the detector 3005 image plane and source 3001, the position of the source 3001 may be extrapolated based on the location of an optical tracker mounted to the detector 3005 (image intensifier). However, the source 3001 position cannot be accurately extrapolated because the C-arm 3009 of the fluoroscopy system may flex a small amount when it is in different orientations since the x-ray detector 3005 (image intensifier or flat panel), source 3001 (emitter/anode), and C-arm 3009 itself are somewhat heavy pieces of equipment. Due to flexing of the C-arm 3009, the location of the source 3001 relative to the detector 3005 may vary by several millimeters between typical positions of the C-arm 3009 such as anteroposterior A-P and lateral, creating an unacceptable inaccuracy in the predicted location of the source 3001 that is used for the registration.

According to some embodiments of inventive concepts, instead of using projections of fixture fiducials and geometric constraints of a pinhole camera model to determine the location of the x-ray source 3001, the current monitored orientation of the C-arm 3009 is used to accurately predict how the C-arm 3009 flexes and therefore accurately determine where the source 3001 is located. There are several different ways to monitor the orientation of the C-arm 3009 and several ways to use this information to determine a location of source 3001, as will be discussed below.

One way to monitor orientation of C-arm 3009 is to read the values of the C-arm axes automatically or manually and to provide these values to an algorithm that utilizes them to determine the effect on source 3001 location. Typically, C-arm 3009 has three rotational movements: orbit (Rz), tilt (Rx), and wig-wag Ry as shown in FIG. 22. There are additionally some linear translational axes on C-arm 3009. Since the wig-wag axis Ry is nearly exactly aligned with gravity it can be assumed that there will be no difference in how the C-arm 3009 flexes due to change in wig-wag Ry. Also, the linear translational positions Tx and Ty should not affect how the C-arm 3009 flexes. Therefore, changes in source 3001 position can be characterized relative to detector 3005 position knowing primarily the changes in orbit Rz and tilt Rx.

FIG. 22 illustrates a configuration of a fluoroscopy system showing different movement axes, including tilt Rx, In-Out Tx, Up-Down Ty, Wig-Wag Ry, and Orbit Rz. The axis about which Wig-Wag occurs (shown as Ry) is typically aligned with gravity unless operating the C-arm 3009 on a slope, and therefore only orbit Rz and tilt Rx should significantly affect how the C-arm 3009 flexes under normal conditions.

Older C-arm fluoroscopy systems have locking and unlocking mechanisms to allow orbit Rz and tilt Rx to be changed manually, and have a scale indicating within +/−1 degree the position of each axis. A software user interface could therefore allow these values to be entered by the user each time a fluoroscopic shot is taken and would use these values to calculate offset of the source 3001 relative to detector 3005. Alternately, axes of the C-arm 3009 could be fitted with optical, magnetic, or other encoders to automatically detect the position of each axis and feed this information to the navigation system for processing.

Newer C-arm fluoroscopy systems have built-in encoders to record the position of each axis digitally. These systems store the axis coordinates to onboard memory and additionally write the coordinates in the DICOM (Digital Imaging and Communication in Medicine) header of each fluoroscopic image that is taken. Software could therefore use a digital data stream through serial cable or other means between the C-arm fluoroscopy system and navigation system to communicate the current axis positions, especially the orbit Rz and tilt Rx, during fluoroscopic shots. Or, software could retrieve each image/shot as a DICOM file, through Ethernet, serial communication, or wireless data transfer, and read the DICOM tags through standard software methods to retrieve information about the orbit Rz and tilt Rx positions.

Another way of monitoring the orientation of the C-arm 3009 is to place electronic tilt sensors or an inertial measurement unit (IMU) at some location on the C of the C-arm 3009 to monitor its angular orientation and to feed this information to the navigation system while fluoroscopic shots are taken.

Two tilt sensors would be used to monitor the offset in the C-arm 3009 corresponding to orbit Rz and tilt Rx. IMUs typically monitor 3 or 6 degrees of freedom and would be oriented when they are mounted on the C-arm 3009 such that the gravitational direction is initially aligned with the vertical axis of the IMU while the C-arm 3009 is in the reference position. Data from tilt sensors and/or IMUs would then be communicated to the navigation system at the time a fluoroscopic shot is taken for registration via Ethernet, WiFi, Bluetooth, serial port, or any suitable means.

Another way to monitor the orientation of a C-arm 3009 during different shots is to utilize the optical tracking system that is already being used to track the location of the detector 3005 (also referred to as a collector). Doing so would require the system to first define the vertical direction for the system, and to maintain this definition subsequently. For example, a software feature could prompt the user to position the C-arm 3009 with orbit Rz at 0° and tilt Rx at 0° and then hit a button to capture this upright position. Subsequent measurements of the optical tracker on the C-arm 3009 would then be able to determine the change in orientation as long as the cameras of the optical tracking system had not moved. Or, if the optical tracking cameras did move, the vertical direction could still be deduced if an additional tracked reference fixture that indicates the direction of gravity is also viewed, such as tracking markers affixed to a table or other feature that does not change its orientation relative to gravity during the case.

A different embodiment to monitor the orientation of the C-arm 3009 during different shots is to utilize a gravity vector including optical tracking elements such as reflective spheres. Such a gravity vector could be positioned in close proximity to the fixture used to track the position of the detector 3005 and would only require an additional two markers, tracked as individual strays. If using reflective spheres, the two spheres forming the gravity vector could be connected to a base by a swiveling feature and weight could be added distal to the second sphere to force the two spheres to hang in the direction of gravity as shown in FIG. 23A, FIG. 23B, FIG. 23C, FIG. 24A, and FIG. 24B. This embodiment may be useful relative to using manual or automatic axis entry and/or relying on the tracked fixture orientation to determine C-arm 3009 position because it is less subject to user error. That is, methods using a gravity vector may be automatic with minor additional equipment used/needed and such methods do not require user input or maintenance of communication of other data streams.

Figure 23C:
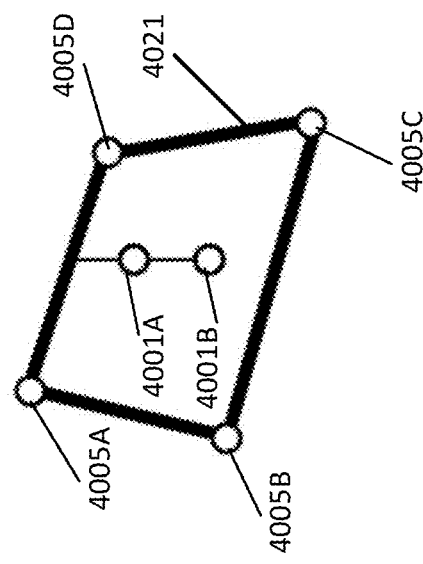
FIGS. 23A, 23B, and 23C are diagrams illustrating a gravity vector according to some embodiments of inventive concepts.
Figure 23B:
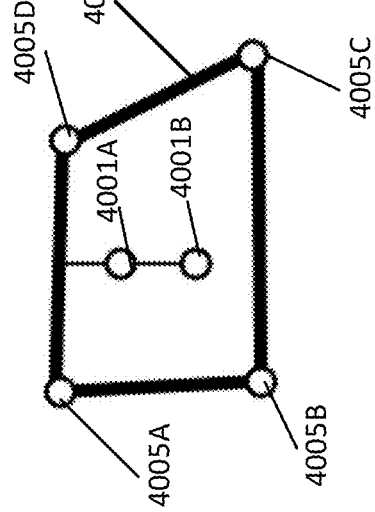
Figure 23A:
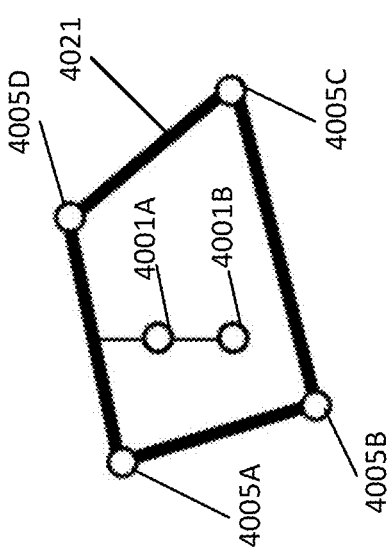

FIGS. 23A, 23B, and 23C illustrate a gravity vector including two additional reflective tracking markers 4001A and 4001B adjacent to or within the space occupied by a 4-marker C-arm tracker (including four reflective tracking markers 4005A, 4005B, 4005C, and 4005D) that is used to track a position of detector 3005. Three angular positions of the C-arm 3009 are represented and it is demonstrated how the gravity vector changes its orientation relative to the fixture's coordinate system at the different positions. The gravity vector includes two reflective tracking spheres 4001A and 4001B connected by a rigid or non-rigid linkage and connected to the base (frame of the fixture's tracker in this example) by a freely swiveling interface such as string or ball joint. The distal tracking sphere 4001B may be weighted or an additional weight may be attached distal to the tracking sphere 4001B to provide/ensure that it hangs vertically in alignment with gravity.

Figure 24A:
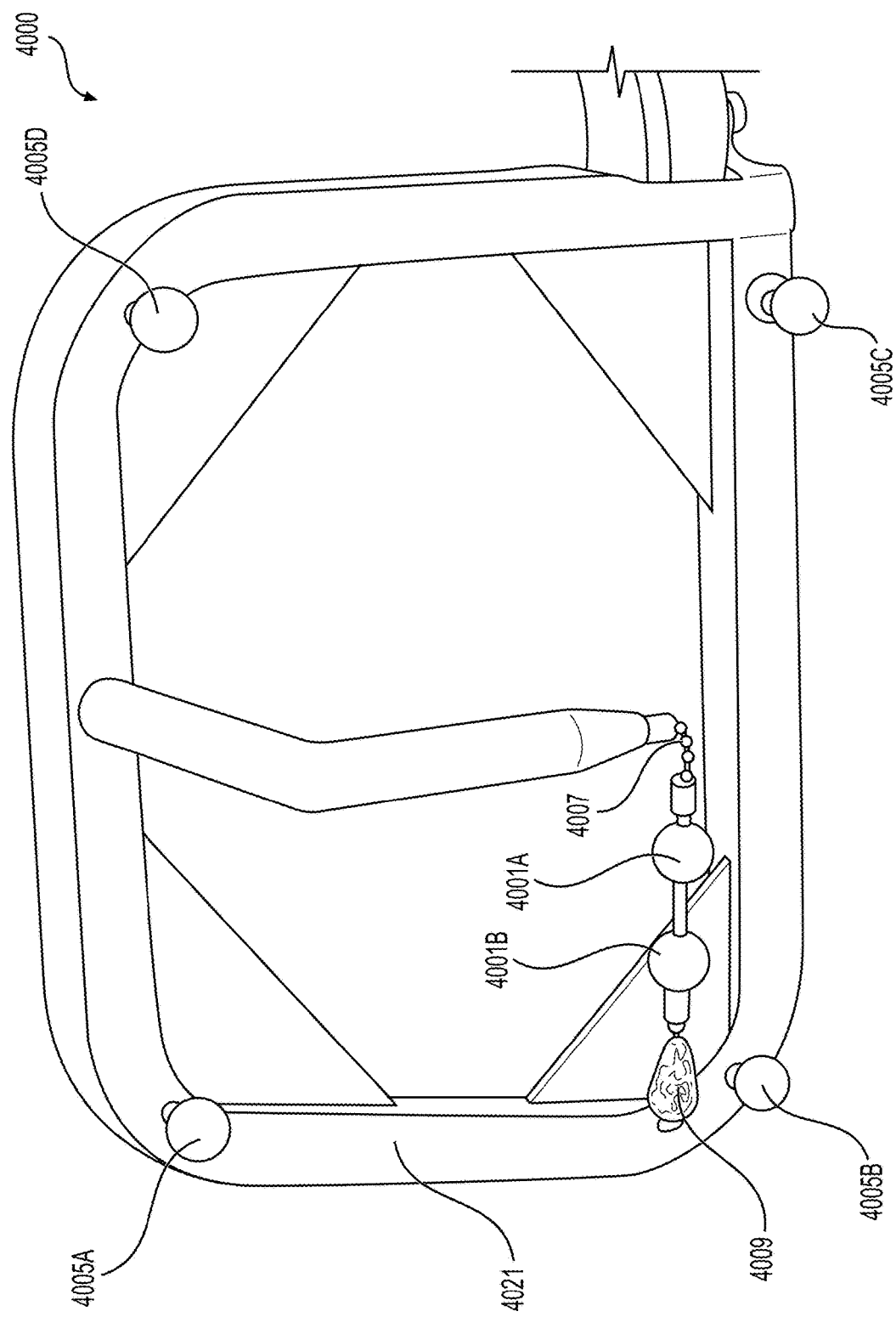
FIGS. 24A and 24B are photographs illustrating a gravity vector according to some embodiments of inventive concepts.
Figure 24B:
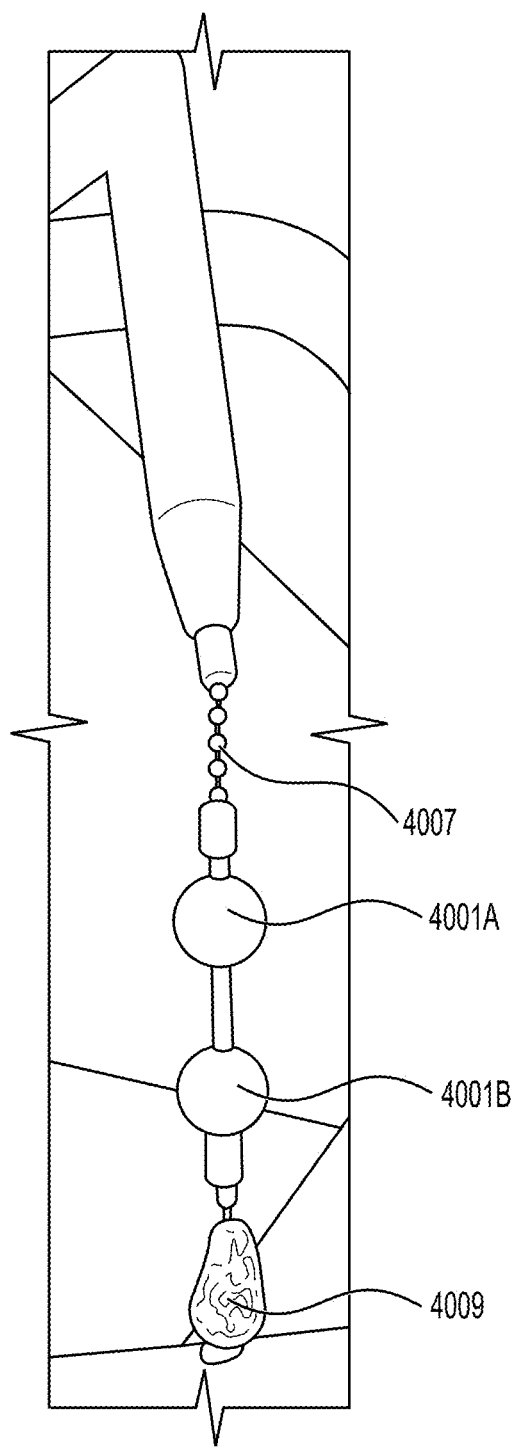

FIGS. 24A and 24B are photographs of a detector fixture 4000 including a gravity vector with tracking markers 4001A and 4001B mounted on a frame 4021 with optical/reflective tracking markers 4005A, 4005B, 4005C, and 4005D. The swiveling feature in this example is a chain 4007 similar to those used for lamp pull cords. This design may be preferred because the chain 4007 is free to rotate about its long axis while also bending at linkage points, and is therefore not likely to snag or get hung up in moving to a new orientation. A fishing weight 4009 was also attached distal to the distal tracking sphere 4001B of the gravity vector. As discussed below with respect to FIG. 27A, the detector fixture may be permanently mounted to the detector 3005 and/or to a portion of the C-arm 3009 adjacent to detector 3005. For example, the detector fixture may be mounted to the detector 3005 and/or to a portion of the C-arm 3009 in a manner that the detector fixture is outside a path of x-rays between the source 3001 and detector 3005.

One potential issue with a gravity vector such as is described above is that the two spheres connected by a swivel joint may continue to swing for an undesirably long time after moving the C-arm 3009 into a new position, forcing the user to waste time before continuing the registration process. According to some embodiments, damping the movement of the gravity vector may be achieved by connecting the spheres 4001A and 4001B to the base using a fluid-filled ball joint with small pores or channels in features of the joint that allow joint movement but only at the rate that fluid (e.g., water or oil) can flow through the pores. According to some other embodiments, a series of two perpendicular damped hinge joints, one corresponding to orbit Rz and one corresponding to tilt Rx, could be used to achieve the same behavior. Each hinge joint could be damped using known methods such as a dashpot across the joint like the mechanisms that control the rate at which household doors close.

Based on the detected orientation of the C-arm 3009 by any of the techniques described above at the time a fluoroscopic shot was taken, the system would utilize a calibration to determine the location of the source 3001. Such a calibration could be done at the time the fluoroscopic tracker is mounted on the fluoroscopic unit. In some embodiments, a series of operations would be followed to calibrate and then determine precise locations of source 3001 and detector 3005 as discussed below with respect to the flowchart of FIG. 25.

Figure 25:
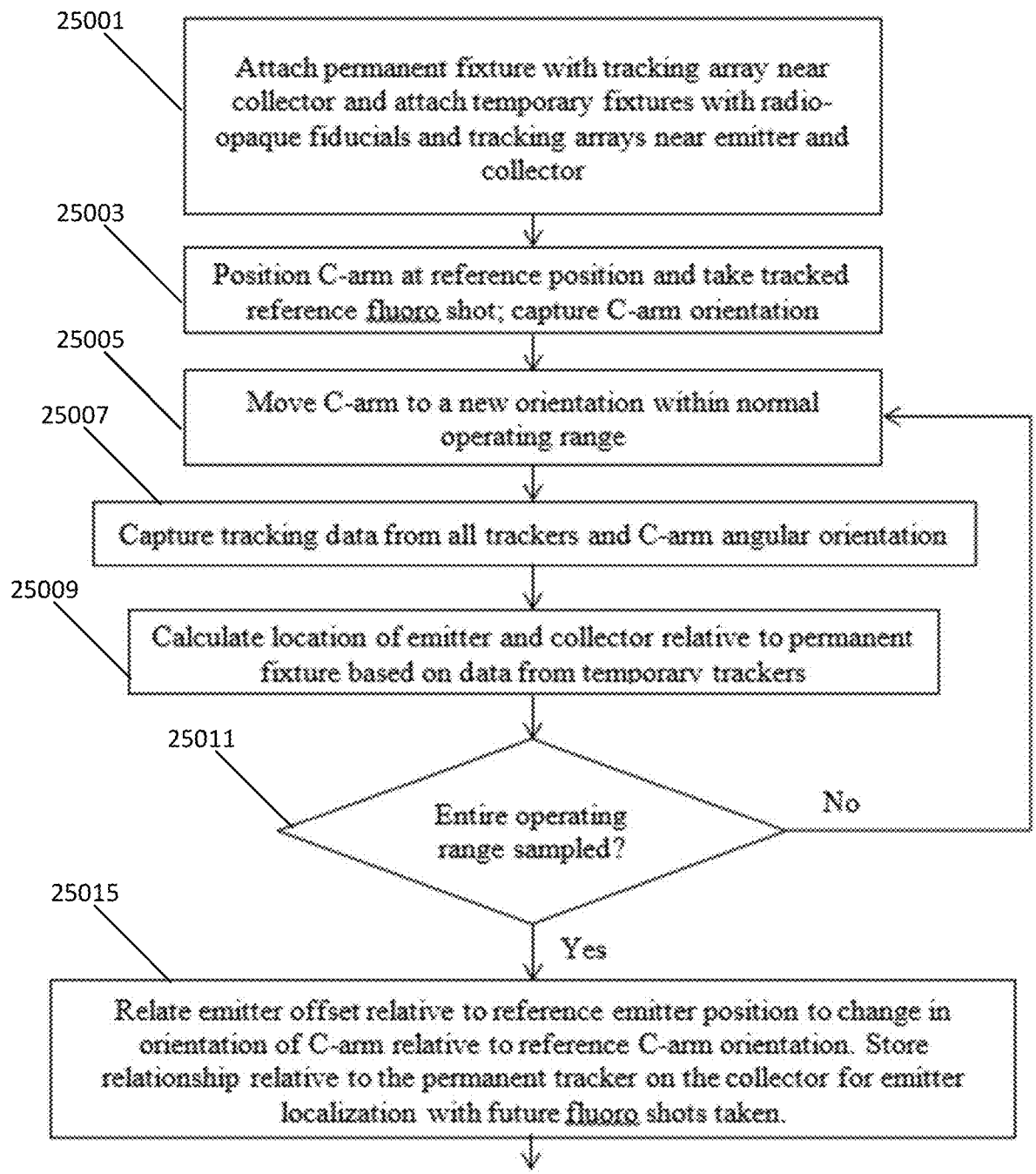
FIGS. 25 and 26 are a flow charts illustrating calibration operations according to some embodiments of inventive concepts.

FIG. 25 is a flow chart showing the operations to establish a calibration to facilitate adjustment to the extrapolated source 3001 location based on knowledge of C-arm 3009 orientation according to some embodiments of inventive concepts. After completing the calibration, the temporary fixtures can be removed and the offset in source 3001 position of any new fluoroscopic shot can be determined from the stored relationship and the tracked gravity vector. According to some embodiments of FIG. 25, fixtures of FIGS. 27A, 27B, and 27C may be used, and the gravity vector of FIG. 27A may be omitted.

Figure 27A:
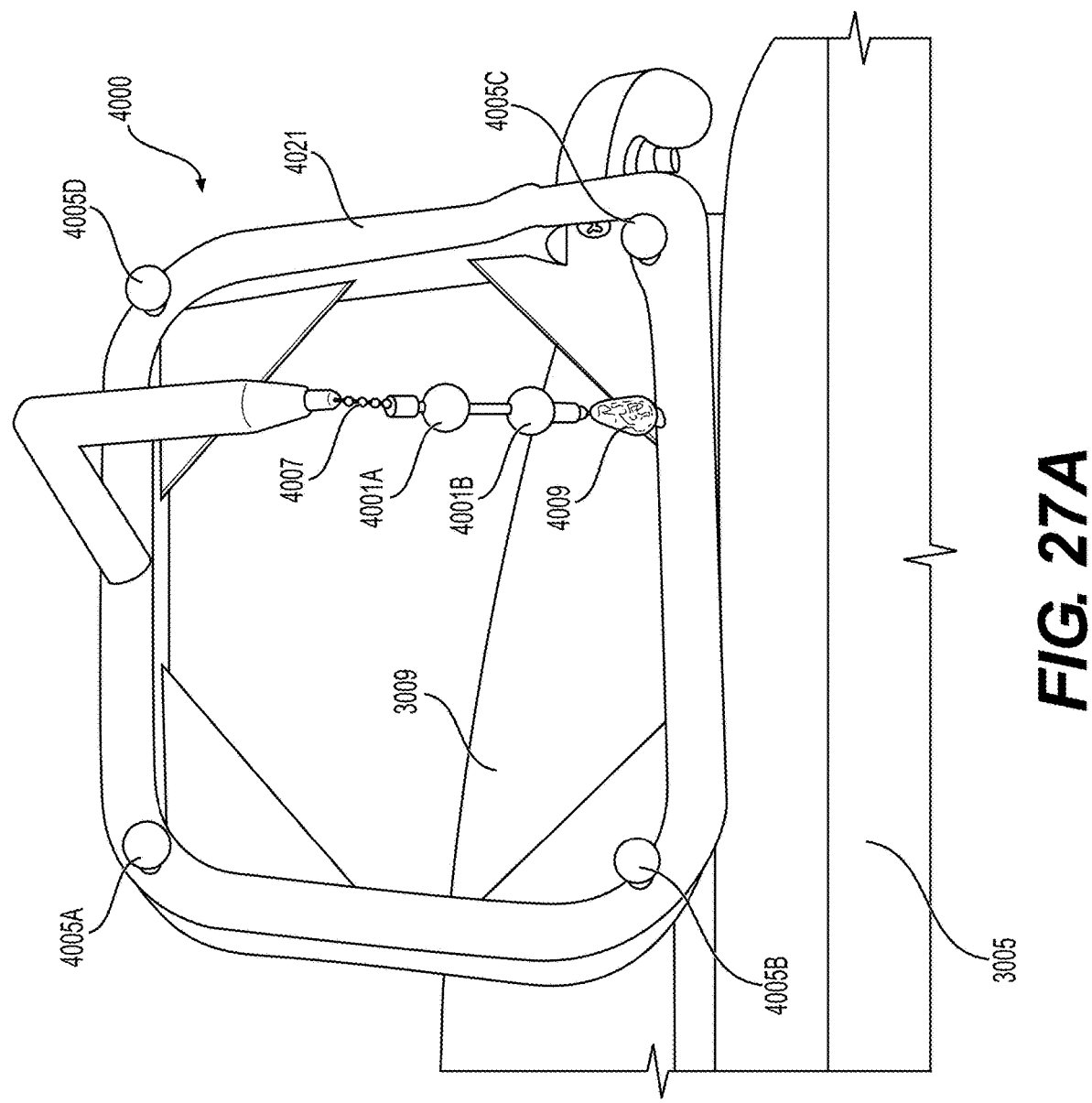
Figure 27B:
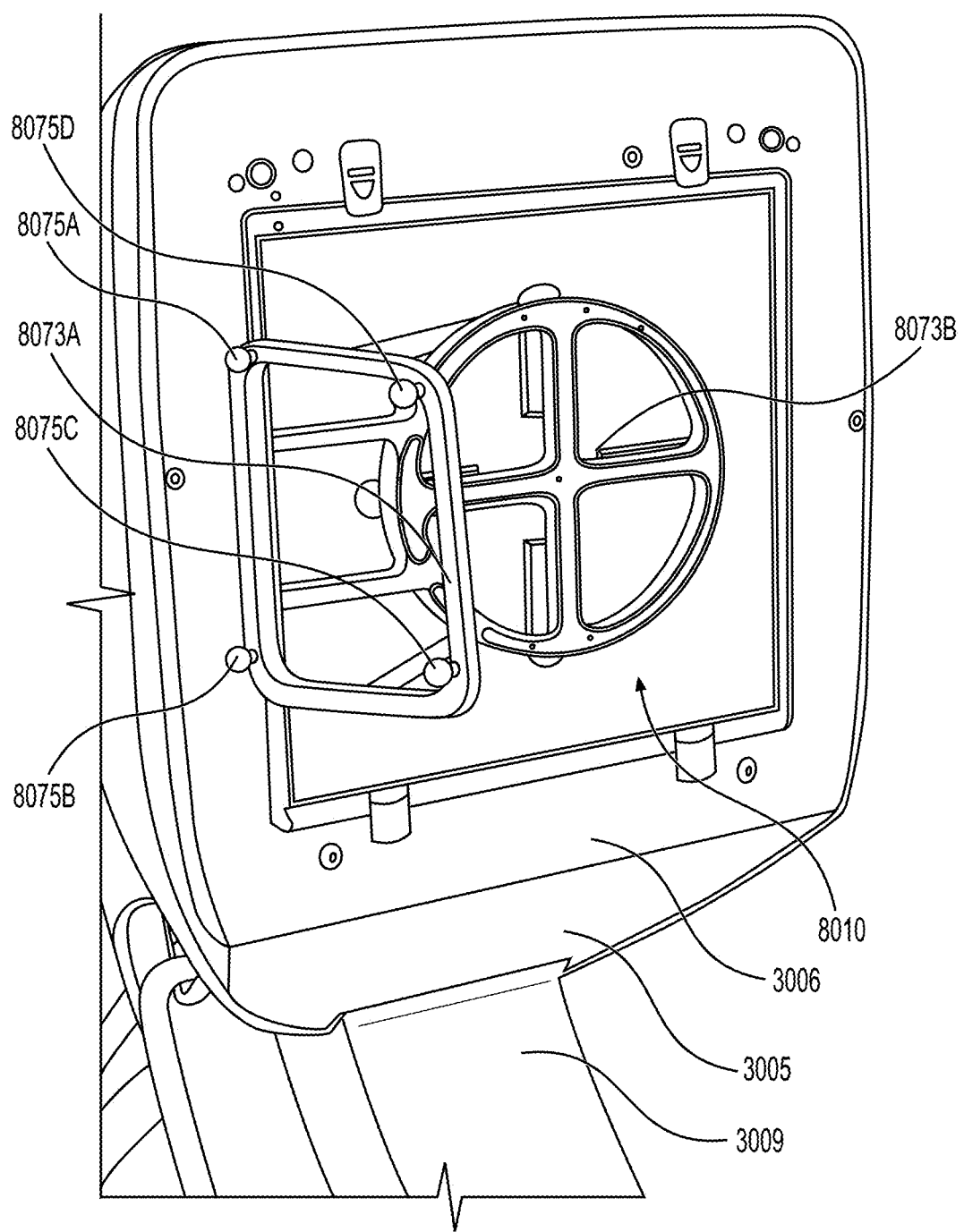

At block 25001, a permanent fixture 4000 with a tracking array (including markers 4005A-D) is attached near x-ray detector 3005 (also referred to as a collector) as shown in FIG. 27A, and temporary fixtures 8010 and 8050 with radio-opaque fiducials and tracking arrays are attached near x-ray source 3001 (also referred to as an emitter) and x-ray detector 3005 as shown in FIGS. 27B and 27C.

At block 25003, C-arm 3009 is positioned at the reference position, and a tracked reference fluoroscopic shot is taken while capturing the orientation of C-arm 3009. Accordingly, positions/orientations of x-ray source 3001, x-ray detector 3005, and C-arm 3009 are determined based on tracking arrays of fixtures 4000, 8010, and 8050 for the reference position.

At block 25005, C-arm 3009 is moved to a new orientation within the normal operating range.

At block 25007, tracking data from all tracker arrays (i.e., tracking arrays defined by markers 4005A-D, markers 8075A-D, and markers 8053A-D) and an angular orientation of C-arm 3009 are captured.

At block 25009, locations of x-ray source 3001 and x-ray detector 3005 are calculated relative to permanent fixture 4000 based on data from the temporary tracking arrays of fixtures 8010 and 8050.

At block 25011, operations of blocks 25005, 25007, and 25009 are repeated until data is collected for orientations of C-arm 3009 taken over an entire operating range of C-arm 3009.

At block 25015, the x-ray source 3001 offset relative to reference x-ray source 3001 position (from block 25003) is related to a change in orientation of C-arm 3009 relative to the reference orientation of C-arm 3009 (from block 25003), and the relationships relative to the tracking array of permanent fixture 4000 are stored for x-ray source 3001 localization with future fluoroscopic shots taken.

Figure 26:
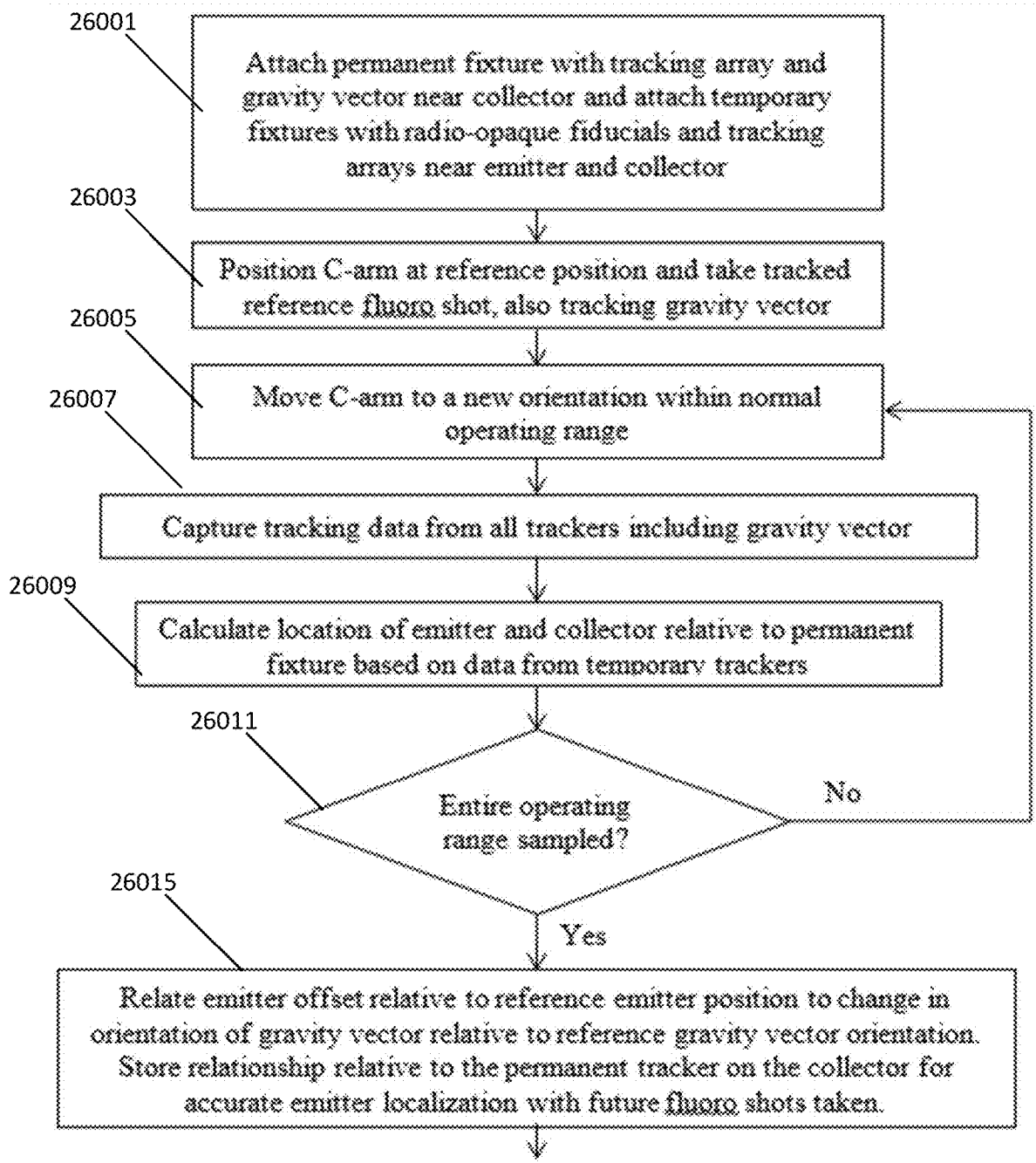

FIG. 26 is a Flow chart for specific usage of an embodiment with gravity vector (e.g., using fixture 4000 of FIG. 27A with the gravity vector). If the method used to determine C-arm orientation is the gravity vector, the flow chart of FIG. 25 can be expressed instead as the flow chart of FIG. 26.

At block 26001, a permanent fixture 4000 with a tracking array (including markers 4005A-D) and gravity vector (including markers 4001A-B) is attached near x-ray detector 3005 (also referred to as a collector) as shown in FIG. 27A, and temporary fixtures 8010 and 8050 with radio-opaque fiducials and tracking arrays are attached near x-ray source 3001 (also referred to as an emitter) and x-ray detector 3005 as shown in FIGS. 27B and 27C.

At block 26003, C-arm 3009 is positioned at the reference position, and a tracked reference fluoroscopic shot is taken while capturing orientations of C-arm 3009 and gravity vector. Accordingly, positions/orientations of x-ray source 3001, x-ray detector 3005, C-arm 3009, and gravity vector are determined based on tracking arrays of fixtures 4000, 8010, and 8050 for the reference position.

At block 26005, C-arm 3009 is moved to a new orientation within the normal operating range.

At block 26007, tracking data from all tracker arrays (i.e., tracking arrays defined by markers 4005A-D, markers 8075A-D, and markers 8053A-D) and the gravity vector are captured.

At block 26009, locations of x-ray source 3001 and x-ray detector 3005 are calculated relative to permanent fixture 4000 based on data from the temporary tracking arrays of fixtures 8010 and 8050.

At block 26011, operations of blocks 26005, 26007, and 26009 are repeated until data is collected for orientations of C-arm 3009 taken over an entire operating range of C-arm 3009.

At block 26015, the x-ray source 3001 offset relative to reference x-ray source 3001 position (from block 26003) is related to a change in orientation of gravity vector relative to the reference gravity vector orientation (from block 26003), and the relationships relative to the tracking array of permanent fixture 4000 are stored for x-ray source 3001 localization with future fluoroscopic shots taken.

Example embodiments of the permanent and temporary fixtures that are attached to the C-arm 3009, detector 3005, and/or source 3001 that are mentioned in the first operation of FIG. 25 and/or FIG. 26 are shown in FIGS. 27A, 27B, and 27C.

FIG. 27A illustrates a permanent detector fixture 4000 according to the structure shown in FIGS. 24A and 24B mounted to a portion of C-arm 3009 adjacent an upper surface of detector 3005, such that detector 3005 is between the detector fixture 4000 and the source 3001. Accordingly, the permanent detector fixture 4000 does not obstruct a path of x-rays from source 3001 to detector 3005.

FIG. 27B illustrates a temporary detector fixture 8010 mounted on a face 3006 of detector 3005 between the detector 3005 and source 3001.

FIG. 27C illustrates a temporary source fixture 8050 mounted on source 3001 between source 3001 and detector 3005. As shown, source fixture 8050 includes a frame 8051 and a plurality of optical tracking markers 8053A, 8053B, 8053C, and 8053D.

FIGS. 27A, 27B, and 27C thus illustrate fixtures used to calibrate the fluoroscopic imaging system, based on optical tracking using the optical tracking markers 4005A, 4005B, 4005C, 4005D, 8053A, 8053B, 8053C, 8053D, 8075A, 8075B, 8075C, and 8075D (e.g., provided as optically reflective spheres).

As shown in FIG. 27A, permanent detector fixture 4000 is attached on/near the detector 3005. In this example, the permanent detector fixture 4000 also has a gravity vector (including optical tracking markers 4001A and 4001B and weight 4009) attached to its frame 4021, and optical tracking markers 4005A, 4005B, 4005C, and 4005D (e.g., provided as reflective spheres).

As shown in FIG. 27B, temporary fixture 8010 is attached on/near the imaging plane of detector 3005. Fixture 8010 has a tracking array including a portion 8073A of frame 8073 that extends perpendicular from face 3006 of detector 3005 and optical tracking markers 8075A, 8075B, 8075C, and 8075D on frame portion 8073A. Fixture 8010 also includes a plane of BBs in a portion 8073B of frame 8073 that is flat against and parallel to the face 3006 of detector 3005 so that the plane of BBs and portion 8073B of the frame are between detector 3005 and source 3001. The optically tracking array (including optical tracking markers 8075A, 8075B, 8075C, and 8075D) is thus in a known/fixed location relative to the BB plane because this tracking array and the BBs of this plane are both affixed to and/or provided in/on the same rigid frame 8073, thereby allowing the position of the BB plane (and the positions of the BBs therein) to be accurately tracked using the optical tracking array.

As shown in FIG. 27C, temporary fixture 8050 is attached near the source 3001 (e.g., between the source 3001 and detector 3005). The fixture 8050 has a tracking array (including optical tracking markers 8053A, 8053B, 8053C, and 8053D) and also a plane of BBs 8055 (also referred to as an x-ray opaque fiducial pattern) embedded in frame 8051 between source 3001 and detector 3005. The tracking array (including optical tracking markers 8053A, 8053B, 8053C, and 8053D) is in a known location relative to the BB plane 8055 because both are affixed to and/or provided in/on the same rigid frame 8051, thereby allowing the position of the BB plane 8055 (and the positions of the BBs therein) to be accurately tracked using the optical tracking array. The BB plane 8055 is perpendicular to the path of x-rays (from source 3001 to detector 3005) and a few inches away from the x-ray source 3001.

Figure 28:
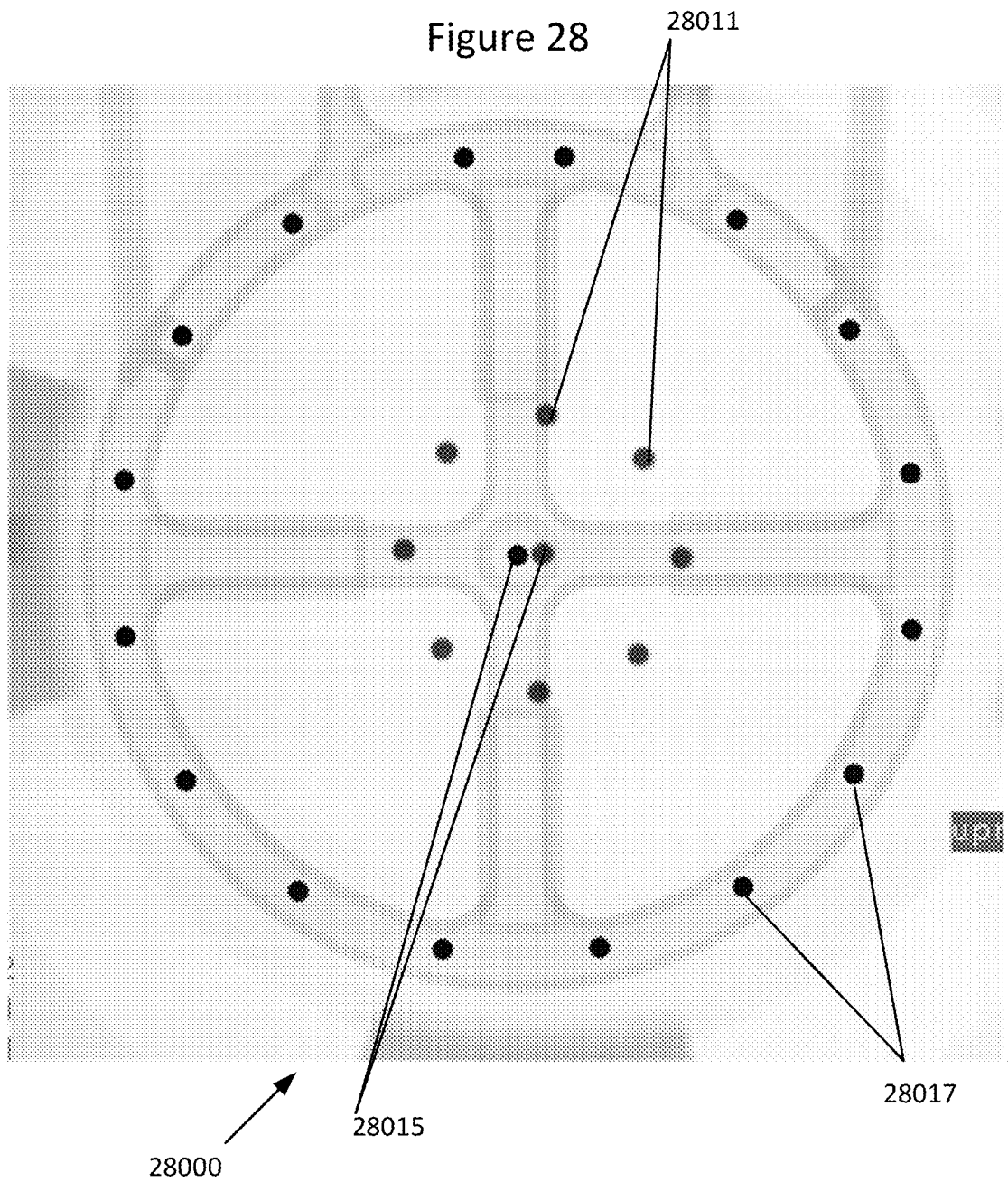
FIG. 28 is a photograph illustrating a reference fluoroscopic image/shot as discussed with respect to FIG. 25 according to some embodiments of inventive concepts.

FIG. 28 illustrates an embodiment of the reference fluoroscopic image/shot described in FIG. 25 (operation 25003) or FIG. 26 (operation 26003) that could be the standard position for an anteroposterior shot, with detector 3005 above the procedure table and the source 3001 below the procedure table. This position is typically labeled as 0° tilt Rx and 0° orbit Rz in standard fluoroscopic C-arm systems. A pinhole camera model constraint would be applied to the fluoroscopic image/shot taken in the reference position (operation 25003 or 26003) to accurately locate the source 3001 based on the projections of the BBs from BB plane 8055 of fixture 8050 on source 3001 and based on the projections of BBs from the BB plane of fixture 8010 on detector 3005. The distance between BB planes, required by the pinhole camera model, would be tracked using optical tracking markers (8075A, 8075B, 8075C, 8075D, 8053A, 8053B, 8053C, and 8053D) on the fixtures 8010 and 8050. Methods for applying projection constraints to data sets are known in the field and are available through open-source software such as OpenCV (open source computer vision, http://openCV.org). Since the reference fluoroscopic shot is for calibration purposes only, the fluoroscopic shot may be taken without anything in the field between fixtures 8010 and 8050. By taking such an "air shot", it can be provided/ensured that good image contrast will be achieved and that image processing will be able to detect the BB shadows effectively as shown in FIG. 28.

FIG. 28 illustrates an example of a fluoroscopic x-ray air image/shot 28000 taken with temporary fixtures 8010 and 8050 respectively attached to detector 3005 and source 3001. The inside ring of BB shadows 28011 and inner BB shadows 28015 are from the BBs of source fixture 8050 and the outside ring of BB shadows 28017 is from the detector fixture 8010. The BBs near the source 3001 (included in fixture 8050) have a diameter that is 32% of the diameter of BBs near the detector 3005 (included in fixture 8010) but the BB shadows appear roughly the same size due to parallax during projection. Lighter shadows are from the frame 8073 of fixture 8010.

An orientation of the gravity vector (also referred to as a gravity vector value) of FIG. 27A (including optical tracking markers 4001A and 4001B) could be displayed as a unit vector with X, Y, and Z components and the gravity vector value can be updated continually by software to monitor the current orientation of the C-arm 3009. This real-time gravity vector value could be used as a motion-sensing control feature. If the gravity vector is not static, then the C-arm is still in motion or the gravity vector is still swinging after the last movement. Sensed motion of the gravity vector can therefore be used to reduce/prevent/limit unusable fluoroscopic shots from being taken or acquired by the frame grabber through software. The orientation of the gravity vector (i.e., the gravity vector value) can also be recorded for reference, and this reference value utilized in the same or different surgical cases to help guide the user to a particular angular orientation or angular increment from a previous orientation of the C-arm. For example, if the gravity vector pointed a particular direction for one fluoroscopic shot that was later found to be ineffective in registration and the user wished to try a new C-arm orientation that was exactly 10° different from the previous orientation, the stored value of the gravity vector could help precisely find the new position by showing and comparing the current and previous gravity vector. Software could also display the calculated angular difference between the previous and current gravity vector values, taken as the arccosine of the vector dot product of the two unit vectors.

In the loop of FIG. 25 or the loop of FIG. 26, the C-arm 3009 would be swung through its standard operating range of positions while tracking the marker arrays on fixtures of FIGS. 27A, 27B, and 27C and the gravity vector (or C-arm orientation by whatever means is used). It is important that the gravity vector, if used, does not move into any position where it hangs up on itself or another part of the fixture, or is for any reason unable to hang freely with gravity during the range studied. The attachment to the gravity vector may therefore be designed in such a way that it hangs down when in the most common orientation and is 180° inverted in the least common orientation. The least common orientation would likely be with the x-ray detector 3005 positioned under the procedure table. This orientation is unlikely because the tracking array (i.e., including the optical tracking markers 4005A, 4005B, 4005C, and 4005D in the fixture of FIG. 27A) on the detector 3005 may not be visible in such an orientation.

In collecting data for the useable range of orientations of the C-arm 3009, enough samples should be collected that the relationship between the orientation of C-arm 3009 and source 3001 offset (relative to detector 3005) is well characterized. The primary data to be sampled are the source 3001 and detector 3005 locations, which were established relative to their tracking arrays in the reference shot. Additional fluoroscopic x-ray shots are not needed because the tracking arrays should equally or more accurately locate the source 3001 and detector 3005 than projection data.

With sampled data at different orientations of C-arm 3009 (also referred to as C-arm orientation), the relationship between source 3001 offset and C-arm orientation must be established. There are different ways to establish this relationship. One way is to use an interpolative lookup table, where different angular orientations corresponding to orbit Rz and tilt Rx are tabulated along with the source 3001 offset in X, Y, and Z dimensions. Then, when a new fluoroscopic x-ray shot is taken at a particular orientation of C-arm 3009, the X, Y, and Z offsets are read from the lookup table. If there is no entry for the combination of orbit Rz and tilt Rx used, then the offsets are linearly or nonlinearly interpolated from the nearest available entries.

A different way to set the relationship between source 3001 offset and C-arm orientation is to make a physics model of the C-arm 3009. The physics model could be calibrated with material and geometric properties that precisely predict how the C-arm 3009 flexes at different orientations. The data collected when sampling at different orientations would be used to tune or optimize the model such that the model is able to generate accurate outputs when given a new orientation of C-arm 3009 for a new x-ray fluoroscopic shot that was not part of the tuning data set.

A third way to set the relationship between source 3001 offset and C-arm orientation is to utilize machine learning such as a neural network. The training data set would be the data collected during the sweeps of the C-arm 3009 and the corresponding source 3001 offsets. The accuracy of the neural network model in predicting source 3009 offset based on C-arm orientation would depend on how much data was provided to the neural network in its training.

Another method to establish the relationship between source 3001 offset and C-arm orientation is to fit a general function of two input parameters to an output that could be X, Y or Z Cartesian coordinate shift in the location of the source. The two input parameters i1 and i2 could be orbit Rz and tilt Rx angles or two components of a gravity vector (since a unit orientation vector has two degrees of freedom). Functions could therefore be written as:

$X = f1(i1, i2)$ $Y = f2(i1, i2)$ $Z = f3(i1, i2)$

Once calibrated, three such equations would fully define source 3001 shift as a function of the C-arm orientation. Sampled data could be used to fit each function through an appropriate computational method such as Levenberg-Marquardt Optimization. The form of the function to fit for such a process could be a sine-cosine relationship, polynomial model, Gaussian mixture model, or general curve with any number of degrees of freedom. In one example of an embodiment, a function could be fit for X, Y, and Z Cartesian coordinates based on i1 and i2 such that $X = p1*i1^2*i2 + p2*i1 + p3*i1^2 + p4*i2^2 + p5i1*i2 + p6*i1 + p7*i2 + p8$ where p1 through p8 are parameters solved through an optimization method, and with each parameter representing a weight of the contribution of a component to the function. Similar functions for Y and Z could be written, each with their own set of weights that are solved separately.

After completing the calibration procedure and logging the source 3001 offset through a range of C-arm orientations, the temporary fixtures of FIGS. 27B and 27C would be removed, leaving just the permanent fixture of FIG. 27A for actual usage during procedures/cases. During data collection, it could be provided/ensured that the relationship is established in reference to the permanent fixture of FIG. 27A. The offset from the permanent fixture to the temporary fixture on the detector 3005 should be fixed, so the relationship of detector 3005 location to the permanent array of FIG. 27A is easily determined/computed. The offset from the permanent fixture of FIG. 27A to the source 3001 in the upright location would have been captured in the second step of the flow chart of FIG. 25 or FIG. 26 and then the source 3001 offset would have been related to this position in the coordinate system of the permanent fixture of FIG. 27A during data collection to keep the relationship always in terms of the permanent fixture. Alternately, the permanent fixture of FIG. 27A could be added after the calibration is completed and an operation similar to our "registration transfer" described elsewhere could be used to transform the relationship that was previously in terms of the temporary fixture of FIG. 27B to be in terms of the permanent fixture of FIG. 27A, after which temporary fixtures are removed.

Instead of trying to relate the gravity vector to a particular tracking fixture, or designing tracking fixture attachments to ensure that fixtures always attach relative to each other in a reproducible way, the gravity vector could be stored and accessed as "normalized" values. For normalization, two specific orientations could correspond to reference positions. In one embodiment of the concept of normalization, the upright position of the C-arm 3009 could correspond to (0,0,1), or exact alignment with the Z axis, and the lateral position could correspond to (1,0,0), or closest alignment with the X axis. To achieve normalization of the gravity vector in practice, the C-arm 3009 would be put into the upright position and the gravity vector captured relative to any reference tracking fixture (FIG. 23A, 23B, 23C, 24A, 24B, or 27A). Then, the C-arm 3009 would be put into the lateral position and the gravity vector value captured relative to that position. In each position, the 3×3 rotation matrix to rotate from upright to that actual orientation would be recorded; that is, $R_0$ could represent the 3×3 rotation of the gravity vector relative to the fixture in upright position and $R_{90}$ could represent the 3×3 rotation of the gravity vector relative to the fixture in lateral position. If a unit vector g initially aligned with the z-axis g=(0,0,1) is rotated by $R_0$, a new vector $g_Z$ exactly aligned with gravitational Z would be described as:

$$g_Z = R_0 * g.$$

Similarly, if the same vector is rotated by $R_{90}$, a new vector $g_{Xa}$ approximately aligned with gravitational X would be described as:

$$g_{Xa} = R_{90} * g.$$

The cross product of these vectors (after normalization to a unit vector) would be a unit vector $g_Y$ exactly aligned with gravitational Y:

$$g_Y = g_Z \times g_{Xa}.$$

Crossing $g_Y$ and $g_Z$ gives a unit vector exactly aligned with gravitational X:

$$g_X = g_Y \times g_Z.$$

Therefore, using these vectors as columns of a 3×3 rotation matrix R gives the rotational transformation from the identity matrix to the normalized gravity vector orientation:

$$R = [g_X \, g_Y \, g_Z].$$

The inverse of this matrix $R_{inv}$, when applied to any gravity vector $g_F$ obtained relative to the tracking fixture, gives a normalized gravity vector:

$$g_N = R_{inv} * g_F.$$

Newer C-arm fluoroscopic systems utilize flat panel x-ray detectors, which create undistorted x-ray images. However, older C-arm fluoroscopic systems, which are still in service in many hospitals, utilize image intensifiers as x-ray detectors. Images created using older C-arm fluoroscopic systems may be subject to a greater amount of s-distortion and pincushion distortion than images created using flat panel x-ray detectors. The level of noise is substantial enough and unpredictable enough that raw images may lack the accuracy needed to detect source 3001 location using the pinhole camera constraints mentioned earlier. Raw images from image-intensifier-based detectors may therefore require an additional step to dewarp the images before processing them to be used in registration for any type of workflow such as fluoro-only or pre-op CT workflow. In a registration method where two planes of BBs are present on the fluoroscopic tracking fixture as discussed above with respect to FIG. 20, BBs from the plane 21009b nearest the detector 3005 are used for dewarping by applying a dewarping algorithm. One such dewarping algorithm is a morphing algorithm where the pixels within the triangle formed by three detected BB shadows are stretched/shrunk in two dimensions so that the triangle matches the known shape. In the proposed new registration method, it is also possible to continue to use BBs on the detector 3005 for dewarping. Unlike in the old fixture, only one plane of BBs (instead of two planes) would be needed. This single plane would serve to support dewarping and also provide orientation landmarks to provide/ensure each new image matches the arbitrary screen orientation and offset that may differ from image to image. Also unlike in the old methods, it should be possible to collimate as much as desired/needed since dewarping only occurs within regions bounded by visible BBs. At least 3 orientation BBs would still need to be visible within the collimated region to provide/ensure correct image orientation. Since a BB plane is also used/required for the tracking fixture of FIG. 27B on the detector 3005 in the calibration process, the temporary tracker of FIG. 27B on image-intensifier-based detectors 3005 could double as the permanent tracker.

The fluoroscopic fixture of FIG. 20 using two planes of BBs 21009a and 21009b has some features used to account for user-controlled on-screen image rotation, image magnification, and image flip. It is important to account for these factors, which may vary from shot to shot depending on how the user adjusts settings and noise inherent in the system, to get an accurate mapping of the 3D coordinate system to the 2D images and vice versa. To account for magnification, some BBs could be arranged in a ring with known diameter, and spacings between dewarping BBs could be known. To account for on-screen image rotation, the BBs in the existing image-intensifier fixture are laid out in an asymmetrical pattern. The asymmetrical pattern is asymmetrical rotationally and also asymmetrical from front to back, so that a flipped and/or rotated image is immediately recognized as such.

Figure 29A:
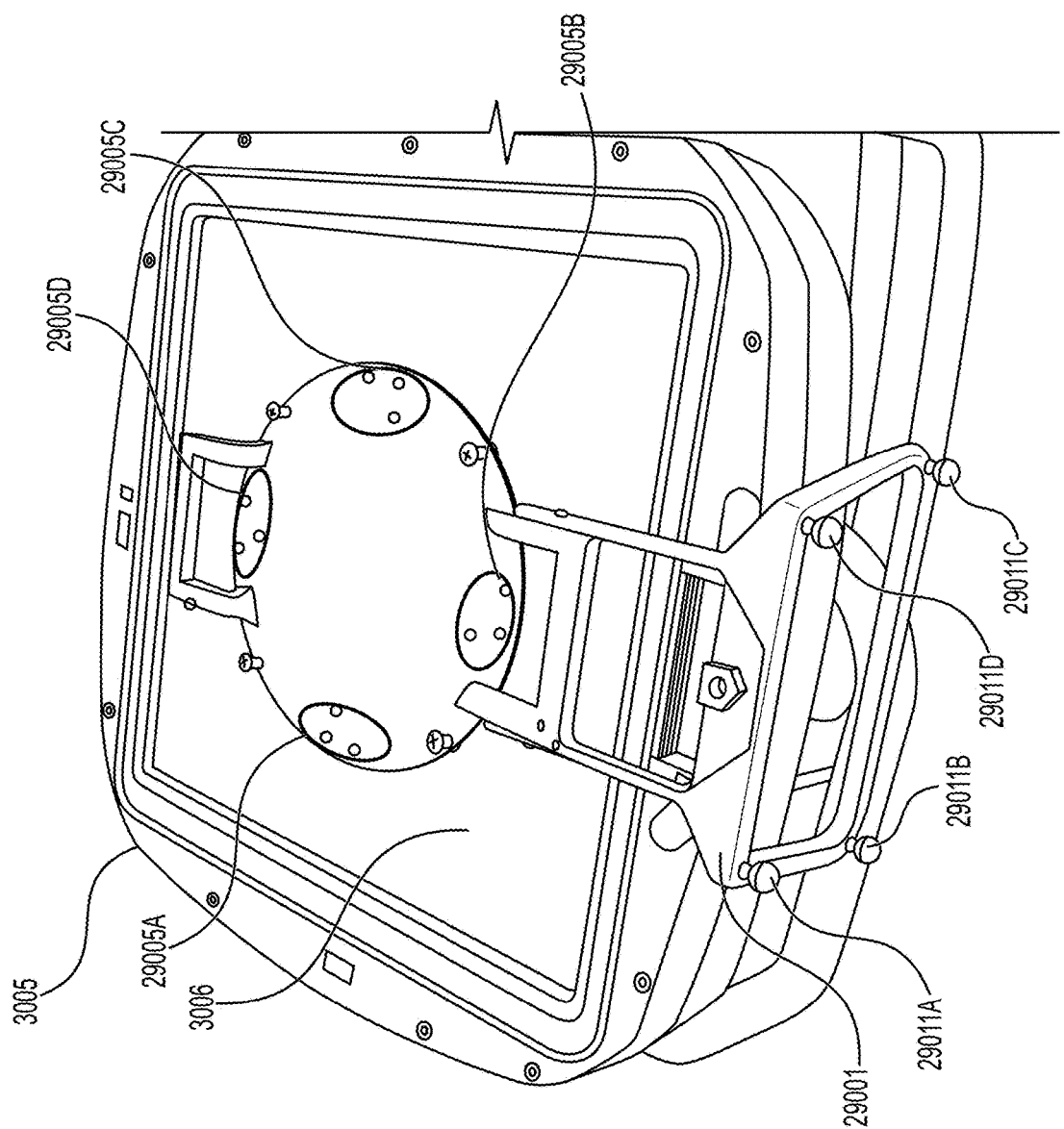
Figure 29C:
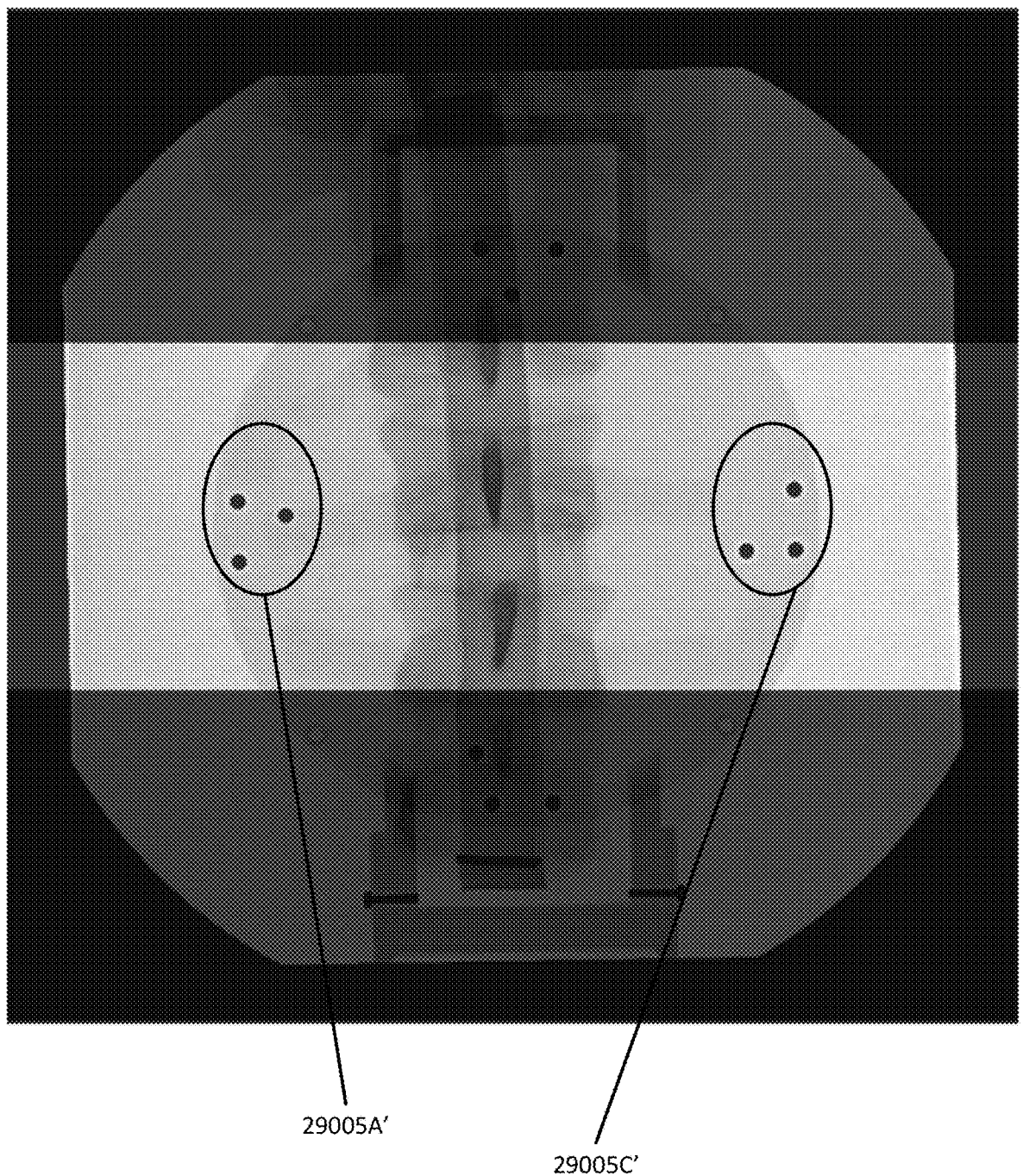

A new fluoroscopic fixture with a single plane need not utilize any BBs for dewarping when used with flat panel units, and just needs to account for image orientation, flip, and magnification. The existing pattern on the old fixture's far plane 21009a uses 6 orientation BBs distributed in different rotational positions at a constant radius from fixture center (not shown). Such an arrangement would fulfill the requirements of accounting for orientation, flip, and magnification, but may be somewhat limited for collimated shots. Another possible BB layout could utilize BBs clustered in groups of 3 to allow for collimation from top-bottom or left-right as shown in FIGS. 29A, 29B, and 29C. As shown in FIG. 29A, fixture 29001 may be provided on the face 3006 of detector 3005 between detector 3005 and source 3001. Fixture 29001 may include 4 groups of BBs (also referred to as fiducials) 29005A, 29005B, 29005C, and 29005D, with each group including three BBs, and with each group of 3 BBs provided in a different pattern. In FIG. 29A, fixture 29001 includes an optical tracking array with optical tracking markers 29011A, 29011B, 29011C, and 29011D provided in a relationship that is fixed relative to BBs of groups 29005A, 29005B, 29005C, and 29005D.

Fixture 29001 may thus be used like Fixture 8010 of FIG. 27B for calibration, but because Fixture 29001 is intended to be maintained on detector 3005 during procedures, the tracking array (including tracking markers 29011A, 29011B, 29011C, and 29011D) is extended to a side of detector 3005 and away from source 3001 as shown in FIG. 29A.

Examples of images taken using fixture 29001 of FIG. 29A with collimation are provided in FIGS. 29B and 29C. In FIG. 29B, shadows 29005B' and 29005D' of BB groups 29005B and 29005D are present in the image, and the patterns of these BB groups can be used to determine the orientation of this image. In FIG. 29C, shadows 29005A' and 29005C' of BB groups 29005A and 29005C are present in the image, and the patterns of these BB groups can be used to determine the orientation of this image.

Figure 30:
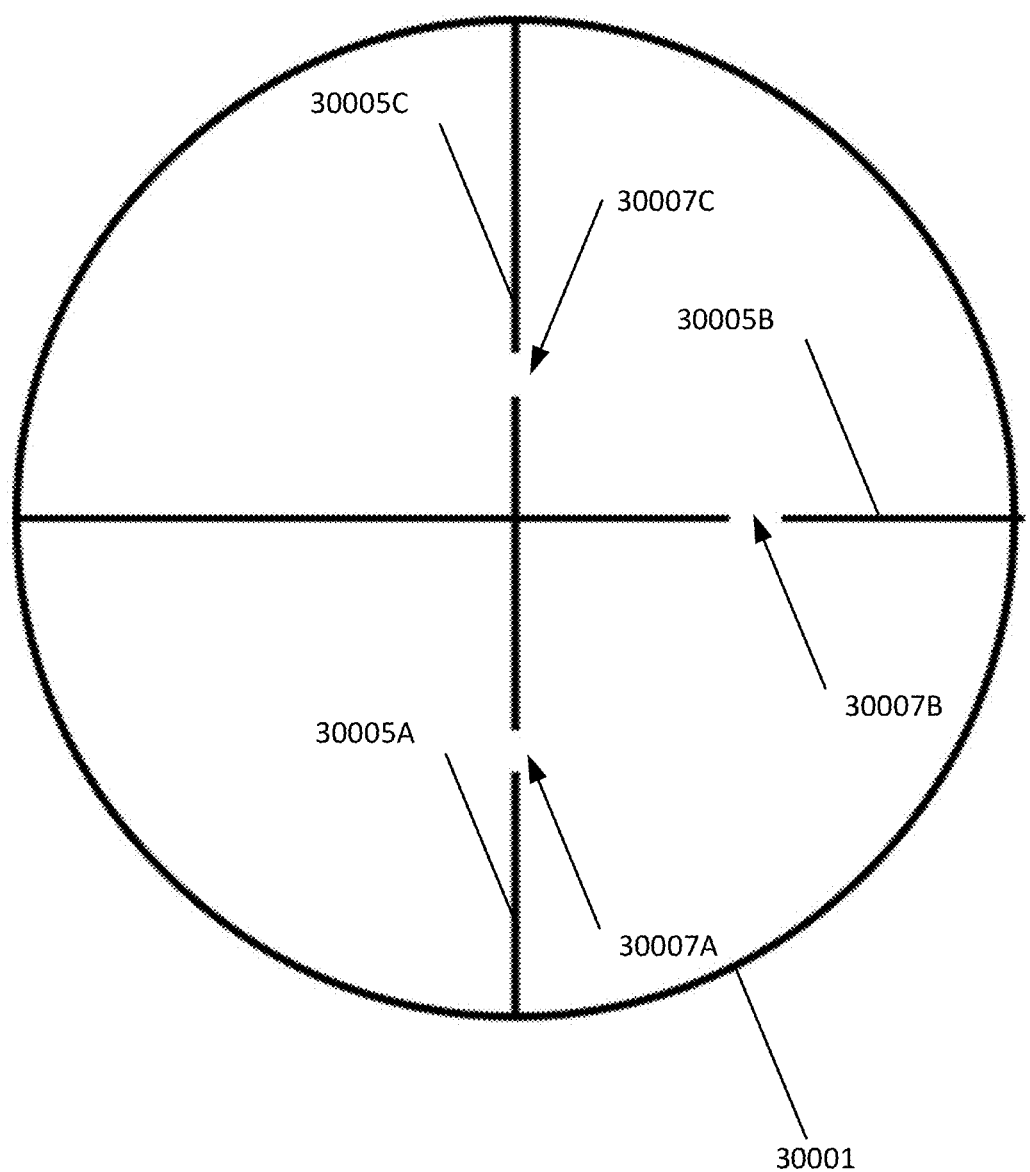
FIG. 30 illustrates use of a crosshair as a fiducial according to some embodiments of inventive concepts.

Another possible minimal fiducial layout could be a crosshair across the center of the screen with additional crosshairs or spaces and an asymmetrical feature as shown in FIG. 30. Other possible features with useful/necessary properties of asymmetry and spacing could be provided to detect these factors. In addition to being useful for detecting image rotation, magnification, and/or flip, these fiducials could be re-projected by software onto the image and should overlay perfectly if calibration is correct, giving the user confidence in valid registration. Such a software feature is similar to how the BBs from the two planes in the old fluoroscopic fixture are re-projected onto the images for a check of good registration.

FIG. 29A illustrates a configuration of BBs on a fixture 29001 with clusters of 3 BBs in top (29005D), bottom (29005B), left (29005A), and right (29005C) regions. Positioning BBs in this way allows 6 BBs to still be easily detected even in highly collimated shots with FIG. 29B being an x-ray fluoroscopic shot image with left-right collimation and with FIG. 29C being an x-ray fluoroscopic shot image with top-bottom collimation.

FIG. 30 illustrates an example of a fiducial configuration of a feature added to the detector fixture 29001 of FIG. 29A that could appear on fluoroscopic x-ray shots to serve as a reference for the image rotation, translation, magnification, and/or flip. The ring 30001 has a known diameter, and the length of each line segment 30005A, 30005B, and 30005C before the respective gap 30007A, 30007b, and 30007C is also known. The gaps are asymmetrically placed so that it is known rotationally and with regard to flip where the gaps should be on the image. The crosshairs can also be projected onto the image by software, providing feedback to the user on where the calibration believes is the center of the image plane.

Because each new image captured after calibrating the system is related back to a reference image by transforming (e.g., rotating, scaling, translating, and/or flipping), it is important that the fixture should be attached to the x-ray detector 3005 (image plane) securely. If the fixture were to slip, the source location relative to the image would no longer be accurate, even if adjusted for gravity. One approach would be to collect a new, calibrated reference air shot at the beginning of the procedure/case, along with gravity vector information in upright and lateral positions. The reference air shot would not have any anatomy present and would have a second BB plane present to allow accurate calculation of the source 3001 location using the pinhole camera model. The second plane could be a tracked BB plane such as plane 8055 of the source fixture of FIG. 27C or a rigidly attached temporary plane that is offset from the primary plane by a known amount. An alternate approach would be to design the detector fixture in such a way that it is known that it will always stay well attached or if it is detached, it can be reattached to exactly the same position.

Figure 31:
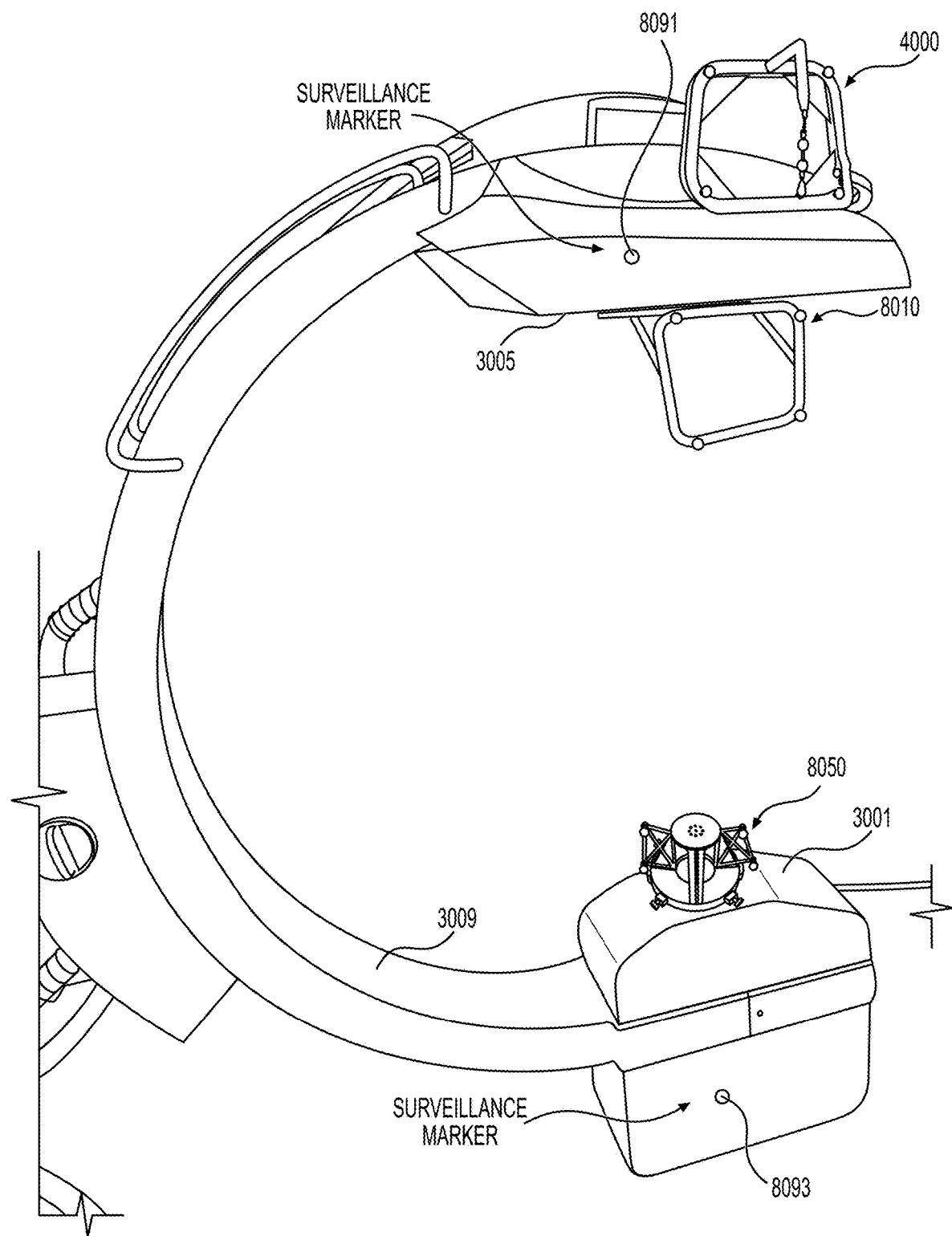
FIG. 31 illustrates use of surveillance markers on a fluoroscopic x-ray imaging system according to some embodiments of inventive concepts.

Because accuracy relies on the detector fixture 29001 being secure and/or accurately re-attachable to the detector 3005 in a reproducible exact way, it may be desirable to provide a way to know if the calibration is still valid after some time. According to some embodiments, a method to assess validity of the calibration is to attach one or more surveillance markers 8091 and 8093. In some embodiments, one surveillance marker 8091 is attached on/near the detector 3005 and one surveillance marker 8093 is attached on/near the source 3001 as shown in FIG. 31. These surveillance markers, for example, may be reflective spheres, reflective stickers, or active markers detectable by the tracking system in the same way as the permanent fixture is detectable/tracked. The locations of these markers would be optically tracked relative to the permanent fixture at the time the calibration is performed. Later, when checking calibration, the surveillance marker 8091 near the detector 3005 should be in the same fixed position relative to the permanent tracking fixture 4000 and/or 8010 as it was during calibration. If the permanent tracking fixture or its tracking array become dislodged or bent, the surveillance marker can be used to detect offset from its predicted position and it will be apparent that there is a problem. Additionally, since the surveillance marker 8093 near the source 3001 should move in the same way as the source 3001 moves with changing C-arm and/or detector 3005 orientation, the system should be able to calculate and predict where the surveillance marker near the source 3001 would move at any C-arm and/or detector 3005 orientation. When checking calibration, the C-arm 3009 could be placed into a few different orientations without shooting x-rays. If the tracked surveillance marker location is not in the predicted location (based on recalled surveillance marker upright position adjusted to calibrated offset) at all tested orientations of the C-arm 3009 and/or detector 3005, then the calibration is incorrect and needs to be re-run.

FIG. 31 is a photograph of a C-arm 3009 with fixtures 8050, 8010, and 4000 attached and surveillance markers 8091 and 8093 drawn in two locations, one on/near the source 3001 and one on/near the detector 3005. The surveillance markers would allow the calibration accuracy to be checked before starting a procedure/case.

Figure 32:
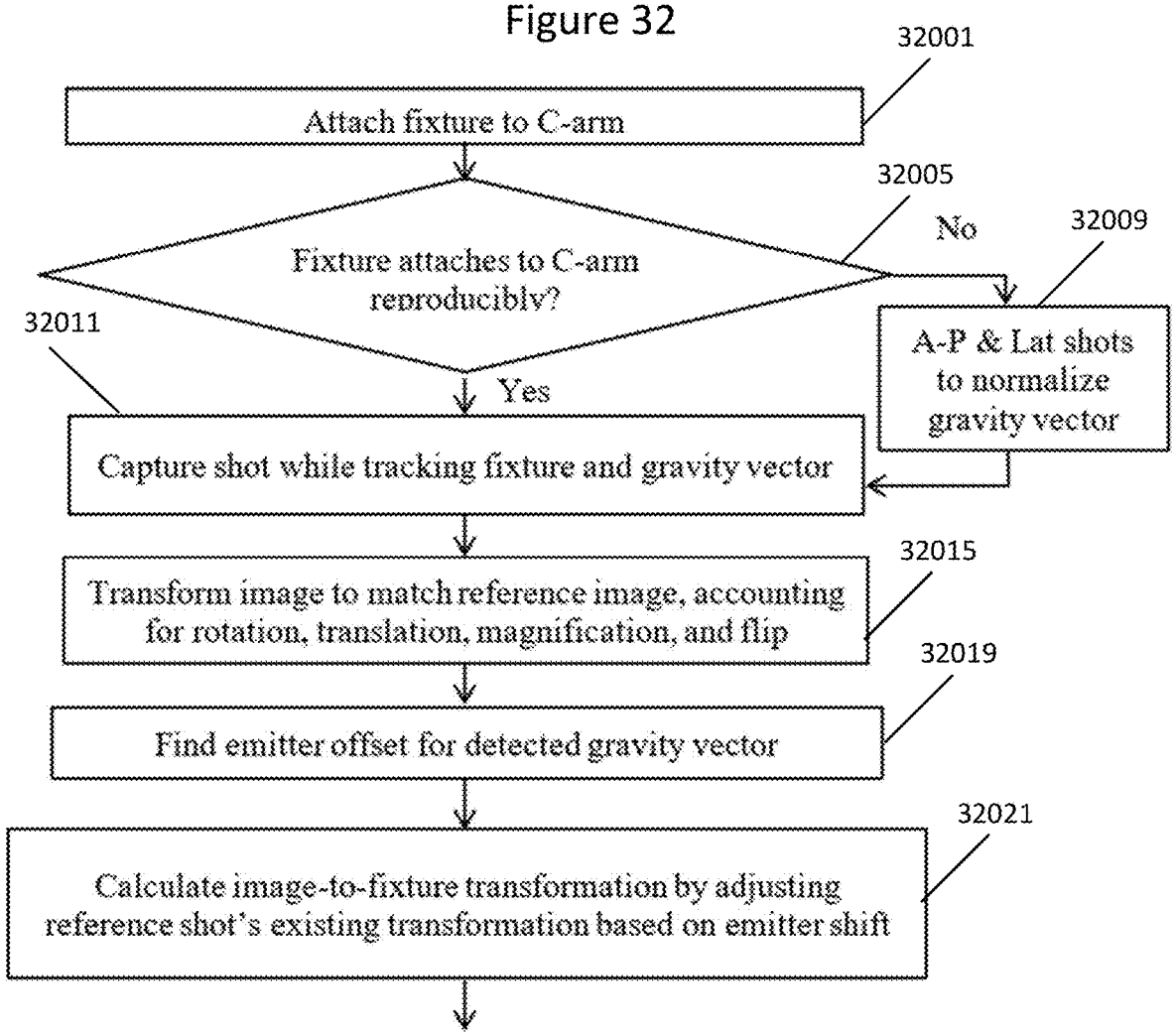
FIG. 32 is a flow chart illustrating use of a calibrated fixture according to some embodiments of inventive concepts.

The overall workflow when using this fixture after calibration is summarized in the flow chart of FIG. 32. Every new image that comes in is aligned with a reference image, and has a known shift in source 3001 relative to the reference image, so if the image-to-fixture transformation of the reference image is known or has been previously found using two planes, then a single plane fixture can be used according to this workflow.

FIG. 32 is a flowchart of an overall workflow when utilizing a calibrated fixture on the day of a procedure/case (e.g., a surgery) according to some embodiments of inventive concepts.

At block 32001, fixture 4000 is attached to C-arm 3009 as illustrated in FIG. 31.

At block 32005, an additional operation may be performed if an attachment/alignment of fixture 4000 on C-arm 3009 is not reproducible. If attachment/alignment of fixture 4000 on C-arm 3009 is not reproducible at block 32005, an anteroposterior A-P fluoroscopic image/shot (with detector 3005 aligned vertically over source 3001) is taken and a lateral fluoroscopic image/shot (with detector 3005 and source 3001 aligned horizontally) is taken at block 32009, and these fluoroscopic shots are used to normalize the gravity vector of fixture 4000. If attachment/alignment of fixture 4000 is reproducible at block 32009, the fluoroscopic shots of block 32009 may be omitted.

At block 32011, a fluoroscopic image is captured while tracking fixture 4000 and the gravity vector.

At block 32015, the image is transformed to match a reference image, accounting for rotation, translation, magnification, and/or flip.

At block 32019, a source 3001 offset is found for the detected gravity vector.

At block 32021, an image-to-fixture transformation is calculated by adjusting the existing transformation of the reference image based on the source 3001 offset/shift.

According to some embodiments, a feature may be provided to detect and indicate that x-rays are present. Such a feature is useful because the tracking information related to a shot must be synchronized with the image data in order for a registration to be accurate. Currently, the system detects when the image coming through the video capture board changes, at which time, the tracking data is polled. However, it is possible for false negatives or false positives to occur with new image detection, or for movement of the C-arm 3009 during shot capture to cause inaccuracy.

Figure 35:
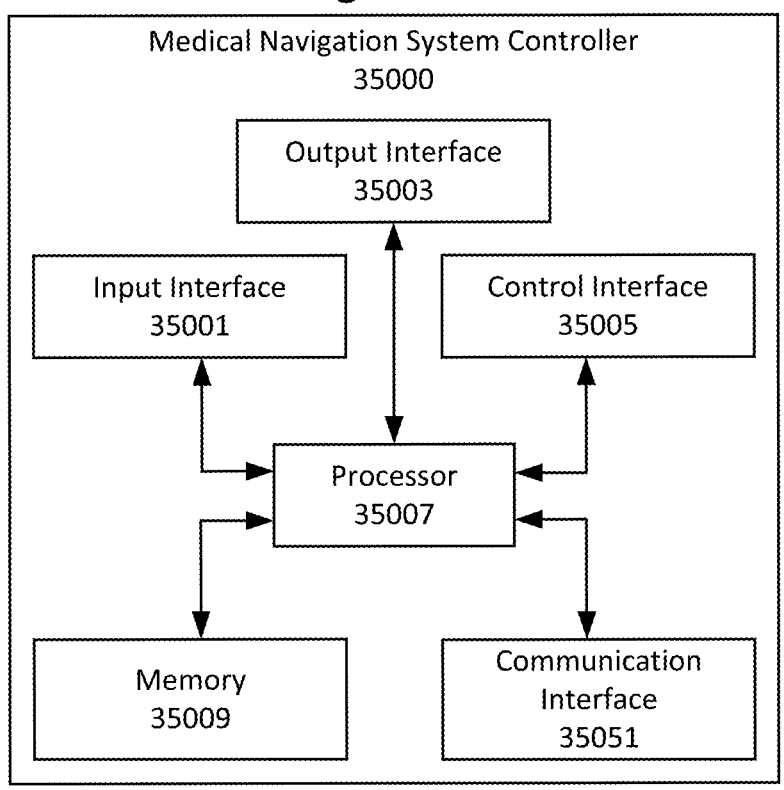
FIG. 35 is a block diagram illustrating a robotic controller according to some embodiments of inventive concepts

According to some embodiments, one mechanism to synchronize imaging and tracking data is to transmit through wireless (e.g., WiFi, Bluetooth, etc.) or wired methods the state of an electronic x-ray detector to the robot system (e.g., to the robot controller 35000 of FIG. 35). This synchronizing signal could be read through a DIO (digital input-output) port and used by software to ensure that tracking data are only collected when x-rays are active.

According to some other embodiments, another mechanism to synchronize imaging and tracking data is to use information from an electronic x-ray presence sensor 33019 as a signal that causes one or more tracking markers (e.g., tracking markers of active marker array 33001) to strobe only when x-rays are present/detected. If all the markers of the array strobe only when x-rays are detected, the system would only be able to track the fixture during x-ray fluoroscopic shots. Or, if only one marker on the array or adjacent to the array is switched on responsive to detecting x-rays, the system could still determine if the fixture is within view of the cameras even though an x-ray shot is not being collected. Such an active marker array 33001 is illustrated in FIG. 33.

According to some other embodiments, a passive reflective marker on a pivot or piston (also referred to as a movable marker) could be actuated to indicated when an x-ray fluoroscopic shot is being taken. A motor or other driver would be switched on and would force the pivot or piston to one position when x-rays are present/detected. When x-rays are not present/detected, the motor would switch off and the pivot or piston would return the passive marker under a spring-loaded mechanism to its resting position. The tracking cameras would detect the marker's position and only record the fixture location when x-rays are active. Such a movable marker array could be used instead of the active marker array of 33001 of FIG. 33.

Figure 33:
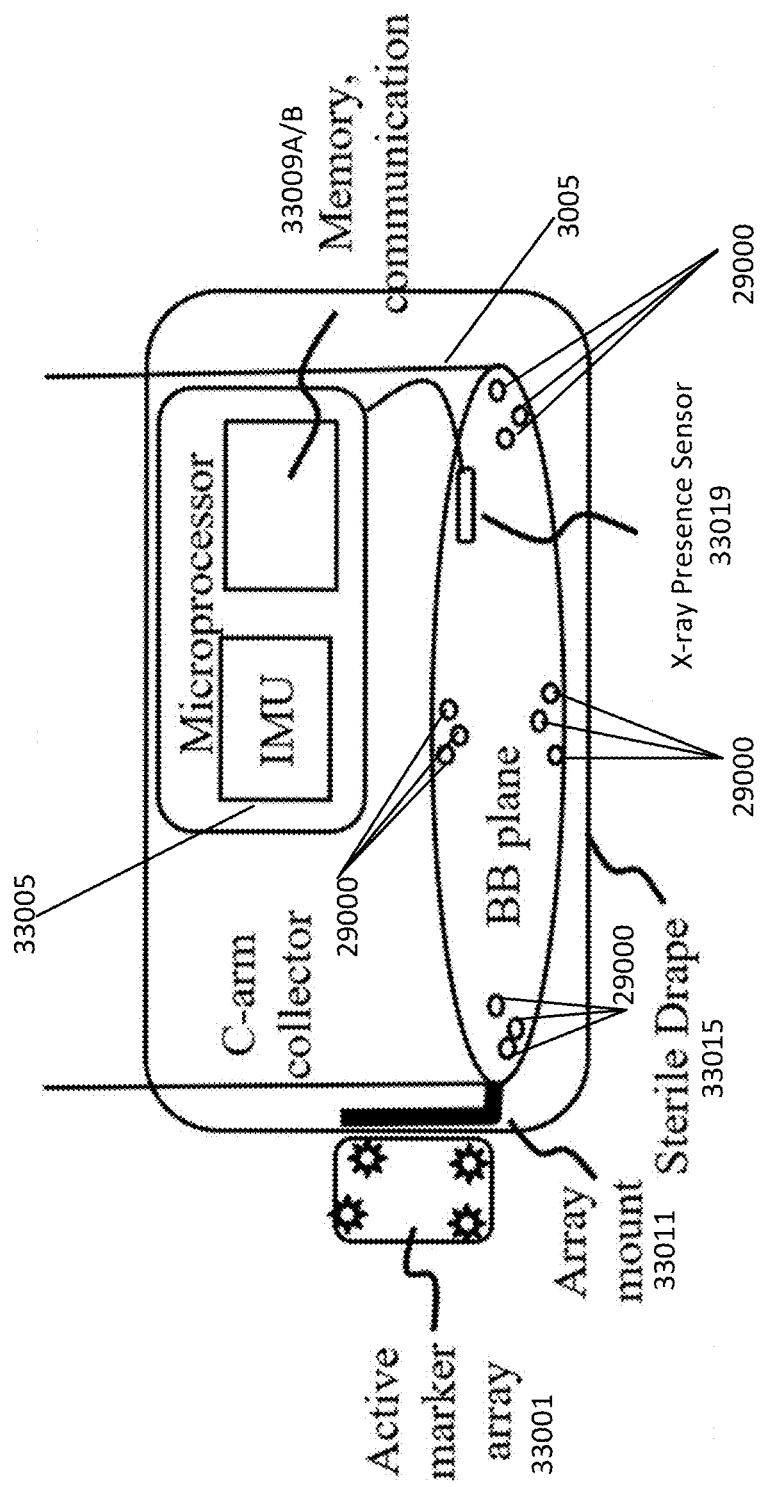
FIG. 33 is a schematic diagram illustrating a fixture for use on an x-ray detector according to some embodiments of inventive concepts.

According to some embodiments, an electronic version of the detector fixture is illustrated in FIG. 33. This detector fixture may use an array of active markers 33001 that emit infrared light and can be tracked more accurately than passive reflective spheres. Additionally, the detector fixture may use an IMU 33005 instead of an optically tracked gravity vector to accurately detect the orientation of the C-arm 3009 and/or detector 3005 relative to gravity. The fixture may include on-board memory 33009A, possibly loadable through a USB flash drive or other portable memory storage device, or loadable through wireless communication, to hold the parameters of a lookup table or function that relates IMU output to an offset (also referred to as a shift) of source 3001 relative to detector 3005. An identification ID of the fluoroscopic C-arm system being used could be received/retrieved automatically using a near field communication NFC tag, a Quick Response QR code and reader, a bar code, a Radio Frequency Identifier RFID tag, or other type of proximity device mounted on the C-arm detector 3005 near where the fixture attaches to provide/ensure that the correct parameters are loaded for the C-arm fluoroscopic system to which the detector fixture is attached and to allow the same detector fixture to be used on different fluoroscopic C-arm systems. The detector fixture could be wireless and battery powered, or wired for A/C power. In either case, the active markers of array 33001 could be electronically linked to the rest of the fixture and/or powered using inductive coupling or other methods, thereby allowing the markers to be provided sterile, and attached to array mount 33011 of the fixture over/through the outside of a sterile drape 33015 around the fixture and detector similar to how the end effector of the robot currently attaches to the robot arm over the drape. This fixture may additionally have an x-ray presence sensor 33019 to synchronize tracking data with fluoroscopic x-ray shots.

The detector fixture of FIG. 33 may also include a BB plane as discussed above for example with respect to the fixture of FIG. 29A. In general, the fixture of FIG. 33 may be similar to the fixture of FIG. 29A with the addition/substitution of active components such as IMU 33005, x-ray presence sensor 33019, and active marker array 33001. Moreover, the fixture of FIG. 33 may include the array mount 33011 allowing the detachable coupling of active marker array 33001 through the sterile drape 33015.

1) The fixture of FIG. 33 may allow collimation without affecting accuracy of registration as discussed above with respect to FIGS. 29A, 29B, and 29C. As shown in FIG. 33, the fixture may include fiducials 29000 (also referred to as an x-ray opaque fiducial pattern, e.g., provided using metal BBs or another x-ray opaque material) as discussed above with respect to FIGS. 29A, 29B, and 29C. For example, each grouping (also referred to as a cluster) of 3 fiducials (e.g., provided using BBs) may be provided in a different pattern/orientation to allow identification of each grouping/cluster in a fluoroscopic x-ray image. Moreover, the x-ray opaque fiducial pattern may be provided in/on a layer of an x-ray transparent material, also referred to as a fiducial plane.

2) The fixture of FIG. 33 may be less obtrusive, allowing it to be positioned closer to the patient, because multiple planes of BBs are not required.

3) There may be fewer artifacts in the x-ray images produced with the fixture of FIG. 33 by reducing a number of BB shadows (also referred to as fiducial shadows).

4) Since image processing may be reduced according to some embodiments, x-rays where fiducials cannot be distinguished may pose less of a problem.

Figure 38A:
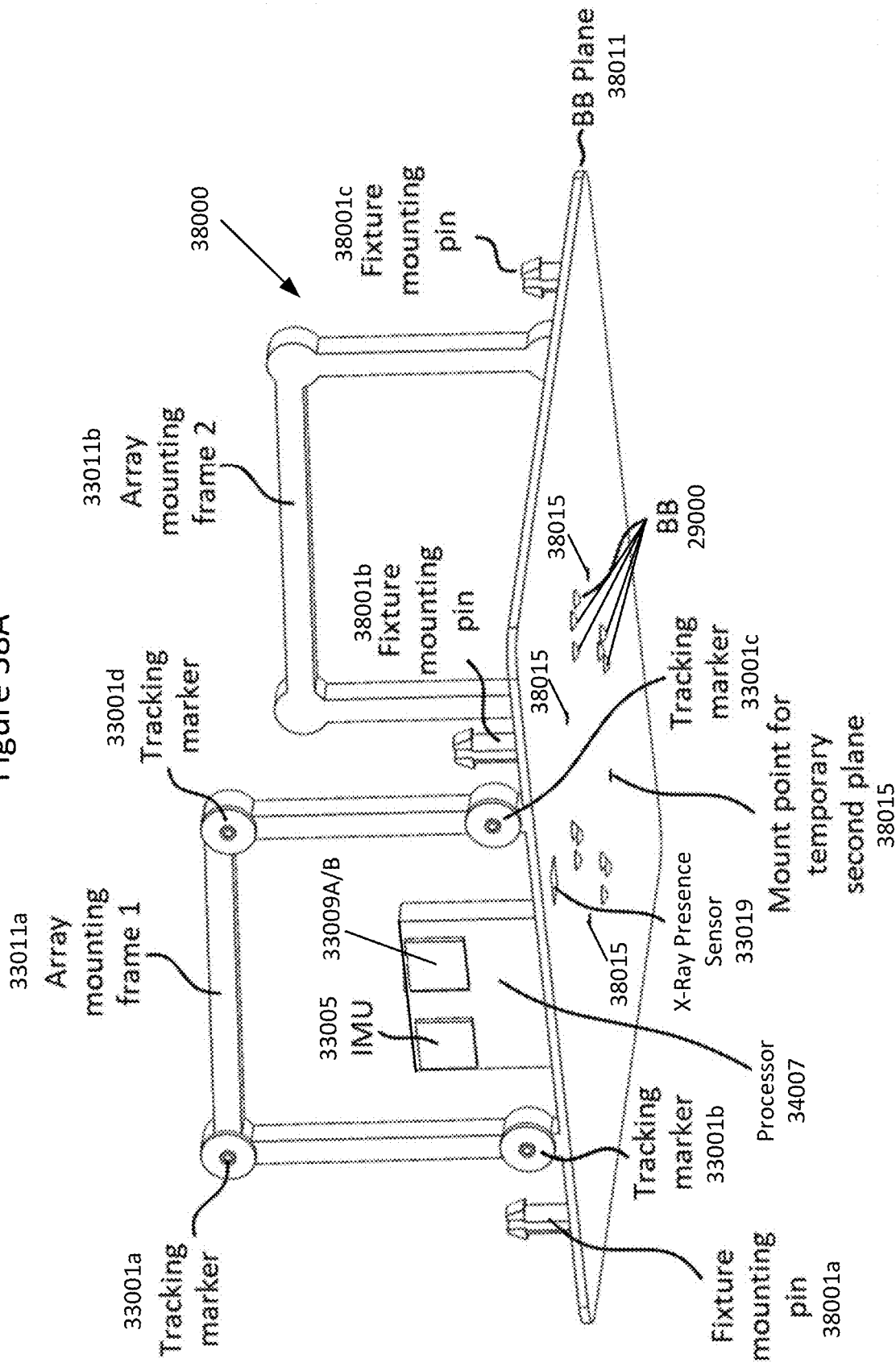
FIGS. 38A and 38B are plan views illustrating a fixture of FIG. 33 according to some embodiments of inventive concepts.
Figure 38B:
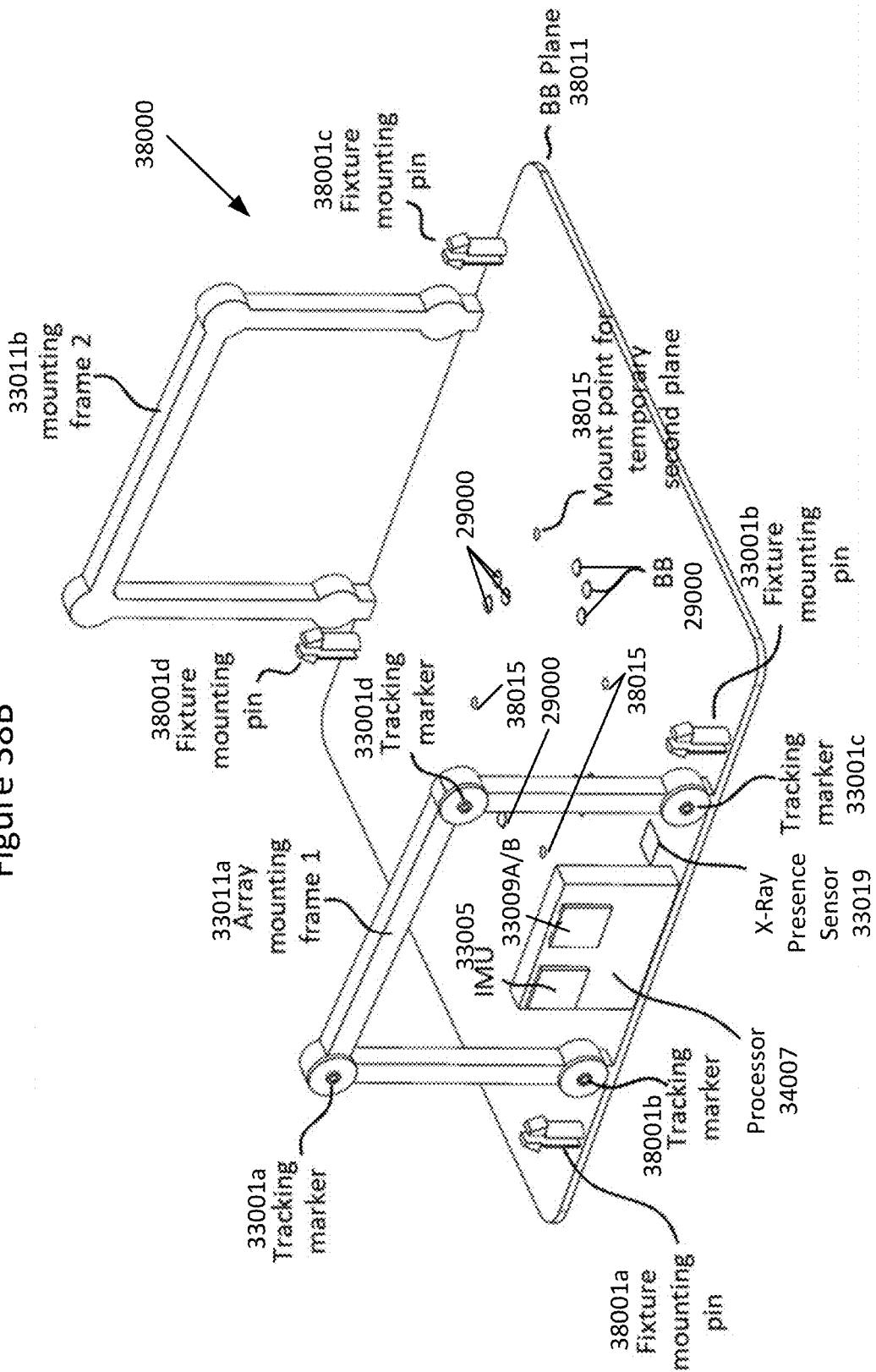

FIGS. 38A and 38B are plan views illustrating a fixture 38000 of FIG. 33 according to some embodiments of inventive concepts. In FIGS. 38A and 38B, an x-ray opaque fiducial pattern is provided in/on fiducial plane 38011 (also referred to as a BB plane) provided using a layer of an x-ray transparent material, such that all elements of the x-ray opaque fiducial pattern are in a single plane. As shown, the x-ray opaque fiducial pattern may be provided using clusters of BBs (i.e., spherical metal balls, also referred to as ball bearings). According to some other embodiments, the x-ray opaque fiducial pattern may be provided using a cross-hair pattern made up of fiducial segments as discussed above with respect to FIG. 30. According to still other embodiments, elements of the x-ray opaque fiducial pattern may be provided using circular shaped x-ray opaque discs (e.g., metal discs) with each circular shaped disc having flat upper and lower surfaces, or using a printed/painted pattern of circles (using an x-ray opaque material/paint). For example, the x-ray opaque fiducial pattern may be painted/printed on an upper/lower surface of the fiducial plane 38011.

In FIGS. 38A and 38B, the array mount of FIG. 33 may be provided using array mounting frame 33011a, and the active marker array 33001 of FIG. 33 may be provided using tracking markers 33001a, 33001b, 33001c, and 33001d supported on array mounting frame 33011a. Tracking markers 33001a, 33001b, 33001c, and 33001d may be detachable coupled with array mounting frame 33011a, for example, using detachable mechanical and/or magnetic couplings, to allow attachment over/through a sterile drape as shown in FIGS. 45A, 45B, and 45C. In addition, a second array mounting frame 33011b (and respective tracking markers) may be provided for a second active marker array on an opposite side of the fixture. With two active marker arrays, tracking sensors (e.g., cameras) may track the x-ray detector from either side or both sides of the x-ray detector.

Fixture mounting pins 38001a, 38001b, 38001c, and 38001d provide a detachable mounting with the x-ray detector as shown in FIGS. 40, 41, 43, 44, and 45A. In some embodiments of FIGS. 38A and 38B, each mounting pin may include a pair of snap-fit projections, where each snap-fit projections includes a flexible stem and an outward facing head with an entrance surface at an acute angle with respect to the stem and a retention surface that is orthogonal with respect to the stem. The two snap-fit projections of a mounting pin can thus be inserted into a respective mounting socket. The entrance surfaces of the two heads facilitate entry of the mounting pin into the mounting socket and inward flexing of the respective stems. Once the mounting pin is fully inserted into the mounting socket with the two heads clear of the mounting socket opening, the two snap-fit projections spring out so that the retention surfaces of the two snap-fit projections engage an outside surface of the mounting socket to securely attach the fixture to the x-ray detector. The mounting may be released by pinching the two heads of the mounting pin so that the retention surfaces of the respective heads disengage from the outer surface of the mounting socket allowing the mounting pin to be pulled/pushed free of the mounting socket. Accordingly, each of mounting pins 38001a, 38001b, 38001c, and 38001d may be configured to detachably mate with a respective mounting socket.

Figure 44:
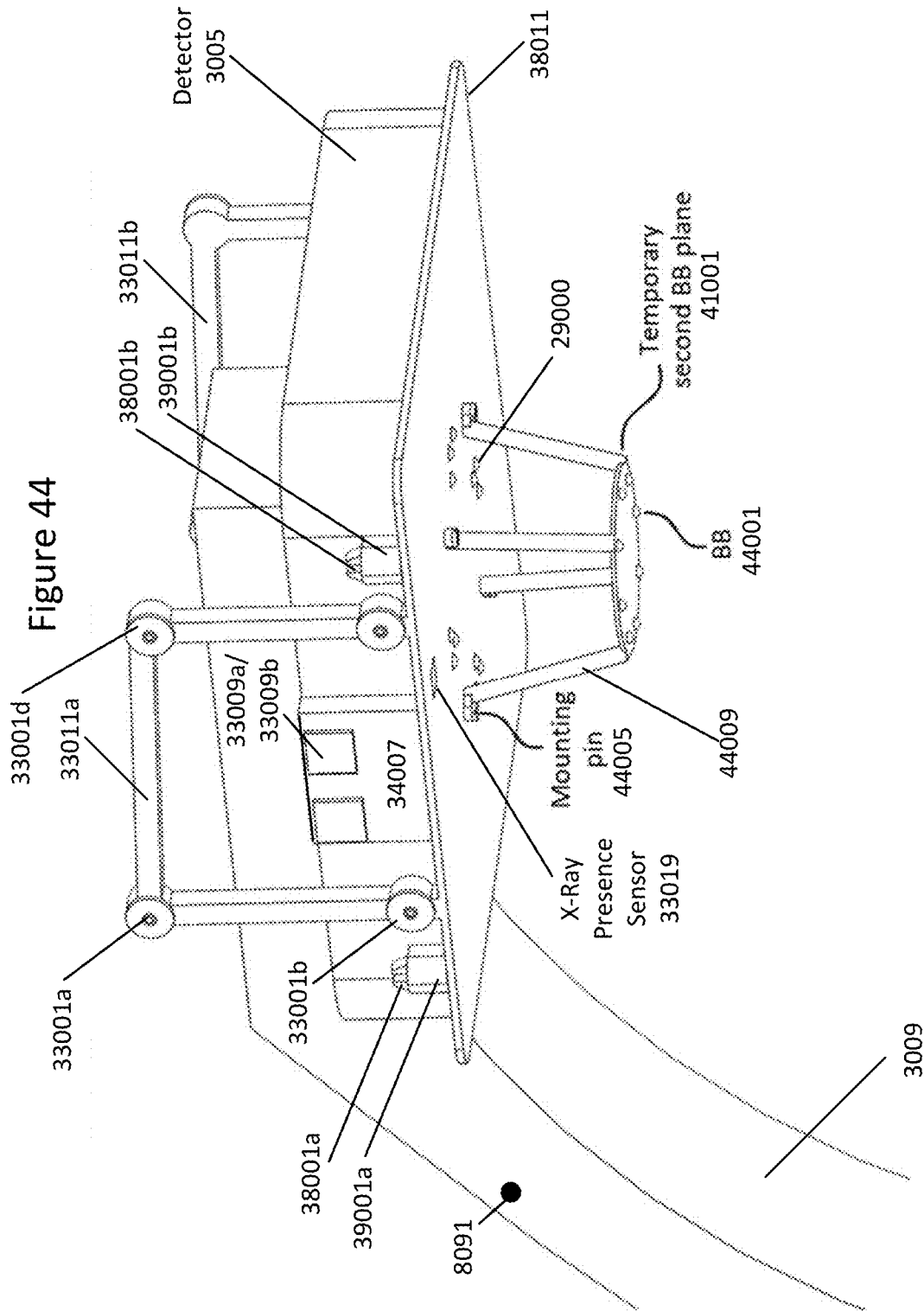
FIG. 44 is an expanded plan view of a fixture and a temporary x-ray opaque fiducial pattern mounted on an x-ray detector of a fluoroscopic x-ray imaging system according to some embodiments of inventive concepts.

In addition, the fixture may include mounting points 38015 to provide temporary mounting for a second x-ray opaque fiducial pattern in a second plane as discussed with respect to FIGS. 41 and 44.

Figure 42:
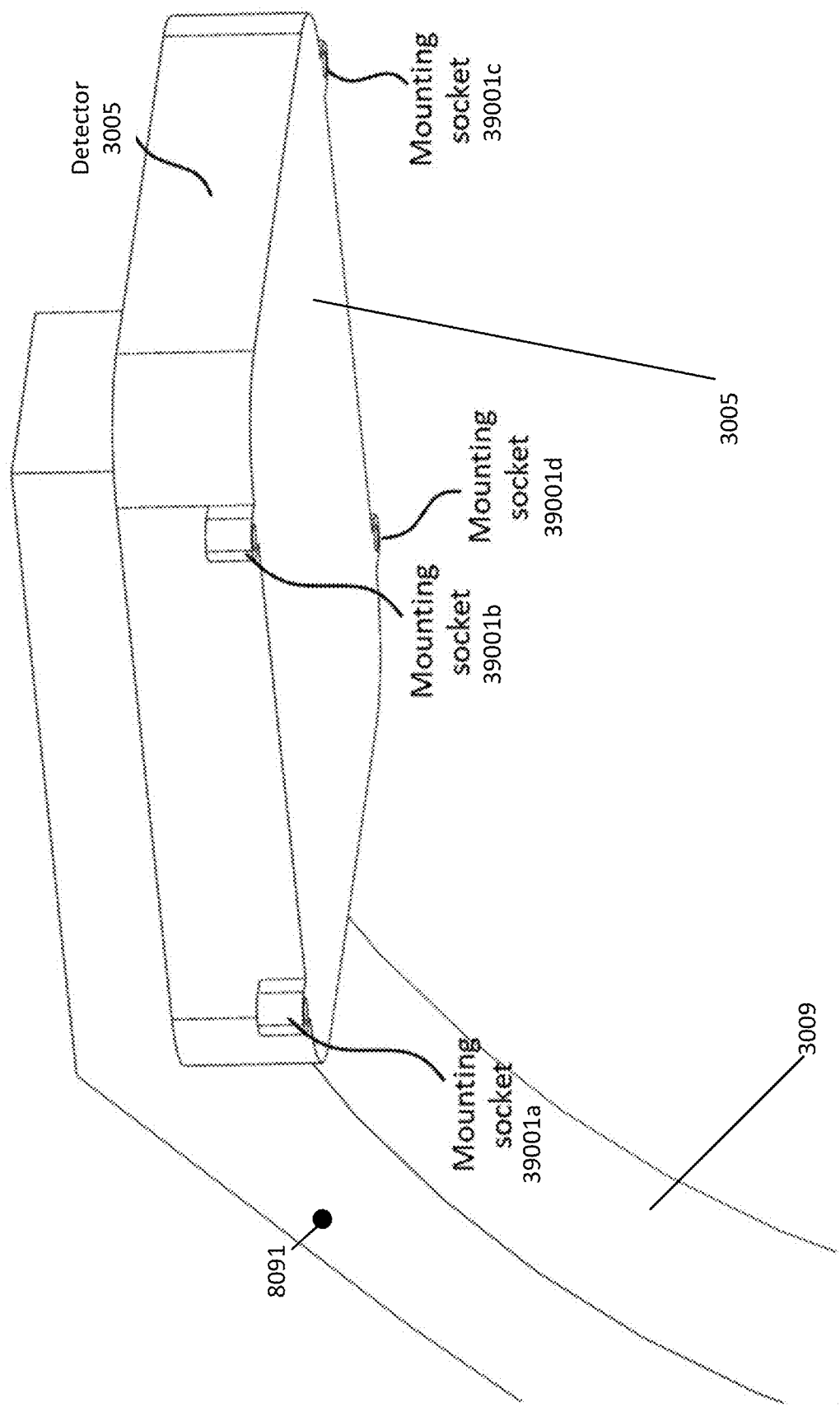
FIG. 42 is an expanded plan view of an x-ray detector of a fluoroscopic x-ray imaging system including mounting sockets according to some embodiments of inventive concepts.
Figure 43:
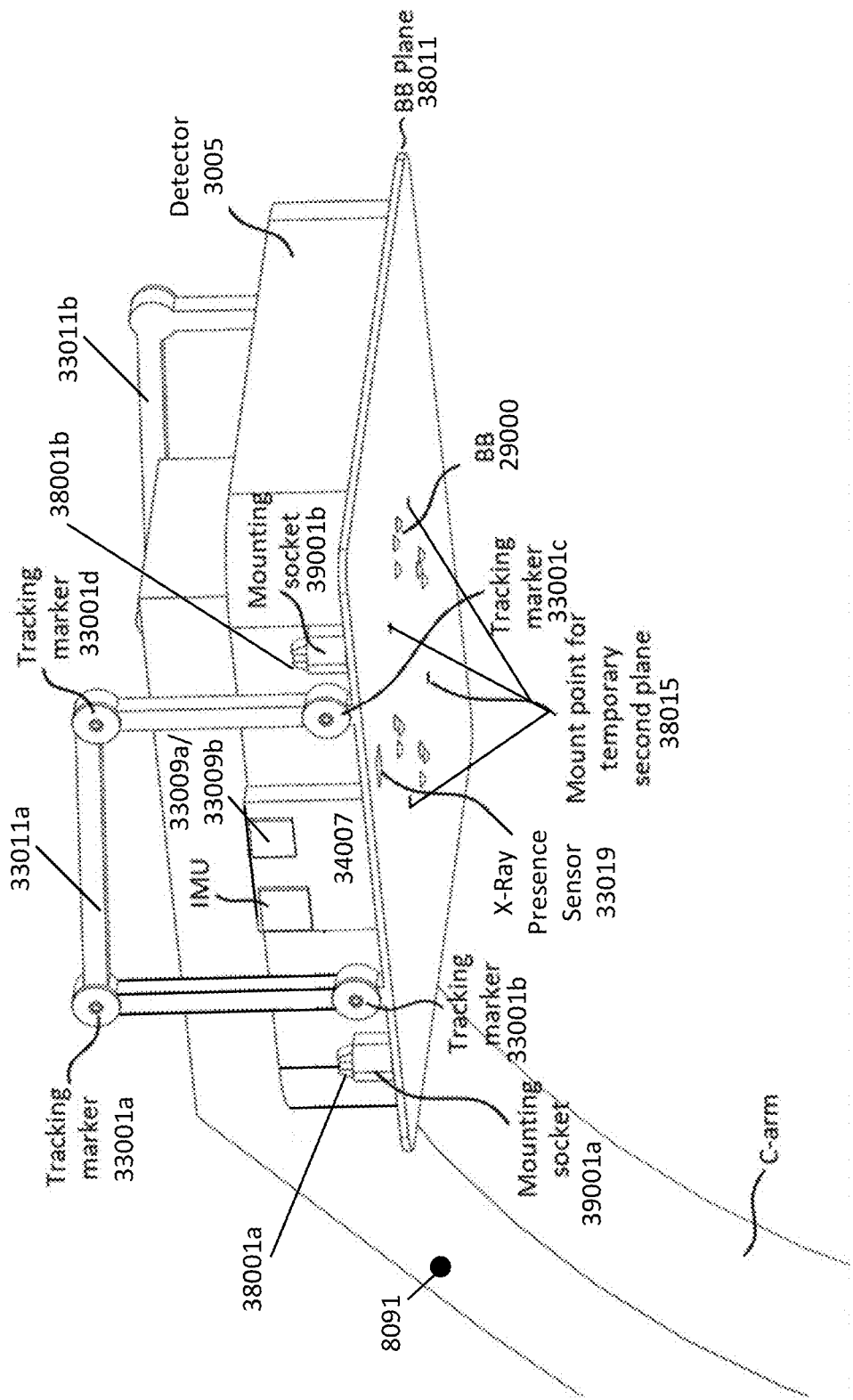
FIG. 43 is a an expanded plan view of a fixture mounted on an x-ray detector of a fluoroscopic x-ray imaging system according to some embodiments of inventive concepts.

FIGS. 39 and 42 illustrating mounting sockets 39001a, 39001b, 39001c, and 39001d on x-ray detector 3005. Each of the mounting sockets is configured to receive a respective mounting pin as discussed above with respect to FIGS. 38A and 38B. The fixture of FIGS. 38A and 38B can thus be detachably mounted on x-ray detector 3005 as shown in FIGS. 40, 41, 43, 44, and 45A. In FIG. 43, for example, each mounting pin may be released from the respective socket by pinching the head and pushing it into the respective mounting socket.

As shown in FIGS. 41 and 44, a second x-ray opaque fiducial pattern 44001 (e.g., a pattern of BBs) may be provided in a second fiducial pattern plane 41001 that is temporarily mounted on the fixture using legs 44009 and mounting pins 44005 that detachably mate with mounting points 38015 (discussed above with respect to FIGS. 38A and 38B), and the second x-ray opaque fiducial pattern 44001 may be used to generate the correlation of offsets of x-ray source 3001 relative to x-ray detector 3005 as a function of an orientation of x-ray detector 3005 relative to gravity. For example, the fluoroscopic x-ray imaging system may take an air-shot image (i.e., an image without a patient present) at an orientation of the C-arm 3009 (e.g., a reference orientation of the C-arm, for example, with the x-ray detector 3005 positioned vertically above the x-ray source 3001) with both the fixture including the first fiducial pattern and the second fiducial pattern. The air-shot image thus includes shadows corresponding to the two fiducial patterns in the different planes, and this air-shot image can be provided to the medical navigation system. For the air-shot image, the fixture can also provide information regarding an orientation of x-ray detector 3005 relative to gravity based on information from IMU 33005, or the medical navigation system can determine an orientation of x-ray detector 3005 relative to gravity based on an orientation of a gravity vector using information received via tracking sensors (e.g., camera system) as discussed above with respect to FIGS. 23A, 23B, 23C, 24A, 24B, 27A, and 31. Accordingly, the medical navigation system can generate the correlation of offsets based on the air-shot image including the shadows of the two fiducial patterns and using the information regarding the orientation of x-ray detector 3005 relative to gravity for the air-shot image. According to some other embodiments, the second x-ray opaque fiducial pattern may be temporarily provided on x-ray source 3001 as discussed above with respect to FIG. 27C. According to some other embodiments, an optical tracking array may be coupled with x-ray source 3001 as discussed above with respect to FIG. 27C, and the medical navigation system may determine a location/orientation of x-ray source 3001 using information received via tracking sensors for the air-shot image, and the locations/orientations of x-ray source 3001 may be used in addition to information discussed above to determine the correlation of offsets.

According to some embodiments of inventive concepts, the medical navigation system is configured to generate the correlation of offsets based on the air-shot image from the fluoroscopic imaging system with the air-shot image corresponding to one orientation of the C-arm (e.g., a reference orientation of the C-arm, for example, with the x-ray detector 3005 positioned vertically above the x-ray source 3001). For example, the air-shot image may be generated with the x-ray opaque fiducial pattern 29000 of the fixture 38000 and the x-ray opaque fiducial pattern 44001 that is temporarily coupled with the x-ray detector between the fixture and the x-ray source as shown in FIGS. 41 and 44 so that the air-shot image includes shadows corresponding to the x-ray opaque fiducial patterns 29000 and 44001. The medical navigation system may be configured to generate the correlation of offsets based on the air-shot image including the shadows corresponding to the x-ray opaque fiducial patterns 29000 and 44001, and/or based on positions of the x-ray source and/or x-ray detector corresponding to respective different orientations of the C-arm, with the positions of the x-ray source being determined based on an optical tracking array coupled with the x-ray source, and/or with positions of the x-ray detector determined based on optical tracking array 33001.

According to some other embodiments of inventive concepts, the medical navigation system is configured to generate the correlation of offsets based on an air-shot image from the fluoroscopic imaging system wherein the air-shot image corresponds to one orientation of the C-arm (e.g., a reference orientation of the C-arm, for example, with the x-ray detector 3005 positioned vertically above the x-ray source 3001). For example, the air-shot image may be generated with the x-ray opaque fiducial pattern 29000 of the fixture 38000 and with the x-ray opaque fiducial pattern 8055 that is temporarily coupled with the x-ray source between the fixture and the x-ray source as shown in FIGS. 27C and 31 so that the air-shot image includes shadows corresponding to the x-ray opaque fiducial patterns 29000 and 8055. The medical navigation system may be configured to generate the correlation of offsets based on the air-shot image including the shadows corresponding to the first x-ray opaque fiducial patterns 29000 and 8055, and/or based on positions of the x-ray source and/or x-ray detector corresponding to respective different orientations of the C-arm, with positions of the x-ray source being determined based on optical tracking array coupled with the x-ray source, and/or with positions of the x-ray detector determined based on optical tracking array 33001.

Once the correlation of offsets has been determined, the second x-ray opaque fiducial pattern (on the fixture or on x-ray source 3001) and/or the tracking array on the x-ray source 3001 may be removed before performing a medical procedure. The correlation of offsets may be stored in the medical navigation system and used for registration, or the correlation of offsets may be saved in memory at the fixture. If the correlation of offsets is saved at the fixture, the fixture can determine the orientation of x-ray detector 3005 relative to gravity (using output from IMU 33005) for each patient image during a procedure, determine the offset for the patient image based on the orientation relative to gravity and the correlation of offsets for each patient image, and transmit an indication of the offset to the navigation system for each patient image. If the correlation of offsets is saved at the navigation system, the fixture can determine the orientation of x-ray detector 3005 relative to gravity (using output from IMU 33005) for each patient image during a procedure and transmit the indication of the orientation relative to gravity to the medical navigation system for each patient image, and the medical navigation system can determine the offset for the patient image based on the orientation relative to gravity and the correlation of offsets for each patient image. Either way, the medical navigation system can perform registration based on the air-show images and based on the respective offsets.

As shown in FIGS. 45A, 45B, and 45C, once the fixture is mounted on x-ray detector 3005 and any temporary fiducial/tracking arrays have been removed, a sterile drape 33015 may be provided over the fixture and x-ray detector 3005. For example, because of electronic components included in the fixture, it may be difficult to sufficiently sterilize the fixture for surgery, and sterile drape 33015 may thus be required. Once sterile drape 33015 has been provided, sterile tracking markers 33001*a*, 33001*b*, 33001*c*, and 33001*d* may be coupled with mounting points 44002*a*, 44002*b*, 44002*c*, and 44002*d* of array mounting frame 33001*a*, either over or through the sterile drape. For example, the tracking markers may be magnetically mounted on respective mounting points without penetrating the sterile drape, or a snap fit pin of each tracking marker may penetrate the sterile drape to provide a snap fit mounting on a respective mounting point.

According to some embodiments, an optical surveillance marker 8091 may be provided on C-arm 3009 and/or on x-ray detector 3005 as discussed above with respect to FIG. 31. When the medical navigation system performs registration according to some embodiments, the optical surveillance marker 8091 can be used to validate the patient images.

Figure 34:
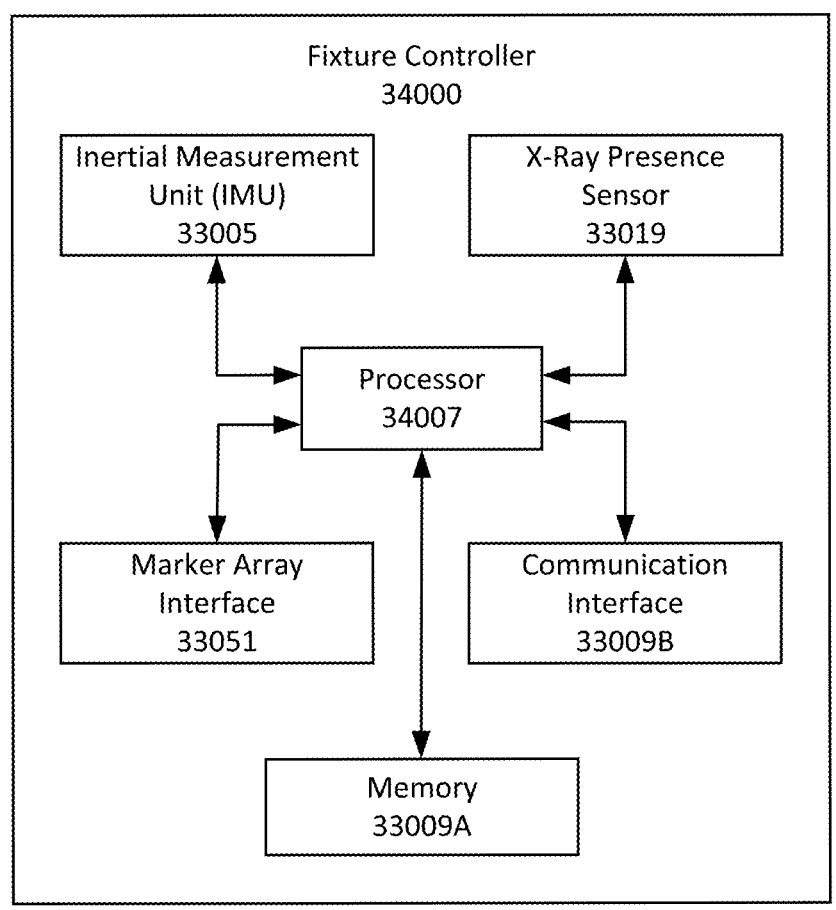
FIG. 34 is a block diagram illustrating a fixture controller according to some embodiments of inventive concepts.

FIG. 34 is a block diagram illustrating elements of a fixture controller 34000 for the detector fixture discussed above with respect to FIG. 33. As shown, the fixture controller 34000 may include processor circuitry 34007 (also referred to as a processor) coupled with inertial measurement unit (IMU) circuitry 33005 (also referred to as an inertial measurement unit or IMU), x-ray presence sensor circuitry 33019 (also referred to as an x-ray presence sensor/detector), marker array interface circuitry 33051 (also referred to as a marker array interface), memory circuitry 33009A (also referred to as memory), and communication interface circuitry 33009B (also referred to as a communication interface). The memory circuit 33009A may include computer readable program code that when executed by the processor circuit 34007 causes the processor circuit to perform operations according to embodiments disclosed herein. According to other embodiments, processor circuit 34007 may be defined to include memory so that a separate memory circuit is not required.

FIG. 35 is a block diagram illustrating elements of medical navigation system controller 35000 (e.g., implemented within computer 408 of the robotic system of FIG. 5). As shown, the medical navigation system controller 35000 may include processor circuitry 35007 (also referred to as a processor) coupled with input interface circuitry 35001 (also referred to as an input interface), output interface circuitry 35003 (also referred to as an output interface), control interface circuitry 35005 (also referred to as a control interface), memory circuitry 35009 (also referred to as a memory), and communication interface circuitry 35051 (also referred to as a communication interface. The memory circuitry 35009 may include computer readable program code that when executed by processor circuitry 35007 causes the processor circuitry to perform operations according to embodiments disclosed herein. According to other embodiments, processor circuitry 35007 may be defined to include memory so that separate memory circuitry is not required. Processor 35007 may use communication interface 35051 to receive information regarding an offset of an x-ray source of the fluoroscopic x-ray imaging system relative to an x-ray detector of the fluoroscopic x-ray imaging system. The communication interface 35051, for example, may receive such information from the fixture of FIGS. 34 and 35 using wired or wireless (e.g., WiFi, Bluetooth, etc.) communication.

As discussed herein, operations of controlling a medical navigation system according to some embodiments of the present disclosure may be performed by controller 35000 including processor 35007, input interface 35001, output interface 35003, control interface 35005, and/or communication interface 35051. For example, processor 35007 may receive user input through input interface 35001, and such user input may include user input received through foot pedal 544, tablet 546, a touch sensitive interface of display 110/304, etc. Processor 35007 may also receive position sensor input from tracking subsystem 532 and/or cameras 200 through input interface 35001. Processor 35007 may provide output through output interface 35003, and such output may include information to render graphic/visual information on display 110/304 and/or audio output to be provided through speaker 536. Processor 35007 may provide robotic control information through control interface 35005 to motion control subsystem 506, and the robotic control information may be used to control operation of a robotic actuator (such as robot arm 104/306-308/604, also referred to as a robotic arm), and/or end-effector 112/602. Processor 35007 may also use communication interface 35051 to receive information regarding an offset of an x-ray source of a fluoroscopic x-ray imaging system relative to an x-ray detector of the fluoroscopic x-ray imaging system. The communication interface 35051, for example, may receive such information from the fixture of FIGS. 33 and 34 using wired or wireless (e.g., WiFi, Bluetooth, etc.) communication.

Operations of a fixture for a fluoroscopic x-ray imaging system including a C-arm will now be discussed with reference to the flow charts of FIGS. 36A and 36B according to some embodiments of inventive concepts. For example, modules may be stored in memory 33009A of FIG. 34, and these modules may provide instructions so that when the instructions of a module are executed by processor 34007, processor 34007 performs respective operations of the flow chart of FIGS. 36A and/or 36B.

Figure 36A:
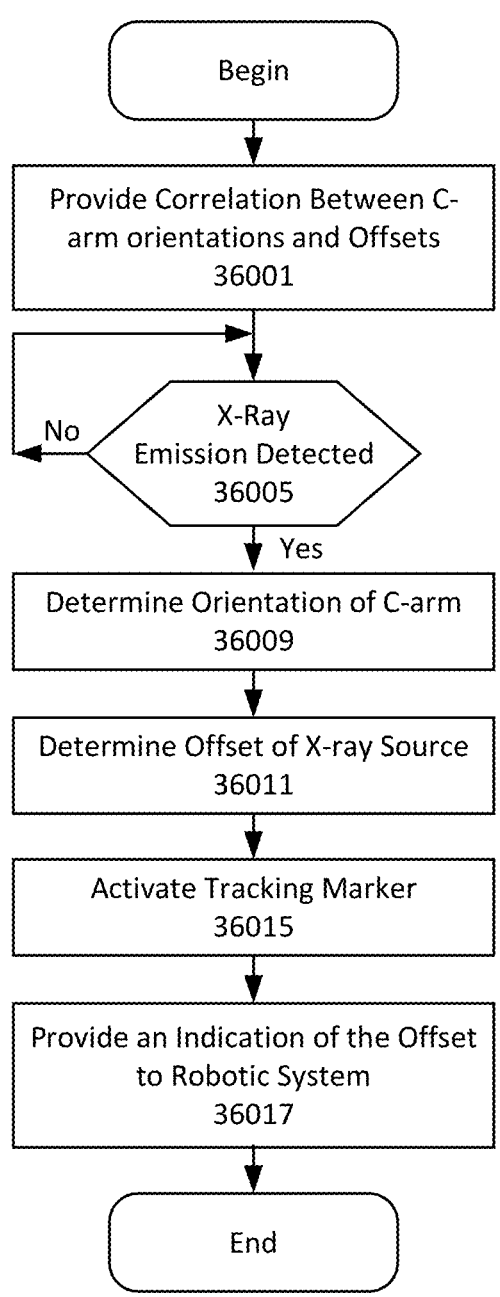
FIGS. 36A and 36B are flow charts illustrating operations of a fixture according to some embodiments of inventive concepts.
Figure 36B:
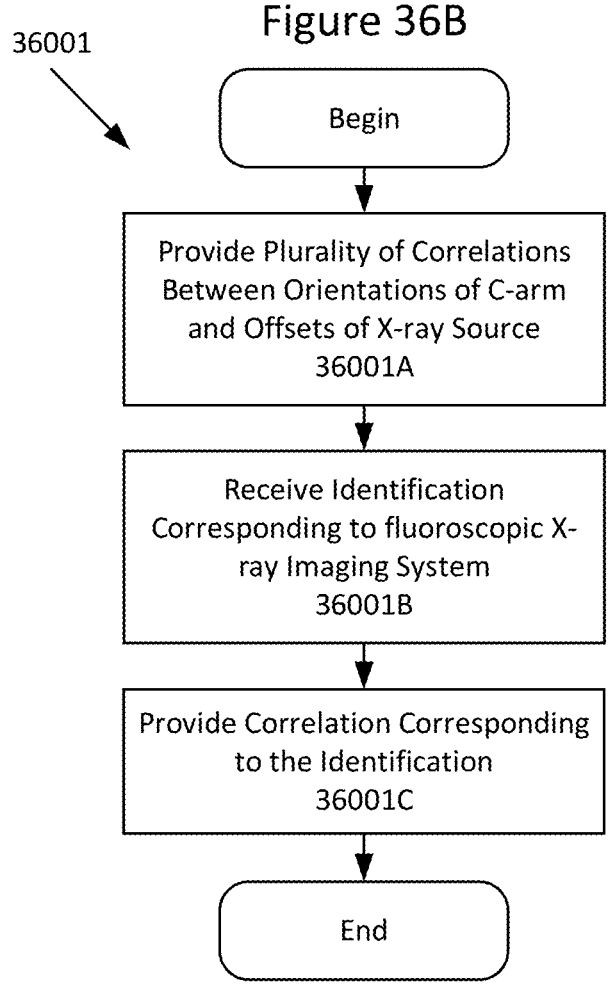

At block 36001 of FIG. 36A, a correlation between different orientations of the x-ray detector 3005 (and/or C-arm 3009) relative to gravity and respective offsets of the x-ray source 3001 relative to the x-ray detector 3005 may be provided in memory 33009A for the fluoroscopic x-ray imaging system. According to some embodiments, a single correlation may be provided in memory 33009A at block 36001 for a single fluoroscopic imaging system, and in such embodiments, the fixture may be used with a single fluoroscopic x-ray imaging system for which the correlation applies. The correlation may be provided, for example, based on one or more calibrations as discussed above.

According to some other embodiments discussed below with respect to FIG. 36B, a plurality of correlations may be provided in memory 33009A for respective different fluoroscopic x-ray imaging systems so that the same fixture may be used with different fluoroscopic x-ray imaging systems. According to such embodiments at block 36001A, a plurality of correlations between different orientations of C-arms 3009 and/or x-ray detectors 3005 and respective offsets of x-ray sources 3001 relative to x-ray detectors 3005 for different fluoroscopic x-ray imaging systems are provided in memory 33009A, and each of the plurality of correlations is associated with a different identification for the different fluoroscopic x-ray imaging systems. Accordingly, a different correlation may be provided in memory 33009A for each of the fluoroscopic imaging systems with which the fixture will be used, allowing one fixture to be used with different fluoroscopic x-ray imaging systems. At block 36001B, processor 34007 receives (e.g., through communication interface 33009B) an identification corresponding to the fluoroscopic imaging system with which the fixture will be used. For example, a smartphone (or other electronic device) may be used to read/capture an identification (e.g., a bar code, a QR code, an NFC tag, an RFID tag, etc.) on the fluoroscopic x-ray imaging system with which the fixture will be used, and the identification may be received by processor 34007 through communication interface 33009B via wireless communication from the smartphone or other electronic device, or processor 34007 may receive the identification directly through communication interface 33009B (e.g., by reading a Near Field Communication NFC tag or a Radio Frequency Identification RFID tag). At block 36001C, processor 34007 may provide the correlation of block 36001 by selecting the correlation corresponding to the identification received at block 36001B. The fixture may thus include an attachment mount configured to provide a detachable mechanical coupling with each of the different fluoroscopic x-ray imaging systems, and upon mounting the fixture on one of the fluoroscopic x-ray imaging systems using the attachment mount, the identification of that x-ray imaging system can be used to select the correlation for that fluoroscopic x-ray imaging system. Moreover, the fixture may include an x-ray opaque fiducial pattern in a single plane, and a mounting structure (e.g., mounting pins 38001a-d of FIGS. 38A and 38B) may be configured to provide the detachable mechanical coupling with x-ray detector 3005 so that the fiducial pattern is on a face of the x-ray detector between the x-ray detector 3001 and the x-ray source 3005 when the fixture is coupled to the x-ray detector using the mounting structure.

According to some embodiments, the correlation of block 36001 (or each correlation of block 36001A) may include a table in memory 33009A relating the different orientations of the x-ray detector 3005 (and/or C-arm 3009) relative to gravity and the respective offsets, a formula in memory 33009A relating the different orientations of the x-ray detector 3005 (and/or C-arm 3009) relative to gravity and the respective offsets, and/or a model in memory 33009A relating the different orientations of the x-ray detector 3005 (and/or C-arm 3009) relative to gravity and the respective offsets. If the fixture is provided with correlations for different fluoroscopic x-ray imaging systems, a different table, formula, and/or model may be provided in memory 33009A for each of the fluoroscopic x-ray imaging systems.

At block 36005, processor 34007 determines whether x-ray emission from x-ray source 3001 to x-ray detector 3005 is present/detected based on information from x-ray presence sensor 33019. By providing x-ray presence sensor 33019 on face 3006 of detector 3005, output from x-ray presence sensor 33019 can be used to determine when a fluoroscopic image/shot is being taken, and thus, when offset information is needed.

According to some embodiments at block 36009, processor 34007 determines an orientation of the C-arm 3009 and/or detector 3005 responsive to detecting an x-ray emission from the x-ray source toward the x-ray detector at block 36005. For example, the orientation of the C-arm and/or detector 3005 may be determined relative to gravity based on an output from inertial measurement unit IMU 33005. By determining the orientation responsive to detecting the x-ray emission, the orientation is determined at the time of taking the fluoroscopic x-ray image/shot. Moreover, the orientation of the C-arm and/or detector 3005 may be determined/ defined with respect to a reference orientation of the C-arm and/or detector 3005, where the reference orientation of the C-arm and/or detector 3005 is defined as the orientation of the C-arm and/or detector 3005 with the x-ray detector vertically above the x-ray source.

According to some embodiments at block 36011, processor 34007 determines an offset of the x-ray source 3001 relative to the x-ray detector 3005 responsive to detecting an x-ray emission from the x-ray source 3001 toward the x-ray detector 3005 at block 36005. For example, the offset of the x-ray source 3001 relative to the x-ray detector 3005 may be determined based on the orientation of the x-ray detector 3005 (and/or C-arm 3009) from block 36009, based on the orientation of the x-ray detector 3005 (and/or C-arm 3009) from block 36009 and based on the correlation in memory 33009A from block 36001, and/or based on the orientation of the x-ray detector 3005 (and/or C-arm 3009) from block 36009 and based on the correlation in memory 33009A being associated with the fluoroscopic x-ray imaging system based on the identification as discussed above with respect to blocks 36001A-C. The offset of the x-ray source relative to the x-ray detector may be determined/defined, for example, using a coordinate system of the x-ray detector where an x-axis and a y-axis are defined in a plane of the x-ray detector and a z axis is defined perpendicular to the plane of the x-ray detector.

According to some embodiments at block 36015, processor 34007 activates a tracking marker through marker array interface 33051 responsive to detecting the x-ray emission from block 36005. For example, the tracking marker may be one of a plurality of light emitting diodes (LEDs) of tracking marker array 33001 and activating the tracking marker may cause the plurality of LEDs to turn on, and/or the tracking marker may be a moveable tracking marker and activating the tracking marker may cause the moveable tracking marker to move from a respective first position to a respective second position. As discussed above with respect to FIG. 33, marker array 33001 may be coupled to array mount 33011 through sterile drape 33015 that covers the fixture and at least a portion of detector 3005. Marker array 33001 (or a tracking marker thereof) may thus be activated by processor 34007 using interface 33051 (e.g., through array mount 33011), for example, using electrical coupling, inductive coupling, mechanical coupling, radio coupling, electromagnetic coupling, magnetic coupling, etc.

According to some embodiments, tracking marker/markers may be activated at block 36015 by turning on one or more light emitting diode (LED) tracking markers responsive to detecting x-ray emission at block 36005. According to some other embodiments, a fixed/passive array of tracking markers and a moveable tracking marker may be provided for the fixture, and the moveable tracking marker may be activated at block 36015 by moving the moveable tracking marker relative to the array of tracking markers responsive to detecting x-ray emissions at block 36005.

According to some embodiments at block 36017, processor 34007 provides an indication of the offset of the x-ray source from block 36011 through communication interface 33009B to the medical navigation system. The offset, for example, may be provided through communication interface 33009B to the medical navigation system via a wired coupling or via a wireless coupling (e.g., via WiFi, Bluetooth, etc.). The medical navigation system can thus use the indication of the offset to provide registration as discussed below.

According to some other embodiments, the correlation between x-ray detector (and/or C-arm) orientations relative to gravity and offsets may be provided at the medical navigation system (instead of the fixture). In such embodiments, processor 34007 may provide an indication of the x-ray detector 3005 (and/or C-arm) orientation relative to gravity through communication interface 33009B to the medical navigation (via wired or wireless coupling, e.g., via WiFi, Bluetooth, etc.) responsive to detecting x-ray emission, and the medical navigation system may use the x-ray detector 3005 (and/or C-arm) orientation relative to gravity and the correlation between x-ray detector 3005 (and/or C-arm) orientations and offsets to determine/provide the offset of the x-ray source relative to the x-ray detector. In either embodiment, processor 34007 may provide information (e.g., the detector/C-arm orientation or the offset) based on the x-ray detector 3005 (and/or C-arm orientation) relative to gravity to the medical navigation system for use by the medical navigation system to perform registration. Because the C-arm and the x-ray detector are connected and/or integrated, an orientation of the x-ray detector 3005 may refer to an orientation of the C-arm, and/or an orientation of the C-arm 3009 may refer to an orientation of the x-ray detector 3005.

Operations of a medical navigation system will now be discussed with reference to the flow chart of FIG. 37 according to some embodiments of inventive concepts. For example, modules may be stored in memory 35009 of FIG. 35, and these modules may provide instructions so that when the instructions of a module are executed by processor 35007, processor 35007 performs respective operations of the flow chart of FIG. 35.

According to some embodiments at block 37005, processor 35007 receives information defining a first patient image from a fluoroscopic x-ray imaging system through communication interface 35051, wherein the fluoroscopic x-ray imaging system includes a C-arm 3009, an x-ray source 3001 at a first end of the C-arm, and an x-ray detector 3005 at a second end of the C-arm. The first patient image may include shadows corresponding to an x-ray opaque fiducial pattern of the fixture.

According to some embodiments at block 37009, processor 35007 receives an indication of a first offset of the x-ray source 3001 relative to the x-ray detector 3005, wherein the first offset is associated with the first patient image, and wherein the indication of the first offset is received through communication interface 35051.

According to some embodiments, receiving the information defining the first patient image at block 37005 and receiving the indication of the first offset at block 37009 may include receiving a digital file (e.g., a Digital Imaging and Communication in Medicine DOCOM file) including the information defining the first patient image and the indication of the first offset. According to some other embodiments, the first offset may be received separately from the information defining the first patient image. For example, the first offset may be received via a wireless coupling, such as a WiFi coupling, a Bluetooth coupling, etc.

According to some embodiments at block 37011, processor 35007 determines a first location (also referred to as position) of the x-ray detector 3005 and/or x-ray source 3001 based on a first location (also referred to as position) of tracking marker array 33001 on x-ray detector 3005 determined using tracking information from tracking sensors (e.g., tracking cameras 200), with the first location being associated with the first patient image. For example, the first location of the x-ray detector may be determined based on a location of a tracking marker array 33001 determined using the tracking information from the tracking sensors, and/or the first location of the x-ray detector may be determined responsive to detecting a first activation of a tracking marker (e.g., one or more of the markers of array 33001) using the tracking information from the tracking sensors. Activation may be detected, for example, based on detecting movement of a marker(s) and/or based on detecting active illumination of a marker(s).

According to some embodiments at block 37012, processor 35007 determines a first location (also referred to as position) of a surveillance marker 8091 using tracking information from the tracking sensors, with the first location of the surveillance marker 8091 being associated with the first patient image. At block 37014, processor 35007 may determine that the first location of the x-ray detector and/or x-ray source is valid based on the first location of the surveillance marker 8091 relative to the tracking marker array at the first location of the tracking marker array. If processor 35007 does not determine that the first location of the x-ray detector is valid, validation based on the first patient image, the first offset, and/or the first location of the x-ray detector may be blocked and/or another first patient image (and associated information, e.g., offset) may be requested.

According to some embodiments at block 37015, processor 35007 receives information defining a second patient image from the fluoroscopic x-ray imaging system through communication interface 35051, with the first and second patient images being different.

According to some embodiments at block 37019, processor 35007 receives an indication of a second offset of the x-ray source 3001 relative to the x-ray detector 3005, wherein the second offset is associated with the second patient image, wherein the first and second offsets are different, and wherein the indication of the second offset is received through communication interface 35051.

According to some embodiments, receiving the information defining the second patient image at block 37005 and receiving the indication of the second offset at block 37009 may include receiving a digital file (e.g., a Digital Imaging and Communication in Medicine DOCOM file) including the information defining the second patient image and the indication of the second offset. According to some other embodiments, the second offset may be received separately from the information defining the second patient image. For example, the second offset may be received via a wireless coupling, such as a WiFi coupling, a Bluetooth coupling, etc.

According to some embodiments at block 37021, processor 35007 determines a second location (also referred to as position) of the x-ray detector 3005 and/or x-ray source 3001 based on a second location (also referred to as position) of tracking marker array 33001 on x-ray detector 3005 determined using tracking information from tracking sensors (e.g., tracking cameras 200), with the second location being associated with the second patient image, and with the first and second patient images being different. For example, the second location of the x-ray detector may be determined based on a location of a tracking marker array 33001 determined using the tracking information from the tracking sensors, and/or the second location of the x-ray detector may be determined responsive to detecting a second activation of a tracking marker (e.g., one or more of the markers of array 33001) using the tracking information from the tracking sensors. Activation may be detected, for example, based on detecting movement of a marker(s) and/or based on detecting active illumination of a marker(s).

According to some embodiments at block 37022, processor 35007 determines a second location (also referred to as position) of the surveillance marker 8091 using tracking information from the tracking sensors, with the second location of the surveillance marker 8091 being associated with the second patient image. At block 37014, processor 35007 may determine that the second location of the x-ray detector and/or x-ray source is valid based on the second location of the surveillance marker 8091 relative to the tracking marker array at the second location of the tracking marker array. If processor 35007 does not determine that the second location of the x-ray detector is valid, validation based on the second patient image, the second offset, and/or the second location of the x-ray detector may be blocked and/or another second patient image (and associated information, e.g., offset) may be requested.

According to some embodiments at block 37025, processor 35007 provides a registration between a tracking coordinate system for a physical space monitored by the tracking sensors (e.g., tracking cameras 200) and an image coordinate system for the first and second patient images from the fluoroscopic x-ray imaging system, wherein the registration is provided based on the indications of the first and second offsets. For example, the registration between the tracking coordinate system and the image coordinate system may be provided based on the first and second offsets, based on the first and second locations of the x-ray detector, based on the correlation of offsets of x-ray source relative to the x-ray detector as a function of an orientation of the x-ray detector relative to gravity, and/or based on the shadows in the first and second patient images. According to some embodiments, processor 35007 may determine a first location of the x-ray source based on the first location of the x-ray detector (e.g., determined using information regarding marker array 33001 received through optical tracking/camera system) and the first offset, processor 35007 may determine a second location of the x-ray source based on the second location of the x-ray detector (e.g., determined using information regarding marker array 33001 received through optical tracking/camera system) and the second offset, and the registration may be provided based on one or more of the correlation of offsets, based on the first offset, based on the second offset, based on the first and second shadows, based on the first location of the x-ray detector, based on the second location of the x-ray detector, based on the first location of the x-ray source, and/or based on the second location of the x-ray source. Moreover, registration may be provided responsive to determining that the first and second locations of the x-ray detector are valid at blocks 37014 and 37024.

For example, the registration may be provided responsive to detecting activation of a tracking marker (e.g., one or more of the markers of array 33001) using the tracking information from the tracking sensors. Activation may be detected, for example, based on detecting movement of the marker(s) and/or based on detecting active illumination of the marker(s). For example, the registration may be provided responsive to detecting activation of a tracking marker (e.g., one or more of the markers of array 33001) using the tracking information from the tracking sensors. Activation may be detected, for example, based on detecting movement of the marker(s) and/or based on detecting active illumination of the marker(s).

According to some embodiments at block 37029, processor 35007 may control the robotic actuator to move the end-effector to a target trajectory relative to the patient based on the first and second patient images from the fluoroscopic x-ray imaging system and based on the registration between the tracking coordinate system and the image coordinate system. For example, controlling the robotic actuator may include controlling the robotic actuator to move the end-effector to the target trajectory relative to the patient based on the first and second patient images from the fluoroscopic x-ray imaging system, based on the registration between the tracking coordinate system and the image coordinate system, and based on a location of the end-effector determined using tracking information from the tracking sensors. According to some other embodiments, processor 35007 may render an image on a display based on the first and second patient images of blocks 37005 and 37015 and based on the registration. In such embodiments, processor 35007 may render the image to further include a portion thereof based on an image received through the optical tracking/ camera system and/or to further include a portion thereof based on a virtual element (e.g., a virtual screw or other medical device) that may be used for planning.

As discussed above with respect to FIG. 37, the medical navigation system may receive respective offsets from the fixture at blocks 37009 and 37019 so that the correlation between x-ray detector 3005 (and/or C-arm) orientations relative to gravity and offsets may be provided at the fixture and the offset may be determined at the fixture. According to some other embodiments, the correlation between x-ray detector 3005 (and/or C-arm) orientations and offsets may be provided in memory 35009 at the medical navigation system, and the medical navigation system may instead receive (through communication interface 35051) indications of the x-ray detector 3005 (and/or C-arm) orientation relative to gravity at blocks 37009 and 37019. In such embodiments, processor 35007 may determine the respective offsets using the indications of the x-ray detector 3005 (and/or C-arm) orientations and the correlation between x-ray detector 3005 (and/or C-arm) orientations and offsets to determine/provide the offset of the x-ray source relative to the x-ray detector. In either embodiment, processor 35007 may use information (e.g., the C-arm/detector orientation or the offset) received from the fixture to determine/provide the offsets that are used to perform registration.

According to still other embodiments, the fixture may not provide any information regarding an orientation of the C-arm/detector or an offset. In such embodiments, processor 35007 may determine orientations of the C-arm/detector at blocks 37009 and 37019 for respective images using a gravity vector on the C-arm and/or x-ray detector as discussed above with respect to FIGS. 23A, 23B, 23C, 24A, 24B, 27A, and 31. As discussed above, the gravity vector includes at least two suspended tracking markers, and processor 35007 can determine the orientations of the c-arm/detector relative to gravity by determining positions of the gravity vector tracking markers based on information received through the tracking sensors/cameras at the time of the respective patient image. In such embodiments, the fixture may signal the timing of an image/shot by activating one or more markers of the active tracking marker array, and responsive to detecting activation of the one or more markers of the active tracking marker array, processor 35007 may use the gravity vector to determine the orientation of the c-arm/detector for the respective image. Where the gravity vector includes fixed tracking markers 4005A, 4005B, 4005C, and 4005D and moveably suspended tracking markers 4001A and 4001B, processor 35007 can use the fixed tracking markers to determine a location of the x-ray detector, and processor 35007 can used the moveably suspended markers to determine the orientation relative to gravity.

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belong. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Although several embodiments of inventive concepts have been disclosed in the foregoing specification, it is understood that many modifications and other embodiments of inventive concepts will come to mind to which inventive concepts pertain, having the benefit of teachings presented in the foregoing description and associated drawings. It is thus understood that inventive concepts are not limited to the specific embodiments disclosed hereinabove, and that many modifications and other embodiments are intended to be included within the scope of the appended claims. It is further envisioned that features from one embodiment may be combined or used with the features from a different embodiment(s) described herein. Moreover, although specific terms are employed herein, as well as in the claims which follow, they are used only in a generic and descriptive sense, and not for the purposes of limiting the described inventive concepts, nor the claims which follow. The entire disclosure of each patent and patent publication cited herein is incorporated by reference herein in its entirety, as if each such patent or publication were individually incorporated by reference herein. Various features and/or potential advantages of inventive concepts are set forth in the following claims.

What is claimed is:

1. A fixture for a fluoroscopic x-ray imaging system, wherein the fluoroscopic x-ray imaging system includes a C-arm, an x-ray source at a first end of the C-arm, and an x-ray detector at a second end of the C-arm, the fixture comprising:

an x-ray opaque fiducial pattern in a single plane, wherein the fixture is configured to be coupled to the C-arm so that the x-ray opaque fiducial pattern is on an x-ray beam path between the x-ray detector and the x-ray emitter, wherein a medical navigation system is configured to receive a first patient image from the fluoroscopic imaging system corresponding to a first orientation of the C-arm with the first patient image including first shadows corresponding to the x-ray opaque fiducial pattern, to receive a second patient image from the fluoroscopic imaging system corresponding to a second orientation of the C-arm with the second patient image including second shadows corresponding to the x-ray opaque fiducial pattern, and to provide a registration between a tracking coordinate system for a physical space monitored by tracking cameras and an image coordinate system for the first patient image and the second patient image based on a correlation of offsets of the x-ray source relative to the x-ray detector.

2. The fixture of claim 1, wherein the x-ray opaque fiducial pattern comprises plurality of BB fiducials residing in the single plane.

3. The fixture of claim 2, wherein the plurality of BB fiducials includes first, second, third, and fourth clusters of BB fiducials, wherein the first cluster of BB fiducials is spaced apart from the third cluster of BB fiducials along a first axis, wherein the second cluster of BB fiducials is spaced apart from the fourth cluster of BB fiducials along a second axis, and wherein the first axis is orthogonal with respect to the second axis.

4. The fixture of claim 1, wherein the x-ray opaque fiducial pattern comprises first, second, third, and fourth x-ray opaque fiducial segments that extend in different directions from a common point, wherein the first x-ray opaque fiducial segment has a first break at a first distance from the common point, wherein the second x-ray opaque fiducial segment has a second break at a second distance from the common point greater than the first distance, and wherein the third x-ray opaque fiducial segment has a third break at a third distance from the common point greater than the second distance.

5. The fixture of claim 1, wherein providing the registration based on the correlation of offsets of the x-ray source relative to the x-ray detector as a function of an orientation of the x-ray detector relative to gravity comprises providing the registration based on the correlation, based on a first orientation of the x-ray detector relative to gravity associated with the first orientation of the C-arm, and based on a second orientation of the x-ray detector relative to gravity associated with the second orientation of the C-arm.

6. The fixture of claim 5, wherein the fixture includes an inertial measurement unit (IMU) configured to detect an orientation of the x-ray detector relative to gravity, and wherein the first orientation of the x-ray detector relative to gravity is determined based on a first output from the inertial measurement unit with the C-arm in the first orientation, and wherein the second orientation of the x-ray detector relative to gravity is determined based on a second output from the inertial measurement unit with the C-arm in the second orientation.

7. The fixture of claim 5, further comprising:

a gravity vector coupled with the x-ray detector, wherein the gravity vector includes a pair of movably suspended optical tracking markers, wherein the first orientation of the x-ray detector relative to gravity is determined based on first positions of the pair of movably suspended optical tracking markers with the C-arm in the first orientation, and wherein the second orientation of the x-ray detector relative to gravity is determined based on second positions of the pair of movably suspended optical tracking markers with the C-arm in the second orientation.

8. The fixture of claim 1, wherein the fixture includes a plurality of mounting pins, wherein each of the mounting pins is configured to detachably mate with a respective one of the mounting sockets.

9. The fixture of claim 1, wherein the medical navigation system is configured to generate the correlation of offsets based on an air-shot image from the fluoroscopic imaging system wherein the air-shot image corresponds to one orientation of the C-arm.

10. The fixture of claim 9, wherein the x-ray opaque fiducial pattern is a first x-ray opaque fiducial pattern, wherein a second x-ray opaque fiducial pattern is temporarily coupled with the x-ray detector between the fixture and the x-ray source so that the air-shot image includes shadows corresponding to the first x-ray opaque fiducial pattern and the second x-ray opaque fiducial pattern, and wherein the medical navigation system is configured to generate the correlation of offsets based on the air-shot image including the shadows corresponding to the first x-ray opaque fiducial pattern and the second x-ray opaque fiducial pattern.

11. The fixture of claim 9, wherein the x-ray opaque fiducial pattern is a first x-ray opaque fiducial pattern, wherein a second x-ray opaque fiducial pattern is temporarily coupled with the x-ray source between the fixture and the x-ray source so that the air-shot image includes shadows corresponding to the first x-ray opaque fiducial pattern and the second x-ray opaque fiducial pattern, and wherein the medical navigation system is configured to generate the correlation of offsets based on the air-shot image including the shadows corresponding to the first x-ray opaque fiducial pattern and the second x-ray opaque fiducial pattern.

12. The fixture of claim 9, wherein the medical navigation system is configured to generate the correlation of offsets based on the air-shot image and based on positions of the x-ray source corresponding to respective different orientations of the C-arm, wherein the positions of the x-ray source are determined based on an optical tracking array coupled with the x-ray source.

13. The fixture of claim 1 further comprising:
an optical tracking array coupled with the fixture; and
an optical surveillance marker coupled with the x-ray detector and/or the x-ray source;
wherein the medical navigation system is configured to determine a first position of the x-ray detector and/or the x-ray source associated with the first patient image based on the optical tracking array, validate the first position of the x-ray detector and/or the x-ray source based on a first position of the optical surveillance marker associated with the optical tracking array, determine a second position of the x-ray detector and/or the x-ray source associated with the second patient image based on the optical tracking array, validate the second position of the x-ray detector and/or the x-ray source based on a second position of the optical surveillance marker associated with the optical tracking array, and provide the registration based on the correlation of offsets, based on the first and second shadows, based on the first position of the x-ray detector and/or the x-ray source, based on validating the first position of the x-ray detector and/or the x-ray source, based on the second position of the x-ray detector and/or the x-ray source, and based on validating the second position of the x-ray detector and/or the x-ray source.

14. A fixture for a fluoroscopic x-ray imaging system, wherein the fluoroscopic x-ray imaging system includes a C-arm, an x-ray source at a first end of the C-arm, and an x-ray detector at a second end of the C-arm, the fixture comprising:
a processor; and
memory coupled with the processor, wherein the memory includes instructions that are executable by the processor so that the fixture is configured to,
detect an x-ray emission from the x-ray source toward the x-ray detector,
determine an offset of the x-ray source relative to the x-ray detector, responsive to detecting the x-ray emission, and
provide an indication of the offset of the x-ray source to a medical navigation system.

15. The fixture of claim 14, wherein the memory includes instructions that are executable by the processor so that the fixture is further configured to,
determine an orientation of the x-ray detector responsive to detecting the x-ray emission,
wherein the offset of the x-ray source relative to the x-ray detector is determined based on the orientation of the x-ray detector.

16. The fixture of claim 15, wherein the memory includes instructions that are executable by the processor so that the fixture is further configured to,
provide in memory a correlation between different orientations of the x-ray detector and respective offsets of the x-ray source relative to the x-ray detector,
wherein the offset of the x-ray source relative to the x-ray detector is determined based on the orientation of the x-ray detector and based on the correlation in memory.

17. The fixture of claim 14 further comprising:
an x-ray opaque fiducial pattern in a single plane; and
a mounting structure configured to provide a detachable mechanical coupling between the fixture and the C-arm of the fluoroscopic x-ray imaging system so that the fiducials are on an x-ray beam path between the x-ray detector and the x-ray source when the fixture is coupled to the C-arm using the mounting structure.

18. A fixture for a fluoroscopic x-ray imaging system, wherein the fluoroscopic x-ray imaging system includes a C-arm, an x-ray source at a first end of the C-arm, and an x-ray detector at a second end of the C-arm, the fixture comprising:
an x-ray opaque fiducial pattern in a single plane, wherein the fixture is configured to be coupled to the C-arm so that the x-ray opaque fiducial pattern is on an x-ray beam path between the x-ray detector and the x-ray emitter,
wherein a medical navigation system is configured to receive a first patient image from the fluoroscopic imaging system corresponding to a first orientation of the C-arm with the first patient image including first shadows corresponding to the x-ray opaque fiducial pattern, to receive a second patient image from the fluoroscopic imaging system corresponding to a second orientation of the C-arm with the second patient image including second shadows corresponding to the x-ray opaque fiducial pattern, and to provide a registration between a tracking coordinate system for a physical space monitored by tracking cameras and an image coordinate system for the first patient image and the second patient image based on a correlation of offsets of the x-ray source relative to the x-ray detector relative to the x-ray detector as a function of an orientation of the x-ray detector relative to gravity and based on the first shadows in the first patient image and the second shadows in the second patient image.

19. The fixture of claim 18, wherein the x-ray opaque fiducial pattern comprises plurality of BB fiducials residing in the single plane.

20. The fixture of claim 18, wherein the plurality of BB fiducials includes first, second, third, and fourth clusters of BB fiducials, wherein the first cluster of BB fiducials is spaced apart from the third cluster of BB fiducials along a first axis, wherein the second cluster of BB fiducials is spaced apart from the fourth cluster of BB fiducials along a second axis, and wherein the first axis is orthogonal with respect to the second axis.

* * * * *